(12) United States Patent
Longman et al.

(10) Patent No.: US 10,160,805 B2
(45) Date of Patent: Dec. 25, 2018

(54) METHODS OF TREATING INFLAMMATORY BOWEL DISEASE BY ADMINISTERING TUMOR NECROSIS FACTOR-LIKE LIGAND 1A OR AN AGONISTIC DEATH-DOMAIN RECEPTOR 3 ANTIBODY

(71) Applicants: Randy S. Longman, New Rochelle, NY (US); Gretchen E. Diehl, New York, NY (US); Dan R. Littman, New York, NY (US)

(72) Inventors: Randy S. Longman, New Rochelle, NY (US); Gretchen E. Diehl, New York, NY (US); Dan R. Littman, New York, NY (US)

(73) Assignees: New York University, New York, NY (US); Cornell University, Ithaca, NY (US)

( * ) Notice: Subject to any disclaimer, the term of this patent is extended or adjusted under 35 U.S.C. 154(b) by 0 days.

(21) Appl. No.: 14/797,588

(22) Filed: Jul. 13, 2015

(65) Prior Publication Data

US 2016/0009802 A1 Jan. 14, 2016

Related U.S. Application Data

(60) Provisional application No. 62/023,816, filed on Jul. 11, 2014.

(51) Int. Cl.
| C07K 16/28 | (2006.01) |
| G01N 33/50 | (2006.01) |
| G01N 33/68 | (2006.01) |

(52) U.S. Cl.
CPC ......... *C07K 16/28* (2013.01); *G01N 33/5023* (2013.01); *G01N 33/5047* (2013.01); *G01N 33/6869* (2013.01); *G01N 2333/54* (2013.01); *G01N 2500/10* (2013.01)

(58) Field of Classification Search
CPC . C07K 16/28; G01N 33/5047; G01N 2500/10
See application file for complete search history.

(56) References Cited

U.S. PATENT DOCUMENTS

| 8,766,034 B2 | 7/2014 | Shih et al. | |
| 2016/0015779 A1* | 1/2016 | Podack | C07K 16/2878 424/172.1 |

FOREIGN PATENT DOCUMENTS

| WO | 2008106451 | 9/2008 |
| WO | 2009064854 | 5/2009 |
| WO | 2012064682 | 5/2012 |

OTHER PUBLICATIONS

Bamias G, et al. PNAS. 103(22):8441-8446. May 30, 2006. Available online at—doi: 10.1073/pnas.0510903103.*
Prehn JL, et al. Clinical Immunology. 112(1):66-77. Jul. 2004. Available online at—doi:10.1016/j.clim.2004.02.007.*
Young HA and Tovey MG. PNAS. 103(22). May 30, 2006. Available online at—doi: 10.1073/pnas.0602655103.*
Meylan F, et al. Immunity. 29(1):79-89. Jul. 18, 2008. Available online at—doi: 10.1016/j.immuni.2008.04.021.*
Antignano F and Zaph Z. Current Immunology Reviews. 9:111-117. 2013.*
Yu X, et al. Mucosal Immunology. 7:730-740. 2014. Available online at—doi:10.1038/mi.2013.92.*
Ahn YO, et al. Eur J Immunol. 45:2335-2342. 2015. Available online at—doi:10.1002/eji.201445213.*
A Yoshiro and N Minoru. Mediators Inflamm. Article 258164. pp. 1-9. 2013. Available online at—doi:10.1155/2013/258164.*
Facco M et al. Clin Mol Allergy. 13(1): 16-26. 2015. Available online at—10.1186/s12948-015-0022-z.*
Bamias G, et al. (Nov. 1, 2003) J Immunol. 171(9):4868-4874. (DOI: https://doi.org/10.4049/jimmunol.171.9.4868).*
Bamias G, et al. (May 30, 2006) Proc Natl Acad Sci USA. 103(22):8441-6. (DOI: 10.1073/pnas.0510903103).*
Buonocore et al., "Innate lymphoid cells drive interleukin-23-dependent innate intestinal pathology", Nature, 2010, 464:1371-1375.
Cella et al. , "A human NK cell subset provides an innate source of IL-22 for mucosal immunity", Nature, 2009, 457:722-725.
Diehl et al., "Microbiota restricts trafficking of bacteria to mesenteric lymph nodes by CX3CR1hi cells", Nature, 2013, 494:116-120.
Geremia et al., "IL-23-responsive innate lymphoid cells are increased in inflammatory bowel disease", J Exp Med, 2011, 208:1127-1133.
Hanash et al. "Interleukin-22 protects intestinal stem cells from immune-mediated tissue damage and regulates sensitivity to graft versus host disease", Immunity, 2012, 37:339-350.
Kamada et al., "Unique CD14 intestinal macrophages contribute to the pathogenesis of Crohn disease via IL-23/IFN-gamma axis", J Clin Invest, 2008, 118:2269-2280.
Meylan et al., "The TNF-family cytokine TL1A promotes allergic immunopathology through group 2 innate lymphoid cells", Mucosal Immunol, 2014, 7:958-968.
Pappu et al., "TL1A-DR3 interaction regulates Th17 cell function and Th17-mediated autoimmune disease", J Exp Med, 2008, 205:1049-1062.
Pickert et al., "STAT3 links IL-22 signaling in intestinal epithelial cells to mucosal wound healing", J Exp Med, 2009, 206:1465-1472.
Satoh-Takayama et al., "Microbial flora drives interleukin 22 production in intestinal NKp46+ cells that provide innate mucosal immune defense", Immunity, 2008, 29:958-970.
Schreiber et al., "Intestinal monocytes and macrophages are required for T cell polarization in response to Citrobacter rodentium", J Exp Med, 2013, 210:2025-2039.

(Continued)

*Primary Examiner* — Robert S Landsman
(74) *Attorney, Agent, or Firm* — Klauber & Jackson LLC

(57) ABSTRACT

Methods and compositions for treating inflammatory bowel disease by promoting mucosal healing in the gastrointestinal (GI) tract are encompassed herein. More particularly, methods and compositions described herein relate to agents that activate mononuclear phagocytes (MNPs) in the GI tract and, in turn, regulate the activity of interleukin (IL)-22-producing group 3 innate lymphoid cells (ILC3) in close proximity thereto.

17 Claims, 27 Drawing Sheets

Specification includes a Sequence Listing.

(56) References Cited

OTHER PUBLICATIONS

Shih et al., "Microbial induction of inflammatory bowel disease associated gene TL1A (TNFSF15) in antigen presenting cells", Eur J Immunol, 2009, 39:3239-3250.
Kamada et al., "TL1A produced by lamina propria macrophages induces Th1 and Th17 immune responses in cooperation with IL-23 in patients with Crohn's disease", Inflamm Bowel Dis, 2010, 16:568-75.
Longman et al., "CX3CR1+ mononuclear phagocytes support colitis-associated innate lymphoid cell production of IL-22", J Exp Med, 2014, 211:1571-1583.
Takedatsu et al., "TL1A (TNFSF15) Regulates the Development of Chronic Colitis by Modulating Both T-Helper 1 and T-Helper 17 Activation", Gastroenterology, 2008, 135:552-567.
Shih et al., "Insights into TL1A and IBD Pathogenesis", D. Wallach et al. (eds.), Advances in TNF Family Research, Advances in Experimental Medicine and Biology 691, 2011, Chapter 29:279-288.
Jones et al., "Naive and activated T cells display differential responsiveness to TL1A that affects Th17 generation, maintenance, and proliferation", FASEB J., 2011, 25:409-419.
Papadakis, "TL1A Synergizes with IL-12 and IL-18 to Enhance IFN-Production in Human T Cells and NK Cells1", The Journal of Immunology, 2004, 172: 7002-7007.
Papadakis, "Dominant Role for TL1A/DR3 Pathway in IL-12 plus IL-18-Induced IFN-gamma Production by Peripheral Blood and Mucosal CCR9+ T Lymphocytes", The Journal of Immunology, 2005, 174: 4985-4990.
Saruta et al., "Phenotype and Effector Function of CC Chemokine Receptor 9-Expressing Lymphocytes in Small Intestinal Crohn's Disease", The Journal of Immunology, 2007, 178: 3293-3300.
Shih et al., "Inhibition of a novel fibrogenic factor Tl1a reverses established colonic fibrosis", Mucosal Immunol, 2014, 7:1492-1503.
Prehn et al., "The T Cell Costimulator TL1A Is Induced by FcgammaR Signaling in Human Monocytes and Dendritic Cells", The Journal of Immunology, 2007, 178:4033-4038.
Prehn et al., "Potential role for TL1A, the new TNF-family member and potent costimulator of IFN-gamma, in mucosal inflammation", Clinical Immunology, 2004, 112:66-77.
Chassaing et al., "Dextran Sulfate Sodium (DSS)-Induced Colitis in Mice", Curr Protoc Immunol, Feb. 4, 2014, 104:Unit 15.25 . . . doi: 10.1002/0471142735.im1525s104.:1-16.
Heller et al., "Oxazolone Colitis, a Th2 Colitis Model Resembling Ulcerative Colitis, Is Mediated by IL-13-Producing NK-T Cells", Immunity, 2002, 17:629-638.
Camelo et al., "Blocking IL-25 signalling protects against gut inflammation in a type-2 model of colitis by suppressing nuocyte and NKT derived IL-13", J Gastroenterol , 2012, 47:1198-1211.
Croft et al., "Clinical targeting of the TNF and TNFR superfamilies", Nat Rev Drug Discov, 2013, 12:147-168.
de Vries et al., "Appropriate infliximab infusion dosage and monitoring: results of a panel meeting of rheumatologists, dermatologists and gastroenterologists", Br J Clin Pharmacol, 2010, 71:7-19.
Kirton, Calderdale and Huddersfield NHS Foundation Trust, "Protocol for Infliximab Infusion (Adults)", 2011.
Kanyanta, Surrey and Sussex Healthcare NHS Trust, "Guideline for the use of Infliximab (Remicade®) in patients with Inflammatory Bowel Disease (IBD)", 2014.
University of North Carolina (UNC), "UNC Inflammatory Bowel Disease Drug Protocol Adalimumab (HUMIRA)", 2016.
University of North Carolina (UNC), "UNC Inflammatory Bowel Disease Drug Protocol Certolizumab Pegol (CIMZIA)", 2016.
Wen et al., "TL1A-induced NF-kB Activation and c-IAP2 Production Prevent DR3-mediated Apoptosis in TF-1 Cells", The Journal of Biological Chemistry, 2003, 278:39251-39258.
Wolf et al., "Tregs Expanded In Vivo by INFRSF25 Agonists Promote Cardiac Allograft Survival", Transplantation, 2012, 94:569-573.

* cited by examiner

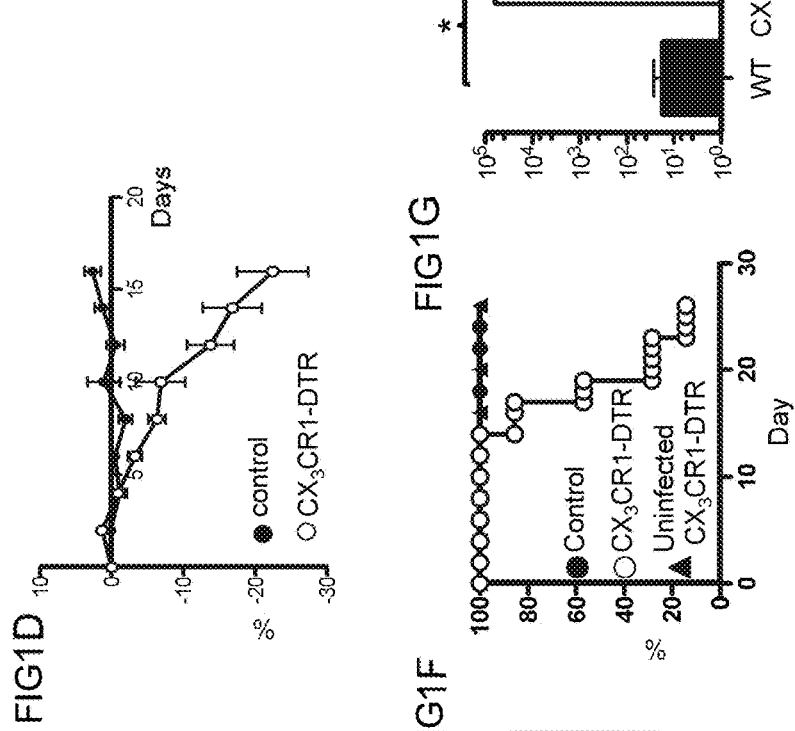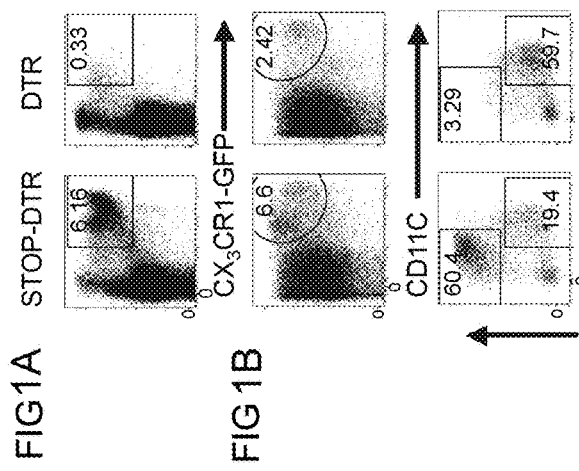

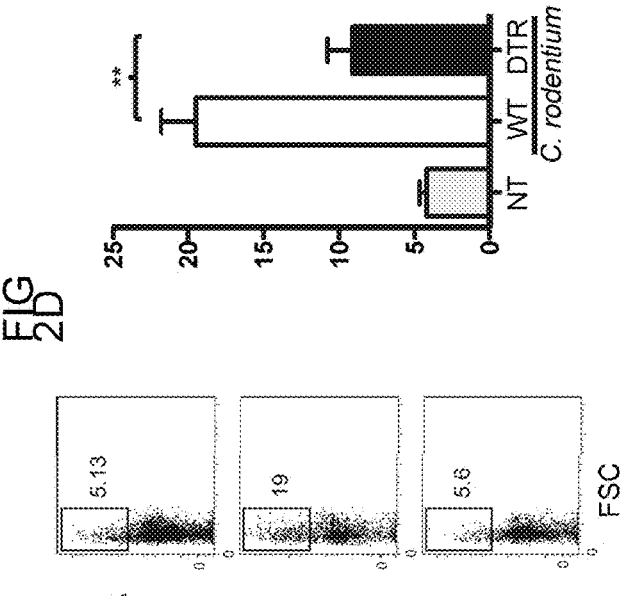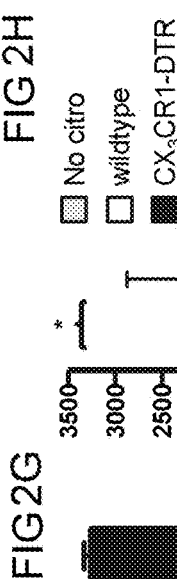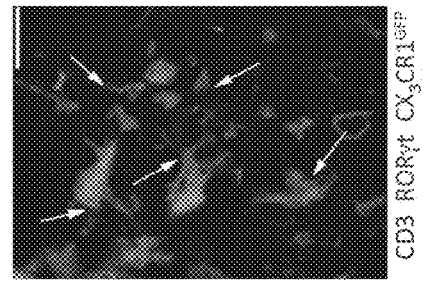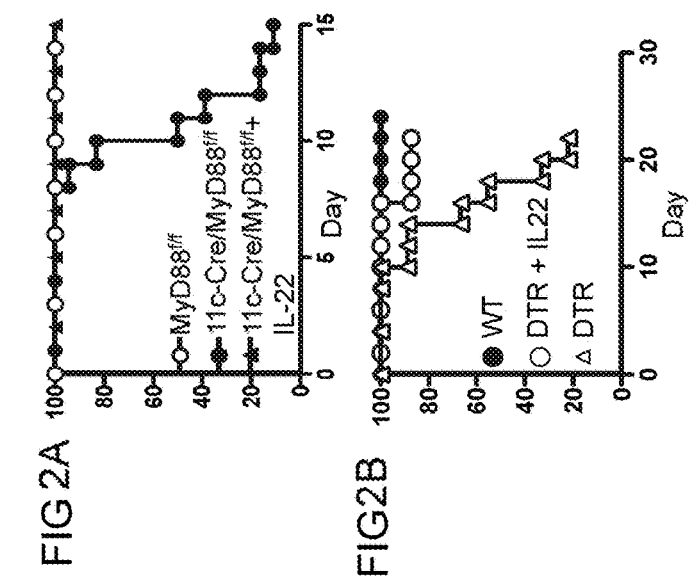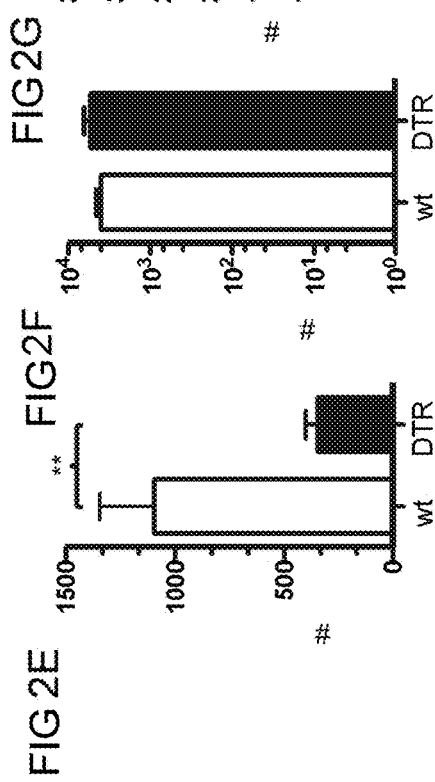

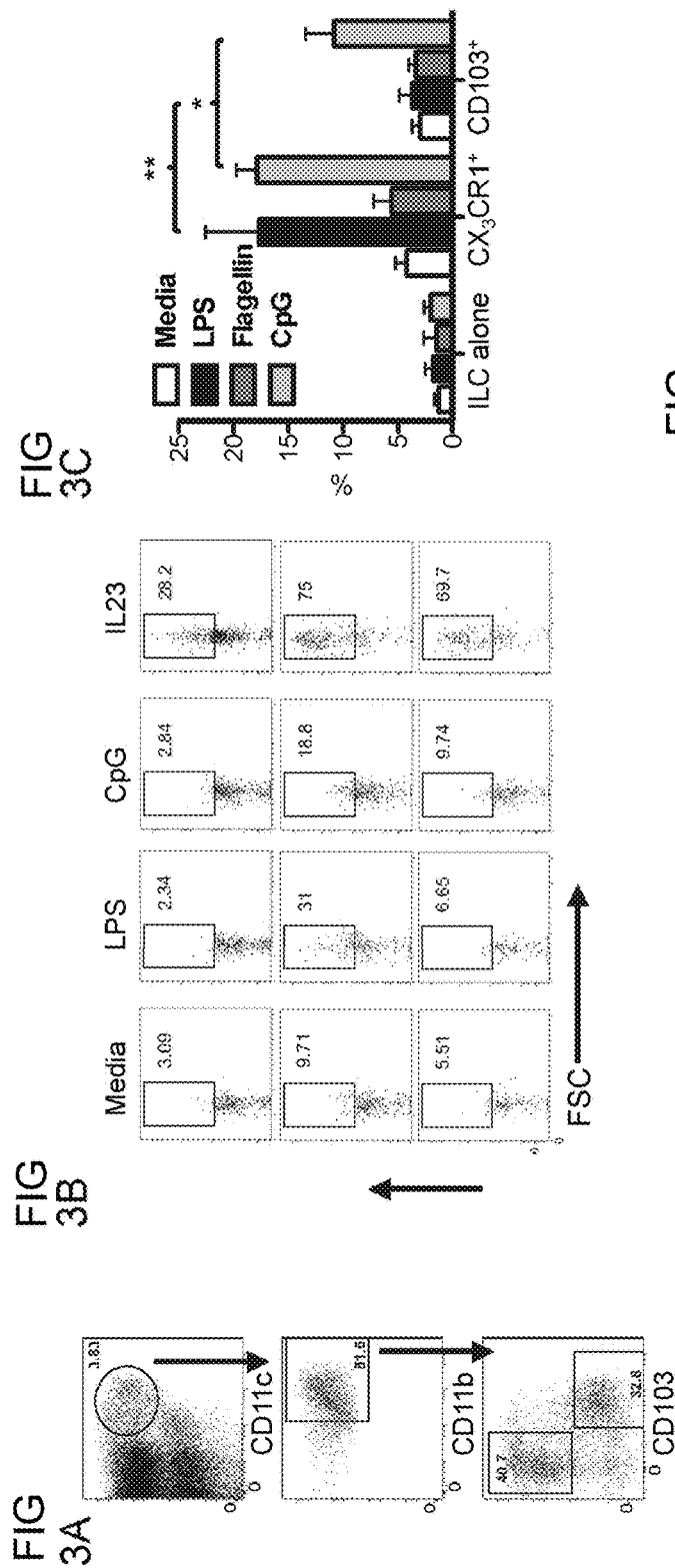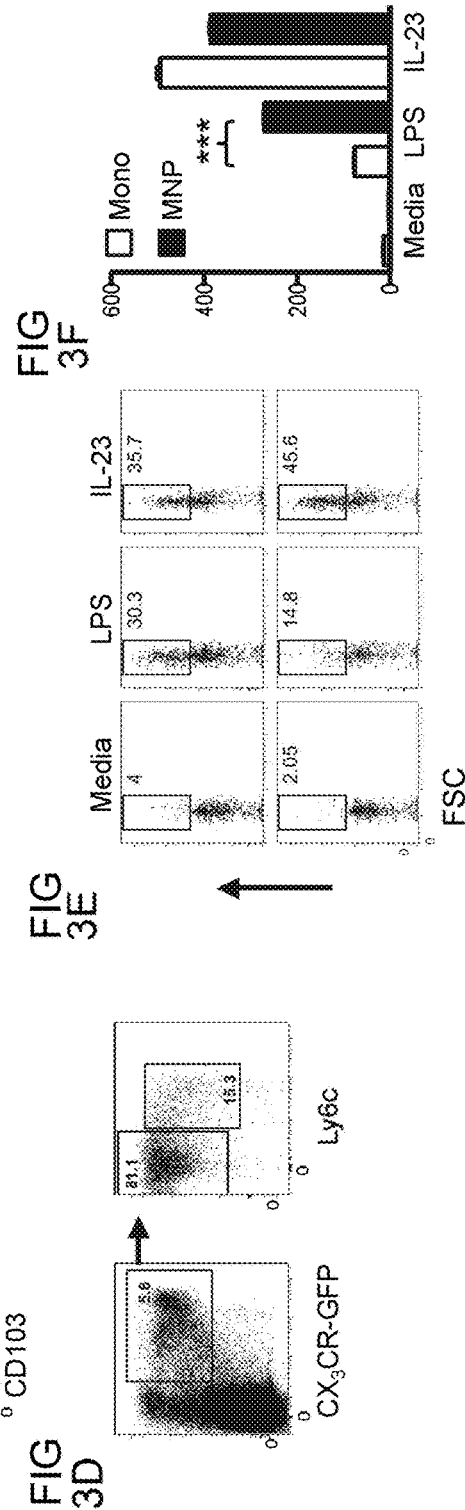

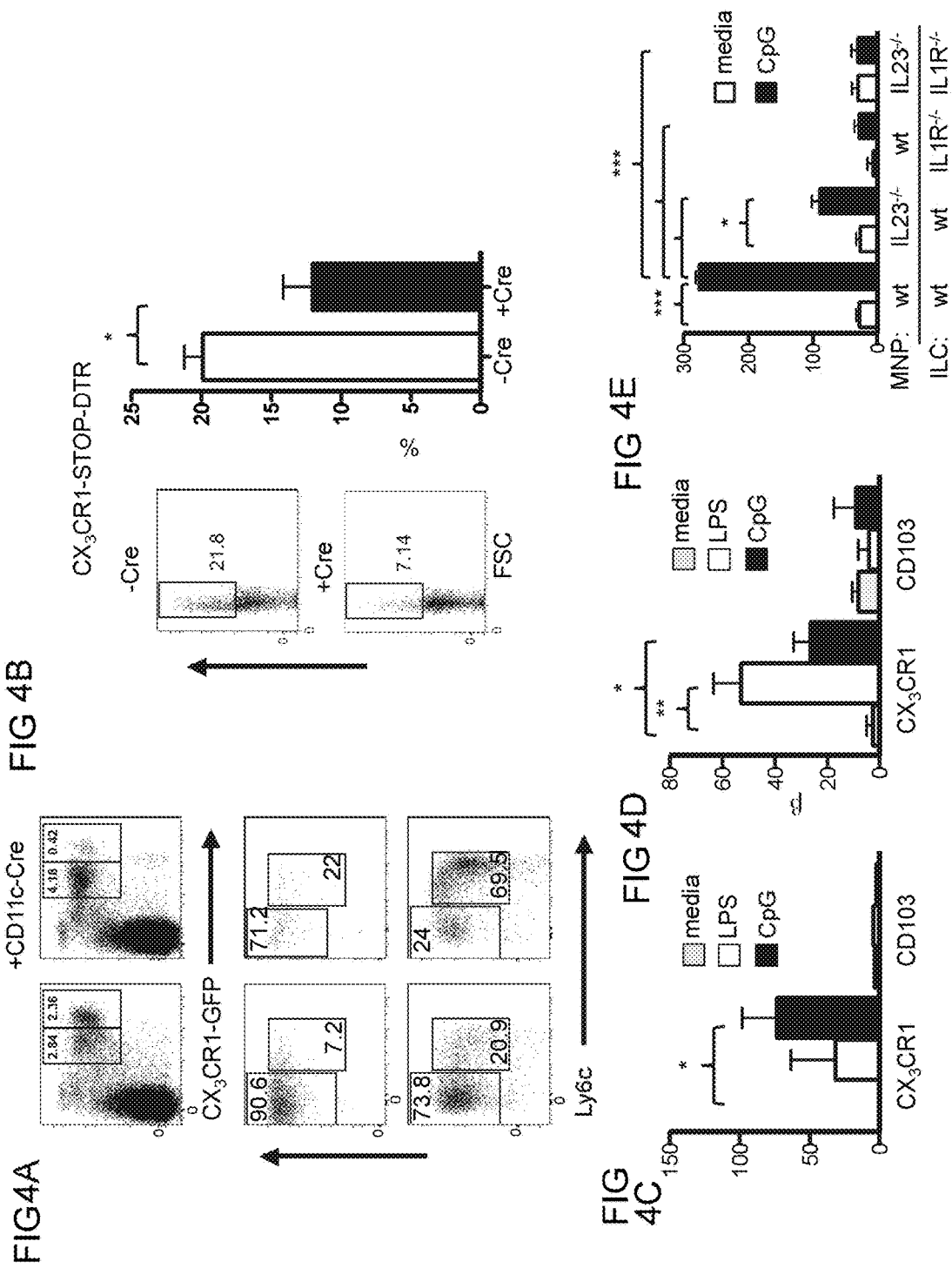

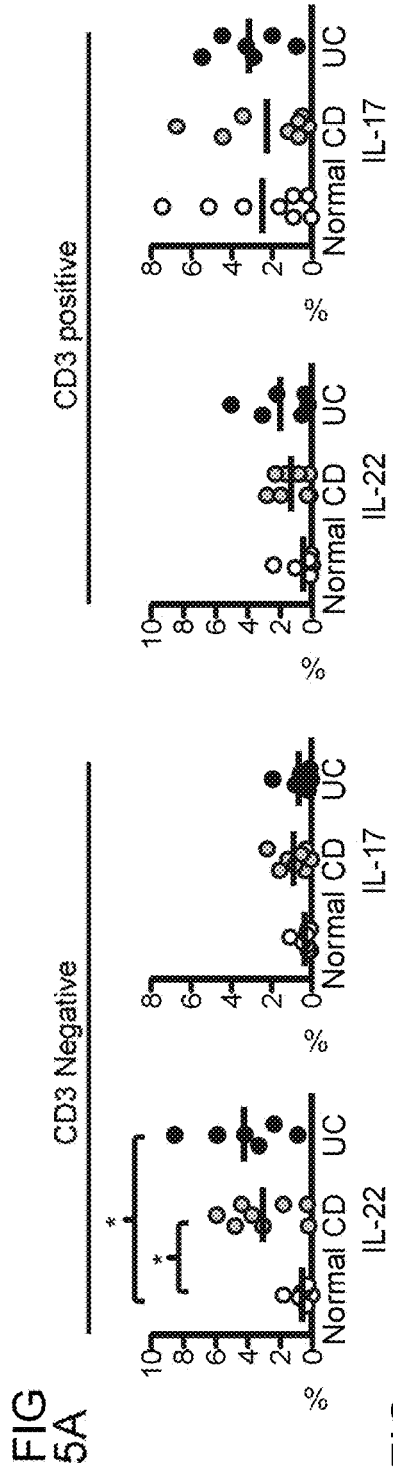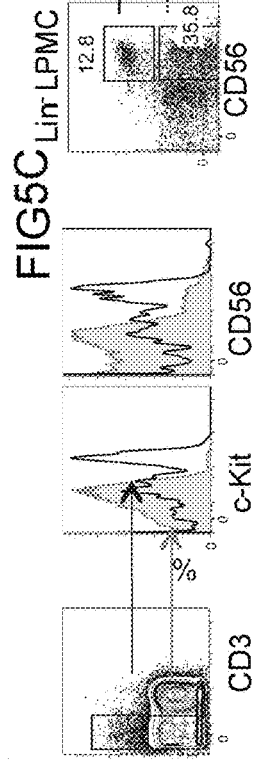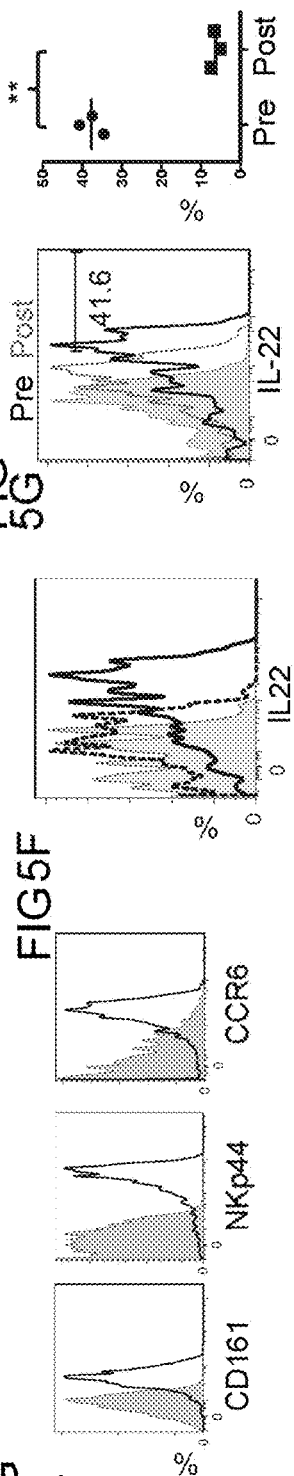

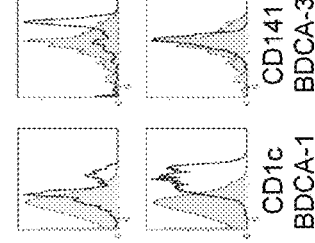
FIG 6A
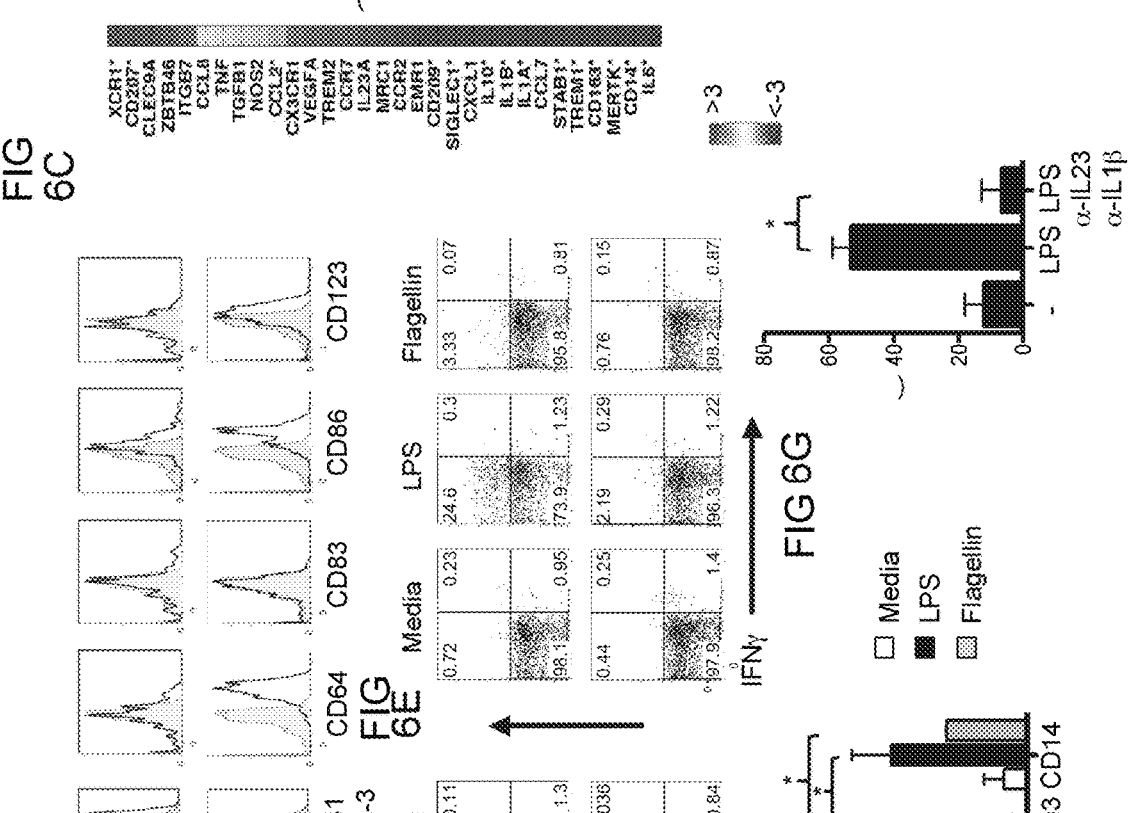
FIG 6B
FIG 6C
FIG 6D
FIG 6E
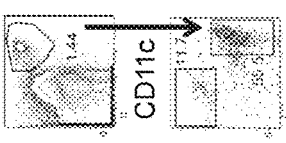
FIG 6F
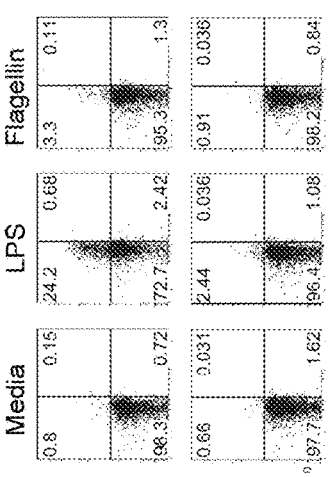
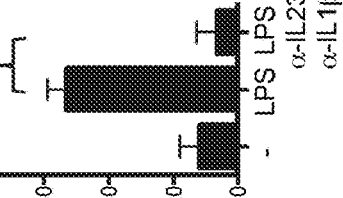
FIG 6G
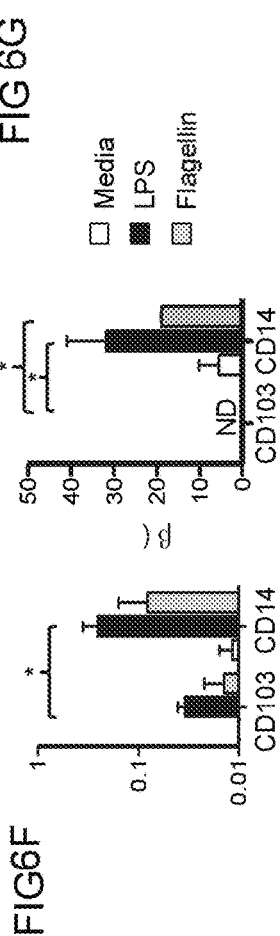

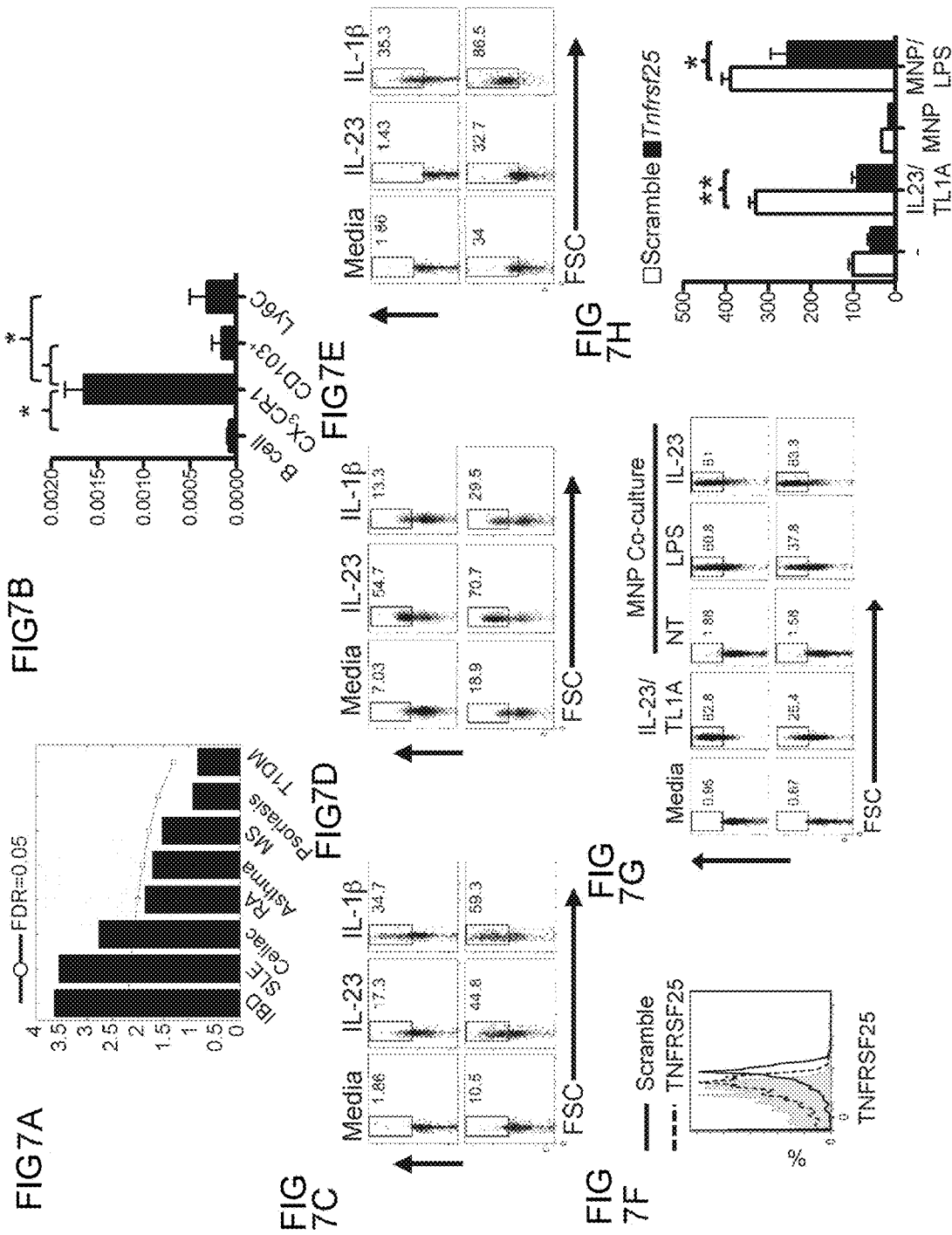

Figure 9A

Homo sapiens tumor necrosis factor (ligand) superfamily, member 15 (TNFSF15), transcript variant 1, mRNA
Accession: NM_005118.3 GI: 324072721 (SEQ ID NO: 1)

```
   1 ggaaaaggga aggaggagac ctctctctgc tgagtgatta agtcacccac tgtgagagct ggtcttctat
  61 ttaatggggg ctctctctgc ccaggagtca gaggtgcctc caggagcagc aggagcatgg
 121 ccgaggatct gggactgagc tttgggaaaa cagccagtgt ggaaatgctg ccagagcacg
 181 gcagctgcag gcccaaggcc aggagcagca gcgcacgctg ggctctcacc tgctgcctgg
 241 tgttgctccc cttccttgca ggactcacca catacctgct tgtcagccag ctccgggccc
 301 agggagaggc ctgtgtgcag ttccaggctc taaaaggaca ggagtttgca ccttcacatc
 361 agcaagttta tgcacctctt agagcagacg gagataaagc aaggcacac ctgacagttg
 421 tgagacaaac tcccacacag cactttaaaa atcagttccc agctctgcac tgggaacatg
 481 aactaggcct ggccttcacc aagaaccgaa tgaactatac caacaaattc ctgctgatcc
 541 cagagtcggg agactacttc atttactccc aggtcacatt ccgtgggatg acctctgagt
 601 gcagtgaaat agacaagca ggccgaccaa acaagccaga ctccatcact gtggtcatca
 661 ccaaggtaac agacagctac cctgagccca ctcagctcct catgggacc aagtctgtat
 721 gcgaagtagg tagcaactgg ttccagccca tctacctcgg agccatgttc tccttgcaag
 781 aagggacaaa gctaatggtg acgtcagtg acatctcttt ggtggattac acaaaagaag
 841 ataaaacctt ctttggagcc ttcttactat aggaggagag caaatatcat tatatgaaag
 901 tcctctgcca ccgagttcct aattttcttt gttcaaatgt aattataacc aggggttttc
 961 ttggggccgg gagtaggggg cattccacag ggacaacggt ttagctatga aatttgggggc
1021 ccaaaattc acacttcatg tgccctactg atgagagtac taactggaaa aaggctgaag
1081 agagcaaata tattattaag atggtttgga ggattggcga gtttctaaat attaagacac
1141 tgatcactaa atgaatggat gatctactcg ggtcaggatt gaaagagaaa tatttcaaca
1201 ccttcctgct atacaatggt caccagtggt ccagttattg ttcaatttga tcataaattt
1261 gcttcaattc aggagctttg aaggaagtcc aaggaaagct ctagaaaca gtataaactt
1321 tcagaggcaa aatccttcac caatttttcc acatactttc atgccttgcc taaaaaaaat
1381 gaaagagag ttgtatgtc tcatgaatgt tcacacagaa ggagttggtt ttcatgtcat
1441 ctacagcata tgagaaaagc taccttttctt ttgattatgt acacagatat ctaaataagg
1501 aagtatgagt ttcacatgta tatcaaaaat acaacagttg cttgtattca gtagagtttt
1561 cttgccacc tattttgtgc tgggttctac cttaaccag aagacactat gaaaaacaag
```

Figure 9A (1)

```
1621  acagactcca ctcaaaattt atatgaacac cactagatac ttcctgatca aacatcagtc
1681  aacatactct aaagaataac tccaagtctt ggccaggcgc agtggctcac acctgtaatc
1741  ccaacacttt gggaggccaa ggtgggtgga tcatcttaag ccggagttc aagaccagcc
1801  tgaccaacgt ggagaaaccc catctctact aaaaatacaa aattagccgg gcgtggtagc
1861  gcatggctgt aatcctggct actcaggagg ccgaggcaga agaattgctt gaactgggga
1921  ggcagaggtt gcggtgagcc cagatcgcgc cattgcactc cagcctgggt aacaagagca
1981  aaactctgtc caaaaaaaaa aaaataaaat aataactcca agcctttaaa aaatatcatc
2041  tgaaactgtt acatcagatt tctggcactc tactgactgt ggaagatagc cagctgactg
2101  gaagatagcc agctgattag ttccctgaag aaacctgaag acagatacct ggttaactag
2161  atcaactaca ctgccaactt gtttgatgct gagagacaat ggacttattc catggggaa
2221  gggaaaaaag aagtcaatca ccaaatctga tattatgtgg ctagatcttt gaggtttgat
2281  ttgcaacttt atatgcagag aagcctagcc gtattttccc ttaaaatatt caaaggatt
2341  tacatatggg attagctaat gagcctagcc aagaccttcc ctggaggaca ggctggtcat
2401  tgcggaggtc ccttctgtgc ttcagtgggt tcatatcctc tagtccgtat gattttccta
2461  cgctaatatg tcaagggcag gagagcagc tctgttctcc tagccttgt tgacttgtct
2521  gcaaagcagg aatctgccca tttgttcca aggagcaaat gagctcatga gaatgaaaga
2581  tgttaacttc atgcattctg tgccatctga gcattcggt attatgac tggtgaccct
2641  tggcccgtat tataaatgct tcctatcctg ggagacctca tggatgagtc tgagagagaa
2701  tttggcacca aaatcactct cactctggtt tccagtagac tatagaggca gagaggcatt
2761  tgagaggctc ctgagcaaag tgtccagtgt agcaggagca cttcattaat atttattgag
2821  ttataattaa ataaaaatta atttctgatt tctcagtttg gaggtaagg ctctaaatat
2881  attttctaac ctctgctagg ctaacttaag ccaggccttt ttcttgcctt cccttttctca
2941  aaacagtcag cacagactca gtgggagcac agaggagtgt ggtcacttcc acctggctca
3001  ccagagtctt catagaggaa gtgaagcctg gaagaaactg gcgggcccc agatgaccac
3061  agggaaaggg catctcagat ggaggaatta ccctgactt aaagcagaaa agaaagattt
3121  ctcagtaact ccaaaacttg cttgatagga gaatattcc tcaaccaatt cctaggacaa
3181  tattiattgg tagatcaaga atgttcctc aataactcta gtctagctcc atgatcagaa
3241  ctaacaccca ttaaaaacat aaaatgttct ttctgaaccg gtcttcatgg tgcgtgagag
3301  caccaagcag ctttgtatg caggaggagt tttgcacaga agagtggcct gctcaaacct
3361  gccactgtt ctgtaggtga tctggtggat ctgaaatttt atcccaagac aggaatttcc
3421  taatattcga agacatttga ggctttggga aattcctctgc tgtcattta tttggctcct
```

Figure 9A (2)

```
3481 gtcataagct tgtttttaa agaatgtatc atagctcaag tttttactgc tgatttttgtt
3541 aaattctgta tagtatattt tttacggaaa ggcacagtca gacattccta ataggctca
3601 tgtcagaact tctgttccca aggcattatc tccatagcaa aaattagtgc actgttttca
3661 aaagtgaggt gggaaaatgc ttttaagatc atgtgatgtt cccctaaaag gggttaatgg
3721 ggtgtattca gggtttggga gggaggaaga agcatgcttt agaaaacagt aaatttaggg
3781 agaaaatgct ttgttggtta aatgtcactc aaaaggctga attcaaatca attccacaaa
3841 catttactga gtacctactg cccctgggga cacagagata aattatttag tctcagacac
3901 actcattcta acttcccagc acctctactg tctgcagatt ctttaattta tttttgttgt
3961 attagctaat taattcgtaa actttaggca catggatcta ttctcattat gaaaatggat
4021 gccatttgat taaggctgat gactaacaaa atgatttgtg tttactcgaa gtgttttttt
4081 aaaaatagct actcaaggat agtttttccat aaatcaagaa ggtaaaaaag ttcccatttt
4141 ttattgtaga atccattatt taaactacat gtagagacag gttattattt gctatattca
4201 agtttggtca tcaatacct taaaaatatt agaattttat ggatgaccca gaaatgcttt
4261 gaaaatctgt gttcctcagc aaatacagag accatgatca aaatgcacag aatcactaac
4321 atttttgatgc tagcatggtt tcagtctatt tggcagaaca gaattgatta tgctactaaa
4381 atttctttt ctttttttt ttttttttt ttgagacaga gtcttgctt gtcaccagg
4441 ctgaagtgca gtggcaggat ctcagttcac gcaacctct gcctcccagg ttcacgccat
4501 tctcctgcct cagcctcccg agtagctggg actacaggct ccaccacca tgcccggcta
4561 ttttttgca ttttagtag agacgggtt tcaccgtgtt agccaggatg gtctcgatct
4621 cctgacctcg tgatccgccc gcctcagcct tttttttac tccaaagtgc tgggattaca ggcgtgagcc
4681 actgtgcccg gactctgatt tttttttac taaggtacag taagaaaagg gaaaagtgta
4741 cgttttcact tcctgaaata tgtcaggttg aatcaataat agagcacacc agaactcttg
4801 gctccatttc aacctaaact attcagttct catcacccca gaggaaattc cgcctctgtg
4861 ctggtcagta atccccctgg attataaaag tttaactaac tcactgtgca caaggcagg
4921 ccattgccaa catctcttg caaggtattt tccagccc ttaccaatt ctgtttccat
4981 gattgtgaca ttgggatta atctgcaag acagaactgt ttatattctg tacctaaaa
5041 acacatgcaa acatctcttg ccttaagatt tctggcttc ctatggccca gagtcctaga
5101 agtgttttga tatttgtagc agaatttca agtgtacatc cttatcctgg atattaacat
5161 ttttgcatca tattggcagc tggacctaca gagaatttag tagactgtta acctaataag
5221 ccttgaatcc ttttgcacca gtggtgagag aatgtggatc agagccatca cctccatgcc
5281 ccgtcaccct ctaacaacca catttacaac ttccccagct ctgagacaca cttgcctcca
```

Figure 9A (3)

```
5341 cccttccat cacccatt taagatgaaa ataccacacc agcctggaag gaagaagtta
5401 cttgccagg gccacatagt gagttaaggg ctgatctaga gctaggaagc tgtcttcctg
5461 aaccataatc ctgactctt ctaacctctc tactcatcgc aaatagagtt cattttagtg
5521 atttgaagga agatggaca agtatttca aacacctgta ggacaacatg gaagtggag
5581 gagacttcta ctgtagctcc ccagagaaga gagctagggc tacagagttg cagttacaag
5641 gttgccctct ctggcttgat ccccaaagga attttctact ccaaaataga atttttctag
5701 gatgctattt ctcagtccct ggagatactc aaacaaaggg cttgtcacaa gggttttgt
5761 agaagctatt cttcacagag gttggggag agattaagcc aaaggatctc tgaggtctt
5821 ttcaaatcta taattatgtg gccttttgtt cattgacttc catgtgttct agttgatcat
5881 tacaaacctg gcaggccttc tcaagggttc agtaattagc tgtcattcc cattgtcca
5941 gagagtgtcc aacacaaaat accctaaga tcttggcaa tagagaaatg tcatgaatt
6001 ttagaaatga cagtatctgc ggagttatt ccaagttata tcatttcaaa gatgaagaaa
6061 cccaggctca gaggagcca tcacatccac accctgtcac ccttcgtggc cagtgccaga
6121 cagtagctag ttggatgcta aaagtagaat ttagatatct taacaataag cccagcagtc
6181 tttcaacttc attcgtaaat cattttgtt ttgagcatct gtcacgtggc agcacttgcc
6241 tggatactgg agagctgaga aggaatgcga caggcaagtg ctactctcac agtgtataca
6301 ttcaggagga acaagacaca cagtgccaag taaataaagt agctgaactt catcaaatga
6361 tttattctt aaagtcatta agcatggaa tgttccctt ttttgtttc aggggtgtac
6421 agattgaaga agtgtaggtg tttatgtggt tttagtgaca aacccatgt gctttcattg
6481 atttatgtt ttattgttaaa acatcaaccg caagtaaaa tgcatattgt atgttgttgg
6541 atacgtactt aactggtatg catcccatgt ctttgggtac tagtgtatga attctaatct
6601 ctgtaaatga aatgttgtat gtgttaatat atttaataga tgtaacttaa taaactgca
6661 ttgaagactg aagaattttc acactgtcaa acaaaaaaaa aaaaa
```

Figure 9B

Homo sapiens tumor necrosis factor (ligand) superfamily, member 15 (TNFSF15), transcript variant 2, mRNA
NCBI Reference Sequence: NM_001204344.1 (SEQ ID NO: 2)

```
   1 atgcaactca caaagggccg tctttcatttc agtcaccctt tgtctcatac aaagcacatt
  61 tctcctttg ttacagatgc acctcttaga gcagacggag ataagccaag ggcacacctg
 121 acagttgtga gacaaactcc cacacagcac tttaaaaatc agttcccagc tctgcactgg
 181 gaacatgaac taggcctggc cttcaccaag accgaatga actataccaa caaattcctg
 241 ctgatcccag agtcgggaga ctactttcatt tactcccagg tcacattccg tgggatgacc
 301 tctgagtgca gtgaaatcag acaagcaggc acaagcaggc cgaccaaaca agccagactc catcactgtg
 361 gtcattcacca agtaacaga cagctaccct gagccaaccc agtcctcat gggaccaag
 421 tctgtatgcg aagtaggtag caactgttc cagcccatct acctcggagc catgttctcc
 481 ttgcaagaag gggacaagct aatggtgaac gtcagtgaca tctcttttggt ggattacaca
 541 aaagaagata aaacctttctt tggagcctttc ttactatagg aggagagcaa atatcattat
 601 atgaaagtcc tctgccaccg agttcctaat tttcttttgtt caaatgtaat tataaccagg
 661 ggttttcttg gggccgggag tagggggcat tccacaggga caacgttta gctatgaaat
 721 ttgggccca aaattcaca cttcatgtgc cttactgatg agagtactaa ctggaaaaag
 781 gctgaagaga gcaaatatat tattaagatg ggttggagga ttggcgagtt tctaaatatt
 841 aagacactga tcactaaatg aatggatgat ctactcgggt caggattgaa agagaaatat
 901 ttcaacacct tcctgctata caatggtcac cagtggtcca gttattgttc aatttgatca
 961 taaattttgct tcaattcagg agctttgaag gaagtccaag gaaagctcta gaaaacagta
1021 taaactttca gaggcaaaat ccttcaccaa tttttccaca tactttcatg cctttgcctaa
1081 aaaaaatgaa aagagagttg gtatgtctca tgaatgttca cacagaagga gttggttttc
1141 atgtcatcta cagcatatga gaaaagctac ctttcttttg attatgtaca cagatatcta
1201 aataaggaag tatgagtttc acatgtatat caaaaataca acagttgctt gtattcagta
1261 gagttttctt gcccacctat ttttgtctgg gttctacctt aaccagaag acactatgaa
1321 aaacaagaca gactccactc aaaattata tgaacaccac tagatacttc ctgatcaaac
1381 atcagtcaac atactctaaa gaataactcc aagtcttggc caggccagt ggctcacacc
1441 tgtaatccca cactttggg aggccaagt gggtggatca tctaaggccg ggagttcaag
1501 accagcctga ccaagtgga gaaaccccat ctctactaaa aatacaaaat tagccgggcg
1561 tggtagcgca tggctgtaat cctggctact caggaggccg aggcagaaga attgcttgaa
```

Figure 9B (1)

```
1621 ctggggaggc agaggtttgcg gtgagcccag atcgcgccat tgcactccag cctgggtaac
1681 aagagcaaaa ctctgtccaa aaaaaaaaaa ataaaataat aactccaagc ctttaaaaaa
1741 tatcatctga aactgttaca tcagatttct ggcactctac tgactgtgga agatagccag
1801 ctgactgaa gatagccagc tgattagttc cctgaagaaa cctgaagaca gataccggt
1861 taactagatc aactacactg ccaacttgtt tgatgctgag agacaatgga cttattccat
1921 ggggaaggg aaaaaagaag tcaatcacca aatctgaaga agttaaccta gatctttgag
1981 gtttgatttg caacttata tgcagagtat tatgtgggta tttccctta aaatattcaa
2041 agggattac atatgggatt agctaatgag cctagccaag acctttcctg gaggacaggc
2101 tggtcattgc ggagtccct tctgtgcttc agtgggttca tatcctctag tccgtatgat
2161 tttcctacgc taatatgtca agggcaggag agcagctct gttccaagg ctttgttga
2221 cttgtctgca aagcaggaat ctgcccattt gttccaagg agcaaatgag ctcatgagaa
2281 tgaaagatgt taacttcatg cattctgtgc cattgcca tttcggtatt atatgactgg
2341 tgacccttgg cccgtattat aaatgcttcc tatcctggga gacctcatgg atgagtctga
2401 gaggaaattt ggcaccaaaa tcactctcac tctgtttcc agtagactat agaggcagag
2461 aggcattga gaggctcctg agcaaagtgt ccagtgtagc aggagcactt cattaatatt
2521 tattgagtta taattaaata aaaattaatt tctgatttct cagtttgag gttaaggctc
2581 taaatatatt ttctaaccto tgctaggcta acttaagcca ggcctttttc ttgccttccc
2641 tttctcaaaa cagtcagtg agactcagtg ggagcacaga ggagtgtggt cacctccacc
2701 tggctcacca gagtcttcat agaggaagtg aagcctggaa gaaactgggc gggcccccaga
2761 tgaccacaga gaaaggcat ctcagatgga ggaattaccc ttgacttaaa gcagaaaaga
2821 aagatttctc agtaactcca aaacttgctt gataggagaa tatttccctca accaatttct
2881 aggacaatat ttattggtag atcaagaatg tttcctcaat atgttcttttc tgaaccggtc tagctccatg
2941 atcagaacta acacccatta aaaacatata gaggagttt gcacagaaga gtgcctgct
3001 gtgagagcac caagcagctt tggtatgcag ggtggatctg gaaattatc ccaagacagg
3061 caaacctgcc cactgttctg taggtgatct tttgggaaat tctctgctgt gcattattt
3121 aatttcctaa tattcgaaga catttgaggc ttttaaaga atgtatcata gctcaagttt ttactgctga
3181 ggctcctgtc ataagcttgt tttttgttt tatatttttt acggaaaggc acagtcagac attcctaata
3241 tttttgttaaa ttctgtatag cagaacttct gttccaagg cattatctcc atagcaaaaa ttagtgcact
3301 gggctcatgt cagaacttct cagaacttct gttcccaagg cattatctcc atagcaaaaa ttagtgcact
3361 gttttcaaaa gtgaggtggg aaaatgcttt taagatcatg tgatgttccc ctaaaagggg
3421 ttaatgggt gtattcaggg tttgggaggg aggaagaagc atgctttaga aacagtaaa
```

Figure 9B (2)

```
3481 tttagggaga aaatgctttg ttggtttaaat gtcactcaaa aggctgaatt caaatcaatt
3541 ccacaaacat ttactgagta cctactgccc ctgggacac agagataaat tatttagtct
3601 cagacacact cattctaact tccagcacc tctactgtct gcagattctt taatttattt
3661 tggttgtatt agctaattaa ttcgtaaact ttaggcacat ggatctattc tcattatgaa
3721 aatggatgcc atttgattaa ggctgatgac taacaaaatg atttgtgttt actcgaagtg
3781 tttttttaaa aatagctact caaggatagt tttccataaa tcaagaaggt aaaaagttc
3841 ccattttta ttgtagaato cattatttaa actacatgta gagacaggtt attatttgct
3901 atattcaagt ttggtcatca ataccettaa aaatattaga atttatgga tgacccagaa
3961 atgctttgaa aatctgtgtt cctcagcaaa tacagagacc atgatcaaaa tgcacagaat
4021 cactaacatt ttgatgctag catgtttca gtctatttgg cagaacagaa ttgcttatgc
4081 tactaaaatt tctttttctt ttttttttt tttttttg agacagagtc ttgcttgtc
4141 acccaggctg aagtgcagtg gcaggatctc agttcactgc aacctctgcc tcccaggttc
4201 acgccattct cctgcttcag cctcccgagt agctgggact acaggctccc accaccatgc
4261 ccggctaatt ttttgcattt ttagtagaga cggggttca ccgtgttagc caggatggtc
4321 tcgatctcct gacctcgtga tcgcccgcc tcagcctcc aaagtgctgg gattacaggc
4381 gtgagccact gtgcccggac tctgattttt ttttttactaa ggtacagtaa gaaaagggaa
4441 aagtgtacgt tttcacttcc tgaaatatgt caggttgaat caataataga gcacaccaga
4501 actcttggct ccatttcaac ctaaactatt cagttctcat cagtctctg gaaattccgc
4561 ctctgtgctg gtcagtaato cccctgatt ataaaagttt aactaactca ctgtgcacaa
4621 ggcacggcca ttgccaacat tctcttgcaa ggtatttcc caagcccttta cccaattctg
4681 tttccatgat tgtgacattg gggattaatt ctgcaagaca gaactgttta tattctgtac
4741 cttaaaaaca catgcaaaca tctctttgct taagatttct ggcttcota tggcccagag
4801 tcctagaagt gttttgatat ttgtagcaga attttcaagt gtacatcctt atcctggata
4861 ttaacatttt tgcatcatat tggcagctgg acctacagag aatttagtag actgttaacc
4921 taataagcct tgaatccttt tgcaccagtg gtgagagaat gtggatcaga gccatcacct
4981 ccatgccccg tcaccctcta acaaccacat ttacaacttc ccagctctg agacacactt
5041 gcctccaccc cttccatcac cccatttaa gatgaaaata ccaccacagc ctggaaggaa
5101 gaagttactt gcccagggcc acatagtgag ttaagggctg atctagagct aggaagctgt
5161 cttcctgaac cataatcctg gactcttcta acctctctac tcatgcaaa tagagttcat
5221 tttagtgatt tgaaggaaca tgggacaagt attttcaaac acctgtagga caacatgaa
5281 gtgggaggag acttctactg tagctcccca gagaagagag ctaggctac agagttgcag
```

Figure 9B (3)

```
5341 ttacaaggtt gccctctctg gcttgatccc caaaggaatt ttctactcca aaatagaatt
5401 tttctaggat gctattctc agtccctgga gatactcaaa caaagggctt gtcacaaggg
5461 ttttgtaga agctattctt cacagaggtt ggggagaga ttaagccaaa ggatctctga
5521 ggtctttttc aaatctataa ttatgtggcc tttgttcat tgacttccat gtgttctagt
5581 tgatcattac aaacctggca ggccttctca agggttcagt aattagctgt catttcccat
5641 ttgtccagag agtgtccaaac acaaaatacc cctaagatct tggccaatag agaaatgtca
5701 tggaatttta gaaatgacag tatctgcgga gtttattcca agttatatca tttcaaagat
5761 gaagaaaccc aggctcagag ggagccatca catccacacc ctgtcaccct tcgtggccag
5821 tgccagacag tagctagttg gatgctaaaa gtagaattta gatatcttaa caataagccc
5881 agcagtcttt caacttcatt cgtaaatcat tttgttttg agcatctgtc acgtggcagc
5941 acttgcctgg atactggaga gctgagaagg aatgcgacag gcaagtccta ctctcacagt
6001 gtatacattc aggaggaaca agacacacag tgccaagtaa ataaagtagc tgaacttcat
6061 caaatgattt tattcttaaa gtcattaaag catgtaatgt tcccttttt ttgtttcagg
6121 ggtgtacaga ttgaagaagt gtaggtgttt atgtggtttt agtgacaaac cccatgtgct
6181 ttcattgatt ttatgtttta tgttaaaaca tcaaccgcaa ggtaaaatgc atattgtatg
6241 ttgtttggata cgtacttaac tggtatgcat cccatgtctt tgggtactag tgtatgaatt
6301 ctaatctctg taaatgaaat gttgtatgtg ttaatatatt taatagatgt aacttaataa
6361 actggcattg aagactgaag aatttttcaca ctgtcaaaaa aaaaaaaaaa aa
```

Figure 9C

Tumor necrosis factor (ligand) superfamily, member 15 [Homo sapiens]
GenBank: AAI04464.1 (SEQ ID NO: 3)

```
  1 maedlglsfg etasvemlpe hgscrpkars ssarwaltcc lvllpflagl ttylivsqlr
 61 aggeacvqfq alkggefaps hqqvyaplra dgdkprahlt vvrqtpqhf knqfpalhwe
121 helglaftkn rmnytnkfll ipesgdyfiy sqvtfrgmts ecseirqagr pnkpdsitvv
181 itkvtdsype ptqllmgtks vcevgsnwfq piylgamfsl qegdklmvnv sdisivdytk
241 edktffgafl l
```

Figure 9D

Mus musculus tumor necrosis factor (ligand) superfamily, member 15 (Tnfsf15), mRNA
Accession: NM_177371.3 GI: 238776818 (SEQ ID NO: 4)

```
   1 actcagtgtg acagctgctc tcttatttaa tggggggctc tctggtcaga agggatcaga
  61 agtctctcca agacagcaga aggatggcag aggagctggg gttgggcttc ggagaaggag
 121 tcccagtgga agtgctgccg gaaggctgta gacacaggcc agaggccagg gccgggctag
 181 ctgccaggag caaagcctgc ctggctctca cctgctgcct gttgtcattt cccatcctcg
 241 caggacttag cacccctcta atggctggcc agctcgggt ctcaccaca gactgtatgc
 301 ttcggggccat aacagaagag agatctgagc cttcaccaca gcaagtttac tcacctccca
 361 gaggcaagcc gagagcacac ctgacaatta agaaacaaac cccagcacca catctgaaaa
 421 atcagctctc tgctctacac tgggaacatg acctagggat ggccttcacc aagaacggga
 481 tgaagtacat caacaaatcc ctgtgatcc cagagtcagg agactatttc atctactccc
 541 agatcacatt ccgagggacc acatctgtgt gtggtgacat cagtcggggg agacgaccaa
 601 acaagccaga ctccatcacc atggttatca ccaaggtagc acagctac cctgagcctg
 661 cccgcctact aacaggtcc aagtctgtgt gtgaaataag caacaactgg ttccagtccc
 721 tctacccttg ggccacgttc tccttggaag aaggagacag actaatggta aacgtcagtg
 781 acatctcctt ggtgattac acaaagaag ataaacttt cttgagct ttcttgctat
 841 aaggaggaga aaaccatcat tccaaggggc tcccctgcct cctactttcc aatttccttt
 901 tctcatatgg atctataaac aggcttta gagggatcag ggaaggggac agtggtttag
 961 ctatataatt taggaaccca atattgatcc gtatatgcct tatggactaa aatagtaaat
1021 ggaaaaccca gtacagctca tgtttgatag agacctgctg ggtttttaaaa attgaaacac
1081 gcctcatcca atggcacaat ctactgattt caggacagaa cctttccaca gtgccctctg
1141 tccaagtcct ttctgaattc agcagttcag ttagagctga attcgacaat gaacttactc
1201 cagatcaaga gctaaagaca gaatccaaag aaagactgag aaaatgatgt tatttctcca
1261 agaggcaatg catttccaca ttcttttgtg cctaacctaa aaaataagaa agaagaaagg
1321 aaggaaggaa ggaaggaaaggg aaggaaggaa ggaaggaagg aaggaaggaa ggaaggaagg
1381 aaggaaggga caagaaaaga caagacaaga caagaaaaaa gaaaaaaatg tatttctcgt
1441 gaatattccc taaaaggaat tggttttctg ctgtgaagga gaaacctcac ctttctttctg
1501 attgcatcct ttagtatcca aacatacaag tggaattcc aatgcacat ggaacataga
1561 acactttat tattgtgaga acatgttat tgagtaccta ctatgctctg ggcactcagc
```

Figure 9D (1)

```
1621  ccacaggacc atgaagagaa agtcaaattt tcttaaaaac taaatgaatc ctcaatacat
1681  acttcctgat caactaccac tcaaaatgta taacttccaa agtataactt caagtcagcc
1741  atctaggtgg tttcttgggt aaaggtgctt gtcattaagc ctgacacctg ggtttgacct
1801  cccagaaccc aaaagctgga aggagagaat tggttcccac aaattatcct caaaccccca
1861  tacaaatgat gtggcatgca cacatgtaac taaataaata agtgtaaaac aaaaacaaaa
1921  acaaaatttt aagaaaaaat ttcaagtcct gaaagacagc attcctgaga atgttgtctc
1981  catcgttgtc cagtataggc taaccagctg atagagacac tgaaggaatt taaagacaga
2041  catcaagtga aatggagcac tgtagaaaca cttgattcat gccaggagtc aatgtactat
2101  gaagaccaac aacaaagtgt cagtcatcaa atccagaggt gtttatctag atctgctttc
2161  aagtttggtt tgcagccttt atatagtctc tattacaaat gctcgtgtca tgtagatgc
2221  cacaaggagt cagagggtaa acttagcccc aaaccactgc tgagccatct tctaggaaac
2281  cttcgaagca gagctgggca gcgtgactcc cacacaatga ctgggaaagt agtagctgat
2341  caaaatttgt tgagtaataa tttgttagaa aattcatctc cactgcctac taaacctaag
2401  ttgtatacta tctagcttct gctaagccaa cttacattgg ccacttttc tgtcttcaac
2461  ttcttgaagt atcacagtc tcagtgagaa cacaggaaa ggtgaggtcg ccttcccctg
2521  gttcttcata gggaaaacca cacctgaaag aagatgagca gcctgaggtg acctggagga
2581  agggctgtct cagaagaagg acttatttt tggcttaggt ctaaaacctt gagagtaatg
2641  ctcactggtc aattgaggat gcttatcaa tgactccagt ctgactccaa ggtcagaaag
2701  gagagtgaga tgctctctct gcctgcatat atctttcatgg aacatgagaa tattgacaa
2761  catagactta taggaaaaca cttgcccaaa agtagccaga gtgacctggt catcccctct
2821  actaaaccca agcttttgtt caagggcctt caaagctgcc cagaagtgat ctggatggct
2881  tggaaattta tccaagacag gaatttcctg acagccaaag atgcttgagt cctttgtcct
2941  gacatgcatt tattttgccc ctgtttattg aagactgtaa ctgttgattt gtgggtatac
3001  atacatacat acatacatac atacatacat acatacatat gctgtcatga aggcagcatc
3061  aacattact aattggactc aaaccagcac ttctgttttcc aagatactaa gtattccat
3121  gcaaacagga gcatgctatt tttctaaagc aaaatgaaaa aaatagtttt gaaagtatat
3181  atatgatgga gtcaagtgta atgcataca tctgtaaacc cagcacatgg gatgctgagc
3241  caggaggatt gccgtgagtt tgaggagaac agggctaaa tagtaattt caggaaagcc
3301  ttgcctatat aacaagacct tgtctcaaat gaaaaaaaaa aaaaaaatag accccaggct
3361  ggtccttgga gataaggtaa tatattcatt gggtgagggg gtgtgtgttt tggaaaatag
3421  ttaatttagt gagaaatgct tttcggtcaa atgcatctca aaggctgctg aattcaaatc
```

Figure 9D (2)

```
3481 gggtctgtaa atgcttacct agtgctgct tgccctgggg acagagacat aaattacttt
3541 agtctcagat ccactcgttc taacagattg gcatctccat cgtctgtgga gcttttaatc
3601 actctgtttg tattagctaa ttaattagct aacttgagac acactgatat tttcttatta
3661 taaacatggg tgccatttga taaaagacaa tcattaacaa aatggttcga atttccgctt
3721 aagtgatctt ctttttttcct tttcattttt tttaactagc taatcaaagg tagttttccca
3781 aaaataaatg caaagggagt ataaagaaaa aatttccctgt ggtgggagct agtatttgaaa
3841 caacagtatc aaagaggctg ttacctactg gcctcaaatt ttggcaggaa cgcctttgaa
3901 aatgttagaa ctttacggac agcctagagg tgctttgaaa agtctctgtt gcaaacaaaa
3961 gccattaatc agcatgcggc acaggttact caaattttga ccttgactgt tttttagatc
4021 tgttacacag aacacaactt ctgggctgta atctctgatg tggatttggt gatttactaa
4081 ggtacgtgg gaaacaagga aagtgtactt gtaccacatc gtttctcagt gcatgtcaga
4141 gtctactcaa cagcagggca tgccagagcc ttggatacat tccggacaa actatgtcac
4201 tcctaaggaa attccaagtg tgtgcctgtc aagcactctg gatcatagaa gcccacgagt
4261 tcactgtgca caaggcacag ccatggccag cactctcttg catgtatttt ctcttaagct
4321 cttactcaat cacgtccca tgattgtgac attgggggtt aattgcttga gcaggtttat
4381 ttacagtctg ttccttgcaa aatacatgca gatatgtctg gcctcaaaat cccctgattg
4441 ttttagggct tagagaatac tggggatgtt tttgctgttt tcagatgtac tttattaag
4501 cttgcagaat taccctgaat attaacagtg ttctaagata ttgcctgcta gcttctgct
4561 aatttactag tggtgacagt atcagatcag agtatctata tttatgtctt gctattatag
4621 ttaaacttc ctgatctctg taacacactc accctacct catctatcta ccatcttgt
4681 ggatgtagct gtgagaagac tcacaagccc gagttgcagt tactttcctg aagcaacata
4741 gtatgttaat ggaatggcca gaactctact cttggcacat ggcactgaat ttgatgccac
4801 taaaagaaaa attgaaggca gaaatatttt ttactatgca tgggacaacg tagaagagca
4861 aggagactgc ttacacatgg tggtcacatc tctggcttca tccctaaacc aatttctga
4921 ccccaagtcg atttttttttc atgtagttat tgttcatttt ctgaaaagag gccaaagaat
4981 agagagttt ataaaacca ttgcatcatg gaggtcaggg tacttctatt tgatcatgac
5041 tccttctcca aatctatagc catatggcca cccttgtttg ctgcttatt ggattcatt
5101 aaacctgaga gccctgccca gagttcagtg gatcctaatg aactccaaga gtaattcatt
5161 ccctcaccaa ctctagggc ttggccagtg cagaaaatgt catgggattt taaagttaac
5221 atgagctgct atccaaactt atgtctcttt aagaatggag agacacaggc caggagaggt
5281 aacatatgaa gcctgtatt gggcagtagc ttgatggagt attgaggcta aaagtagact
```

Figure 9D (3)

```
5341 tcctgcccct gaccatacac aacacccttt cagtttgatc catggtggtc ttattctact
5401 ttattttgag cacctgtcac acctagttac tgtcatgcca agaaggtcca taacaggcaa
5461 atcctactct gctgtgtgca cacaagagga aggaggctca cagtagcaag taaacagata
5521 agcaaacgta cacgattttc gtcttaaagt cattaagaca cacgcgtacc cctcttttgt
5581 ttcagagggt atacaggctg aacagatgtc agtgttcacc tattcttatt gataagcccc
5641 atgtgctttc attggtttga tgtttttatgt taaaacgtca tattgccatc gtaaaatgca
5701 tattgtatgt tgttgggtat ataattaact aatatgcatc gcatgtatga attctaatct
5761 ctgtaaaatga aaacttatat atgttaacat atgtaatagt tataatttaa taaactgaca
5821 ctggagac
```

Figure 9E

Tumor necrosis factor ligand superfamily member 15 [Mus musculus]

NCBI Reference Sequence: NP_796345.3 (SEQ ID NO: 5)

```
  1 mggslvrrdq kslqdsrrma eelglgfgeg vpvevlpegc rhrpearagl aarskaclal
 61 tcclisfpil agistlimag qlrvpgkdcm lraiteerse pspqqvyspp rgkprahlti
121 kkqtpaphlk nqlsalhweh dlgmaftkng mkyinkslvi pesgdyfiys qitfrgttsv
181 cgdisrgrrp nkpdsitmvi tkvadsypep arlitgsksv ceisnnwfqs lylgatfsie
241 egdrimvnvs dislvdytke dktffgafil
```

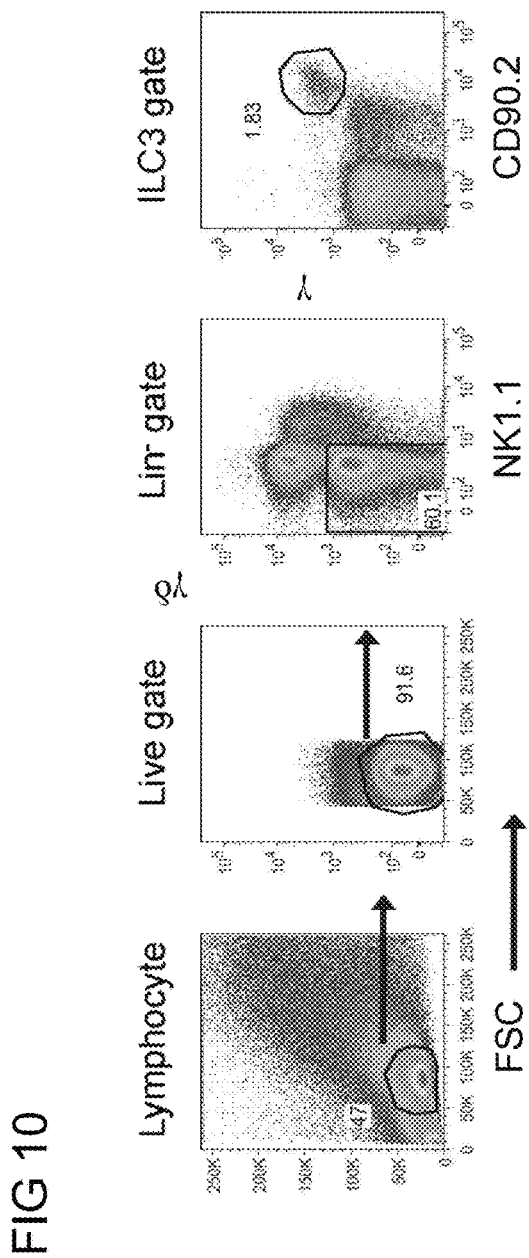

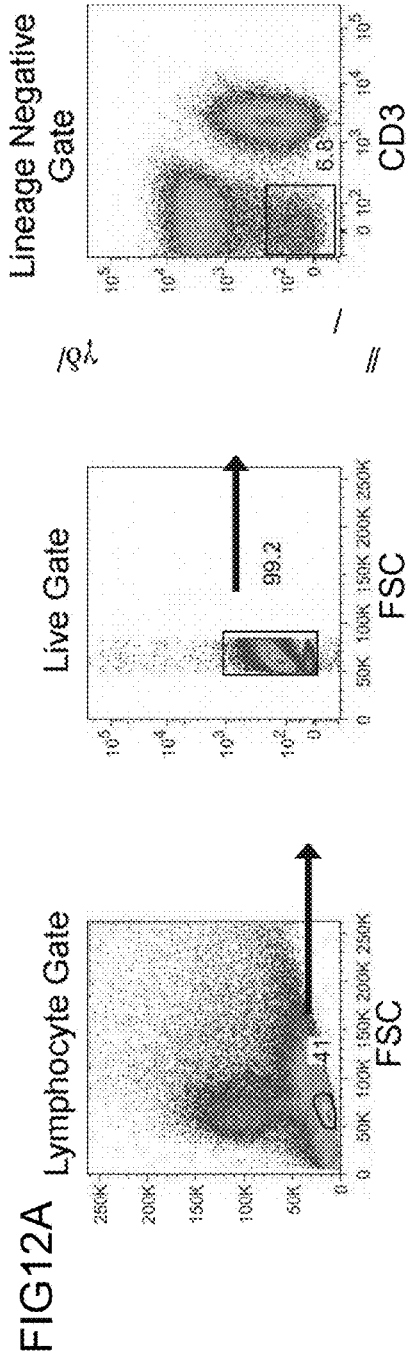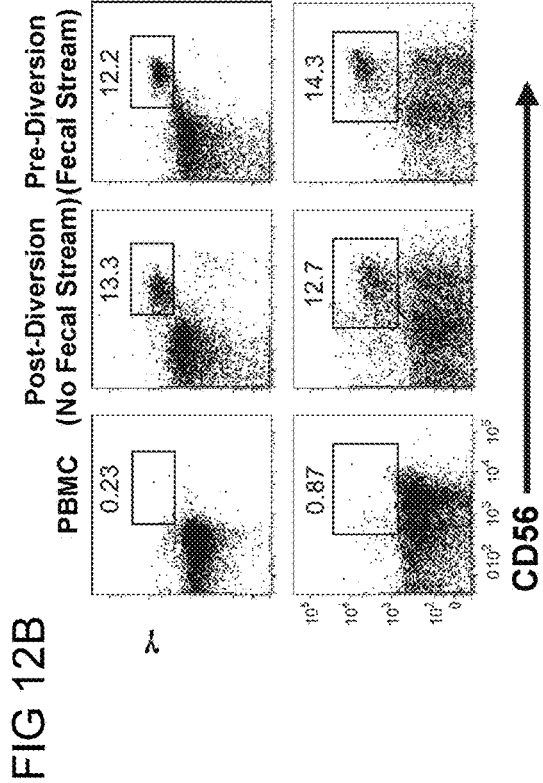

FIG 14

| Patient ID | Disease | Age | Medication | Endoscopic Evaluation | Disease Location |
|---|---|---|---|---|---|
| 1 | CD | 65 | None | Mild | Ileum, Colon |
| 2 | UC | 22 | None | Mild | Rectum to Descending Colon |
| 3 | UC | 52 | Mesalamine | Mild | Rectum to Descending Colon |
| 4 | UC | 64 | Mesalamine | Mild | Rectum to Descending Colon |
| 5 | UC | 27 | Mesalamine/6-MP | Moderate | Entire Colon |
| 6 | CD | 55 | None | Moderate | Segmental Colitis |
| 7 | CD | 29 | None | Mild | Ileum, Colon |
| 8 | CD | 57 | None | Mild - moderate | Entire Colon |
| 9 | CD | 24 | Mesalamine | Moderate | Ileum, Colon |
| 10 | UC | 34 | Anti-TNFα | Mild | Rectum to Descending Colon |
| 11 | CD | 27 | Mesalamine | Mild | Entire Colon |
| 12 | UC | 27 | Steroids | Mild | Entire Colon |
| 13 | UC | 28 | Mesalamine | Mild | Rectum to Distal Transverse |
| 14 | CD | 28 | None | Mild | Ileum, Colon |

METHODS OF TREATING INFLAMMATORY BOWEL DISEASE BY ADMINISTERING TUMOR NECROSIS FACTOR-LIKE LIGAND 1A OR AN AGONISTIC DEATH-DOMAIN RECEPTOR 3 ANTIBODY

CROSS REFERENCE TO RELATED APPLICATION

This application claims priority under 35 USC § 119(e) from U.S. Provisional Application Ser. No. 62/023,816, filed Jul. 11, 2014, which application is herein specifically incorporated by reference in its entirety.

GOVERNMENT RIGHTS

The research leading to the present invention was funded in part by grant number K08 DK099381 from the National Institute of Health. The United States government has certain rights in the invention.

BACKGROUND OF THE INVENTION

Inflammatory bowel disease (IBD) involves a dysregulated cellular immune response to environmental triggers in genetically predisposed individuals. IBD is a general term used for a group of disorders that cause intestinal mucosa to become inflamed. This can become a chronic condition and may lead to cancer. Examples of such inflammatory bowel diseases include Crohn's disease and ulcerative colitis (UC). Crohn's disease predominantly affects the ileum and colon, although it is also seen in other sections of the gastrointestinal (GI) tract. UC, on the other hand, generally manifests as an inflammation of the colon. It is considered that IBD results in disruption of the continued renewal of the mucosal lining of the GI tract.

The citation of references herein shall not be construed as an admission that such is prior art to the present invention.

SUMMARY OF THE INVENTION

The present disclosure provides compositions and methods for mucosal healing of the GI tract. The methods and compositions are based on our work which identifies a cell population critical for regulating interleukin (IL)-22-producing group 3 innate lymphoid cells (ILC3) in colitis. We employed novel mouse models to enable selective depletion of $CX_3CR1^+$ mononuclear phagocytes (MNPs) in vivo. Our results reveal a critical role for $CX_3CR1^+$ MNPs from both mouse and human tissue in supporting IL-22 induction in ILC3 in vitro and in vivo. Moreover, we identify the ability of TNF-like ligand 1A (TL1A) produced by MNPs to potently enhance IL-23- and IL-1β-induced production of IL-22 and granulocyte macrophage colony stimulating factor (GM-CSF) by ILC3. The present method utilizes therapeutic manipulation of $CX_3CR1^+$ MNP function and/or events downstream to promote ILC3 production of IL-22.

In one aspect, the present disclosure provides a method for stimulating GI tract mucosal healing by administration to an individual a composition comprising agents that induce ILC3 to produce IL-22. In one embodiment, the agent is TL1A (also known as TNFSF15). In another embodiment, the agent is a molecule that activates the receptor for TL1A—such as, for example, an agonist antibody to the death-domain receptor 3 (DR3; also known as TNFRSF25). In another embodiment, the agent for inducing ILC3 to provide IL-22 stimulates $CX_3CR1^+$ MNPs. In one embodiment, the agent is a composition comprising one or more types of microbes found in fecal microbiota. In another embodiment, the fecal microbiota is human fecal microbiota. In yet another embodiment, the agent induces ILC3 to produce IL-22 and GM-CSF.

In a particular embodiment thereof, the composition comprises a sterile manmade physiologically compatible carrier or excipient that is compatible with oral and/or anal administration. Exemplary buffers compatible with oral administration include sterile manmade solutions that are physiologically compatible such as, for example, sterile normal saline or a sterile saline-based gelatin or matrix. Normal saline is typically defined as a solution of 0.90% weight/volume of NaCl, about 300 mOsm/L or about 9.0 grams NaCl per liter of water. In a particular embodiment, oral administration is achieved using an encapsulated means, wherein the capsule is designed to dissolve or disintegrate in the small and/or large intestine. Exemplary buffers compatible with anal administration comprise sterile manmade solutions that are physiologically compatible such as, for example, normal saline, saline-based gelatin, oleaginous (fatty) bases [e.g., theobroma oil (cocoa butter) and synthetic triglycerides], and water soluble or miscible bases (e.g., glycerinated gelatin and polyethylene glycol polymers).

In another embodiment, a method for treating a subject afflicted with an inflammatory bowel disease (IBD) is presented, the method comprising administering to the subject a therapeutically effective amount of tumor necrosis factor like ligand 1A (TL1A) or an agent that activates death-domain receptor 3 (DR3) or a composition thereof, wherein administering the TL1A or the agent that activates the DR3 or the composition thereof promotes mucosal healing, thereby treating the subject afflicted with IBD. In a particular embodiment thereof, the TL1A is recombinant, manmade TL1A. In another particular embodiment, the agent that activates DR3 is a recombinant, manmade agent. In a further embodiment, the IBD is Crohn's Disease (CD), ulcerative colitis (UC), collagenous colitis, lymphocytic colitis, ischaemic colitis, diversion colitis, Behcet's disease, or indeterminate colitis. In a more particular embodiment, the IBD is CD or UC. In an embodiment thereof, the agent that activates DR3 is an agonistic DR3 antibody or a receptor binding fragment thereof. Compositions described herein may be formulated for oral or rectal delivery. In a more particular embodiment, the composition formulated for oral delivery is formulated to release the TL1A or the agent that activates DR3 in the subject's small or large intestine. In a still more particular embodiment, the composition is formulated to release the TL1A or the agent that activates DR3 at a pH characteristic of the small intestine, such as, for example, a pH of about pH 6.0. In another particular embodiment, the composition is formulated to release the TL1A or the agent that activates DR3 at a pH characteristic of the large intestine, such as, for example, a pH of about pH 7.0. In a particular embodiment, the subject is a mammal, for example, a mouse, rat, or primate. In a more particular embodiment, the subject is a human.

In another embodiment, a method for screening to identify an activator of mononuclear phagocytes (MNPs) is presented, the method comprising contacting a population of $CX_3CR1^+$ MNPs with at least one candidate modulator agent; and detecting expression of Interleukin-23 (IL-23) in the presence of the candidate modulator agent and comparing that to expression of IL-23 in the absence of the candidate modulator agent, wherein an increase in expression of Interleukin-23 (IL-23) in the presence of the candidate modulator agent relative to that detected in the absence of the candidate modulator agent indicates that the at least one candidate modulator agent is an MNP activator. The method may further comprise measuring and comparing expression of IL-1β levels in the presence and absence of the candidate modulator agent.

BRIEF DESCRIPTION OF THE FIGURES

FIG. 1A-G. Intestinal $CX_3CR1^+$ cells protect mice from *C. rodentium*-induced colitis. A, B. Depletion efficiency in the $Cx3cr1^{DTR/GFP}$ mice was assessed by flow cytometry of small intestinal lamina propria cells $Cx3cr^{DTR/GFP}$ or littermate control mice after administration of diphtheria toxin (DT) to both groups daily for 2 days. A. Surface staining for CD11b versus $CX_3CR1$-GFP. B. $MHCII^+$ $CD11c^+$ cells were assessed for expression of $CX_3CR1$, CD103 and CD14. Results are representative of 5 independent experiments with a minimum of 3 animals per group. C. Total number of $MHCII^+$ $CD11c^+$ $CD103^+$ (left) and $MHCII^+$ $CD11c^+$ $CX_3CR1^+$ cells (right) per intestine as determined by flow cytometry analysis. n.s.=p>0.05. **p≤0.01. 2-tailed t-test. Error bars represent the SEM. Results are representative of 5 independent experiments with a minimum of 3 animals per group D. Weight of DT-treated littermate wildtype (control) mice or $Cx3cr1^{DTR/+}$ mice following infection with *C. rodentium* (N=7 mice/group). Diphtheria toxin (DT) was administered at days −2, −1, and 0 and every other day post-infection. Data are representative of 2 independent experiments. E. Representative colonic histology from littermate control mice or $Cx3cr1^{DTR+}$ mice (analyzed in D) infected with *C. rodentium* at day 7 post-infection. 20× objective, (<) areas of lymphocyte infiltration, (*) areas of epithelial erosion. 100 μm scale bar is shown. F. Survival curves of DT-treated $Cx3cr1^{DTR/+}$ and littermate control mice infected with *C. rodentium* or uninfected (N=7 mice/group). Data are representative of 3 independent experiments. Animals were treated with DT as in D. G. Bacterial CFUs of spleens from littermate wildtype (control, n=5) mice or $Cx3cr1^{DTR/+}$ mice (n=5) infected with *C. rodentium* and treated with DT as above. *p≤0.05. 2-tailed t-test. Error bars represent the SEM. One of two representative experiments is shown.

FIG. 2A-H. $CX_3CR1^+$ cells support colonic ILC3 production of IL-22. A. Survival curves of *C. rodentium*-infected $Myd88^{f/f}$ littermate controls (N=10, white circle) as compared to CD11c-cre/$Myd88^{f/f}$ mice without (N=13, dark circle) or with (N=5, triangle) exogenous hydrodynamic delivery of an IL-22-producing plasmid. Results are a composite of two independent experiments. B. Survival curves of DT-treated $Cx3cr1^{DTR/+}$ mice infected with *C. rodentium* following hydrodynamic delivery of a plasmid expressing IL-22 (n=8) or control vector (n=9). Diphtheria toxin (DT) was administered at days −2, −1, and 0 and every other day post-infection. Results are a composite of three independent experiments. C, D, E. Percentage (C, D) and total number (E) of colonic Lin⁻ $CD90.2^+$ ILCs producing IL-22 from DT-treated $Cx3cr1^{DTR/+}$ (N=10) and littermate control mice (N=9) 7 days after *C. rodentium* infection and from uninfected mice, NT (N=3). Results are a composite of two independent experiments. Diphtheria toxin (DT) was administered at days −2, −1, and 0 and every other day post-infection. Intracellular IL-22 was assayed by flow cytometry after 4 h culture. A representative flow cytometry plot from each group is shown in C. **p≤0.01. One way ANOVA with Bonferroni's correction. Error bars represent the SEM. F. Total number of ILC3 per colon in $Cx3cr1^{DTR/+}$ (N=9) or control (N=8) mice administered DT. Error bars represent the SEM. Results are one of three representative experiments. G. Total number of $IL-17^+$ or $IL-22^+$ colonic $CD4^+$ T cells from DT-treated $Cx3cr1^{DTR/+}$ (N=10) and littermate control mice (N=9) 7 days after *C. rodentium* infection and from uninfected mice (N=3). Intracellular IL-22 and IL-17 was assayed by flow cytometry after 4 h culture. *p≤0.05. One way ANOVA with Bonferroni's correction. Error bars represent the SEM. Results are a composite of two independent experiments. H. Confocal immunofluorescence of colonic samples from $Cx_3Cr1^{GFP/+}$ mice stained for CD3 and RORγt. 25× oil objective, 10 μm scale bar is shown. White arrows indicate sites of MNP and ILC3 juxtaposition.

FIG. 3A-F. TLR-stimulated $CX_3CR1^+$ MNPs are stronger inducers of ILC3 production of IL-22 than $CD103^+$ $CD11b^+$ DCs and monocytes. A-C. CD103 or $CX_3CR1^+$ $MHCII^+$ $CD11c^+$ $CD11b^+$ cells were isolated from the lamina propria of $CX_3CR1^{GFP/+}$ mice (sort strategy shown in A) and co-cultured with Lin⁻ RORγt-$GFP^+$ ILCs with or without the indicated bacterial TLR ligands or IL-23. IL-22 was assessed by intracellular staining of $CD90.2^+$ ILCs after 18 h. A representative flow cytometry plot is shown in B. C. Percent $IL-22^+$ ILCs is shown from seven independent experiments. **p≤0.01, *p≤0.05. One way ANOVA with Bonferroni's correction. Error bars represent SEM. D-F. $Ly6C^+$ $MHCII^{lo}$ (Monocytes) and $Ly6C^-$ $MHCII^{hi}$ (MNPs) were isolated from $CX_3CR1^+$ $CD11b^+$ lamina propria cells (sort strategy is shown in D) and co-cultured with intestinal ILCs with LPS or IL-23 as indicated. Intracellular cytokine staining for IL-22 is shown after 18 h (E). Supernatants were harvested after 18 h and IL-22 production quantitated by ELISA (F). Results are representative of 2 independent experiments performed in triplicate. ***p≤0.001. One-way ANOVA with Bonferroni correction. Error bars represent the SEM.

FIG. 4A-E. $CX_3CR1^+$ MNP-derived IL-23 and IL-1β activate ILC3 to produce IL-22. A. Phenotype analysis of colonic LPMCs from $Cx3cr1^{STOP-DTR/GFP}$ mice with or without CD11c-cre following DT injection for 2 days. Top panel: selective depletion of $CX_3CR1^{hi}$ MNPs. Lower panel: Expression of Ly6C and MHCII on $CX_3CR1^{hi}$ and $CX_3CR1^{int}$ populations. B. Expression of IL-22 in Lin⁻ $CD90.2^+$ colonic ILCs from $Cx3cr1^{STOP-DTR/+}$ (Stop-DTR) or CD11c-Cre×$Cx3cr1^{STOP-DTR/+}$ (Cre-DTR) mice at 7 days after *C. rodentium* infection. Diphtheria toxin (DT) was administered at days −2, −1, and 0 and every other day post-infection. One representative intracellular cytokine flow cytometry plot is shown on the left and a composite graph (N=6/group) on the right. *p≤0.05, 2-tailed t-test. Error bars represent the SEM. Results are a composite of two independent experiments. C. Supernatants from APC-ILC co-cultures (from FIG. 3B-C) were harvested after 18 h and assayed for IL-23 by ELISA. Results are averages of 3 independent experiments and the SEM is shown. D. $CX_3CR1^+$ MNPs or $CD103^+$ $CD11b^+$ DCs were sorted and incubated with media or CpG for 18 h and supernatants were assayed for IL-1β by ELISA. Results are an average of 2 independent experiments performed in duplicate and the SEM is shown. *p≤0.05; **p≤0.01. E. Lin⁻ $CD90.2^{hi}$ ILCs from WT or $Il1r^{-/-}$ mice were co-cultured with sorted intestinal MNPs from WT or $Il23p19^{-/-}$ mice, with or without CpG as indicated. IL-22 production by the ILCs was assessed after 18 h by ELISA. Data are combined from 3 independent experiments performed in duplicate. *p≤0.05, ***p≤0.001. One-way ANOVA with Bonferroni correction. Error bars represent the SEM.

FIG. 5A-G. Increased ILC3 production of IL-22 in mild to moderate IBD correlates with presence of fecal stream. A.

Figure 8:
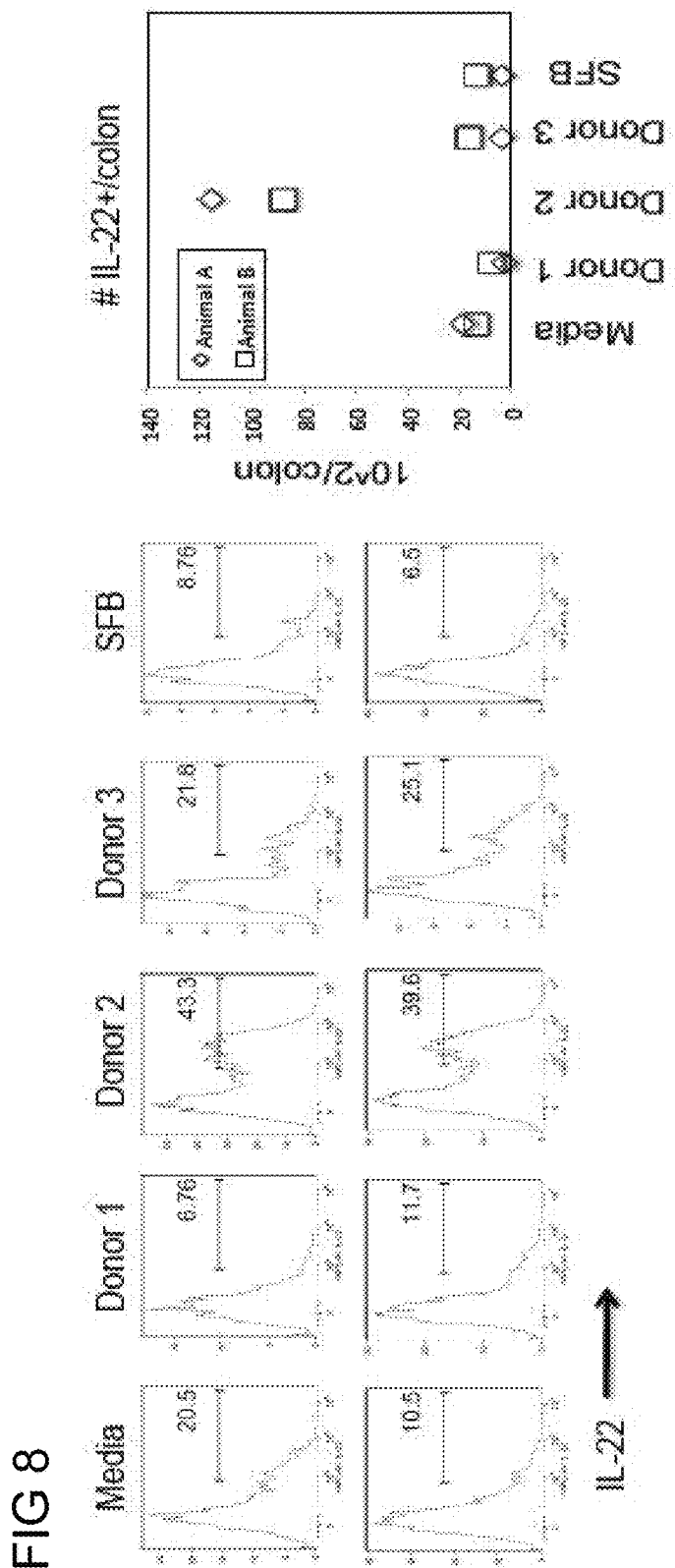

LPMCs isolated from descending colon biopsies from patients with endoscopically mild to moderate Crohns' disease (N=8, red) or ulcerative colitis (N=6, blue) (FIG. 10) as well as age-matched non-IBD control patients undergoing routine screening colonoscopy (N=8, white) were stimulated ex vivo with PMA/ionomycin and evaluated by intracellular cytokine staining for expression of IL-17 and IL-22. The percentage of $CD3^+$ or $CD3^-$ fraction expressing IL-17 or IL-22 is indicated. *p≤0.05, 2-tailed t-test. Black bars represent the geometric mean. B. Expression of c-Kit and CD56 in electronically gated $CD3^-$ $IL-22^+$ (black lines) and $CD3^-$ $IL-22^-$ (gray) LPMCs. C. Expression of RORγt by $c-Kit^+$ $CD56^+$ LPMCs. Lineage negative cells (CD14/CD19/CD3/CD11b/CD11c/TCRγδ-negative, see FIG. 12A) were stained with antibodies to surface markers c-Kit and CD56 and to intracellular RORγt. $Lin^-$ $CD56^+$ $c-Kit^+$ ILC3 (black line) were compared to $Lin^-$ $CD56^+$ $c-Kit^+$ NK cells (gray) for RORγt expression. D. Surface staining of $Lin^-$ $c-Kit^+$ ILCs for the indicated markers (black line) compared to isotype control (gray) and all live LPMCs (dotted line) E. LPMCs stained for intracellular IL-22 following stimulation with IL-23 for 3 h (solid line) or with control media (dotted line). Cells shown were gated on $Lin^-$ $CD56^+$ $c-Kit^+$. The isotype control is in gray. F. $CD11c^+$ $MHCII^+$ human colonic APCs were electronically gated for expression of CD103 and CD14. One of three donors is shown. G. Lamina propria cells from biopsy samples of tissue exposed (pre-diversion) or not exposed to the fecal stream (post-diversion) were cultured for 3 hours and ILC3 production of IL-22 was assessed by flow cytometry. Left panel: result from one representative donor. Right panel: percent $IL-22^+$ ILCs in afferent (Pre) and efferent (Post) limbs of three diverted patients. **p≤0.01, 2-tailed t-test. Black bars represent the geometric mean.

FIG. 6A-G. Human ILC3 production of IL-22 is supported by IL-23 and IL-1β produced by TLR-stimulated $CD14/CX_3CR1^+$ MNPs. A, B, C. $HLA-DR^+0$ $CD11c^+$ cells from intestinal resection tissue were sorted into $CD103^+$ DCs and $CD14^+$ MNPs subpopulations and transcriptional profiles were assessed by RNA-seq. A. Sorting strategy. B. Each subset was examined for expression of the indicated cell surface markers. Isotype controls are shown in gray. One of three donors is shown. C. Heatmap of relative expression of relevant MNP-related genes. Values represent the average of two independent donors, and an asterisk denotes individual genes differentially expressed at an FDR=0.01. D, E. Induction of IL-22 in human ILCs in co-culture with $CD14^+$ MNPs or $CD103^+$ DCs in the presence of media alone, LPS, or flagellin, as indicated. $c-Kit^+$ cells were examined for intracellular IL-22 production following 18 h culture. Data are representative of 5 independent experiments. F. $CD14^+$ MNPs or $CD103^+$ DCs sorted from human intestine (as in A) were stimulated with the indicated TLR ligands for 18 h and qPCR or cytometric bead array analysis were used to quantitate IL-23p19 and IL-1β, respectively. Results are averaged from 3 independent donors, and technical replicates were performed in duplicate or triplicate, respectively. *p≤0.05. N.D., not detected. 2-tailed t-test. Error bars represent the SEM. G. Sorted human intestinal $CD14^+$ MNPs and ILCs were left unstimulated or were co-cultured in the presence of LPS with or without neutralizing antibodies against IL-1β and IL-23. IL-22 ELISA was performed after 18 h. Results are averaged from 2 independent donors performed in duplicate. *p≤0.05. 2-tailed t-test. Error bars represent the SEM.

FIG. 7A-H. $CX_3CR1^+$ MNP-derived TL1A synergizes with IL-23 and IL-1β to induce IL-22 in intestinal ILC3. A. Gene-set enrichment analysis was used to determine whether the indicated disease-related SNP were differentially expressed between $CD14^+$ MNPs and $CD103^+$ DCs. Significance was estimated using the hypergeometric cumulative distribution, with a raw p-value cutoff of 0.05 for differential expression. Data were averaged from two independent donors. B. B cells ($CD3^-$ $CD19^+$), $CX_3CR1^+$ MNPs, $CD103^+$ DCs, and $Ly6C^+$ monocytes were sorted from the intestinal lamina propria of $Cx3cr1^{GFP/+}$ and quantitative PCR for TL1A was performed. Relative quantitation was performed by ΔCt normalized to GAPDH expression. Data are from 2 biological replicates performed with two technical replicates. *p≤0.05. 2-tailed t-test. C-E. Sorted intestinal ILCs from mice (C,E) or cultured human intestinal ILCs (D) were stimulated with media alone, IL-1β, or IL-23 with or without TL1A as indicated for 18 h. Brefeldin was added to the cultures 4 h prior to intracellular cytokine staining for IL-22 (C, D) or GM-CSF (E). Data are representative of 6 independent experiments. F-H. Sorted intestinal ILCs were transfected with siRNA targeting Tnfrsf25 or a scramble control. F. Knockdown efficiency was assessed after 24 h by flow cytometry comparing scramble control (solid line) with Tnfrsf25 siRNA. One of two representative experiments is shown. ILCs were then cultured with media alone (−) or IL-23 and TL1A or co-cultured with $CX_3CR1^+$ MNPs with or without LPS as indicated for an additional 18 h. G. IL-22 production was measured by intracellular flow cytometry. Brefeldin was added to the cultures 4 h prior to intracellular cytokine staining Data are representative of 2 independent experiments. H. IL-22 secretion by samples from (G) were assessed by ELISA, performed in duplicate, prior to addition of Brefeldin. *p≤0.05; **p≤0.01. 2-tailed t-test. Error bars represent SEM.

FIG. 8: Germ free mice were colonized with media control, segmented filamentous bacteria (SFB), or microbiota from patients with IBD (Donor 1, 2, 3). Colonic ILC3s are shown 2 weeks after colonization with intracellular cytokine staining for IL-22. Two mice per group are shown and the number of IL-22+ ILC3/colon is shown for both mice in the graph to right.

FIG. 9A-E: Nucleic acid sequences for human TL1A A. transcript variant 1 and B. transcript variant 2 and C. amino acid sequence of human TL1A. Nucleic D. and amino E. acid sequences for mouse TL1A.

FIG. 10. Gating strategy for colonic ILC3. Live, lineage negative (CD3/TCRγδ/NK1.1/CD11b) CD90.2 hi colonic lamina propria lymphocytes expressing RORγt+(ILC3s) were electronically gated to analyze ILC3 function.

Figure 11:
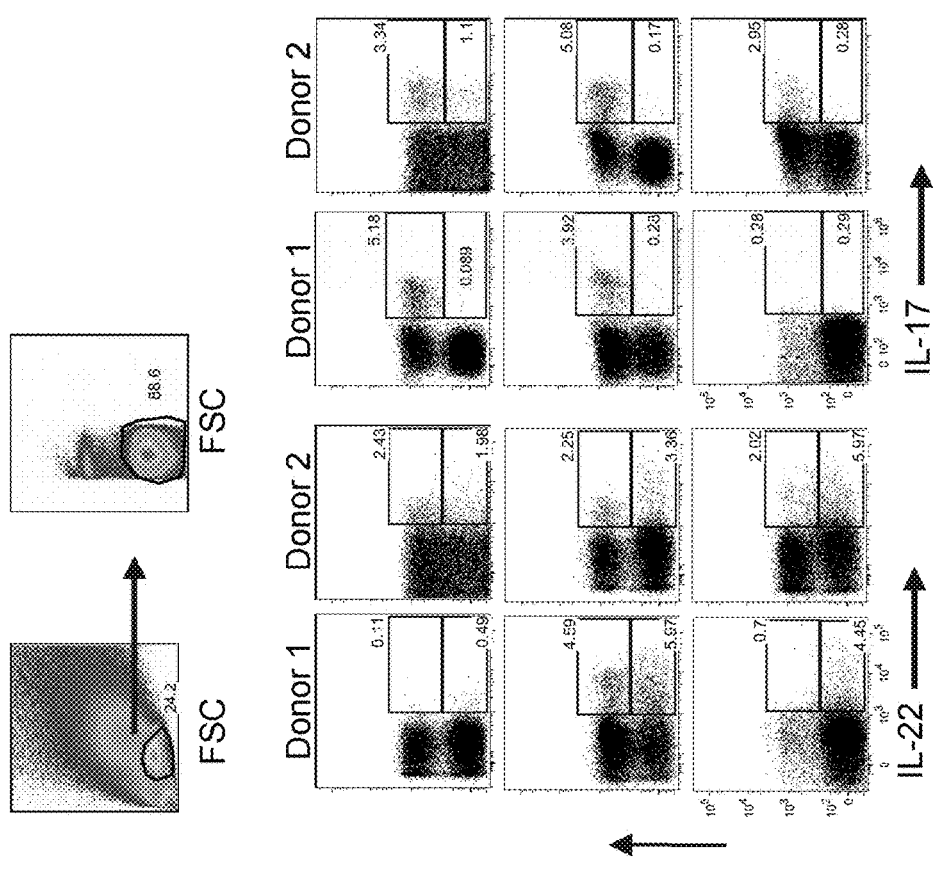

FIG. 11. Increased production of IL-22 in ILCs from patients with IBD. A. LPMCs from patients (non-IBD controls, CD, and UC patients) were stimulated for 4 h with PMA and ionomycin in the presence of Brefeldin. Samples were analyzed by flow cytometry for cytokine production. Top shows gating strategy for live lamina propria lymphocytes. Representative intracellular staining of LPMCs from 2 patients per group is shown. Composite data are shown in FIG. 5A.

FIGS. 12A-12B. Lineage negative gating and surface phenotype for human intestinal ILC3. A. ILCs are defined as live, lineage negative (CD14−/CD19−/TCRγδ−/CD3−/CD11c−/CD11b−) cells that are c-kit+, CD56+, CD127+ and CD45int (see FIG. 5). B. Representative patient PBMCs and LPMCs from afferent limb (pre-diversion) and efferent limb (post-diversion) stained for ILC3 cell surface phenotype (Lin− CD56+c-Kit+) and intracellular expression of RORγt.

Figure 13:
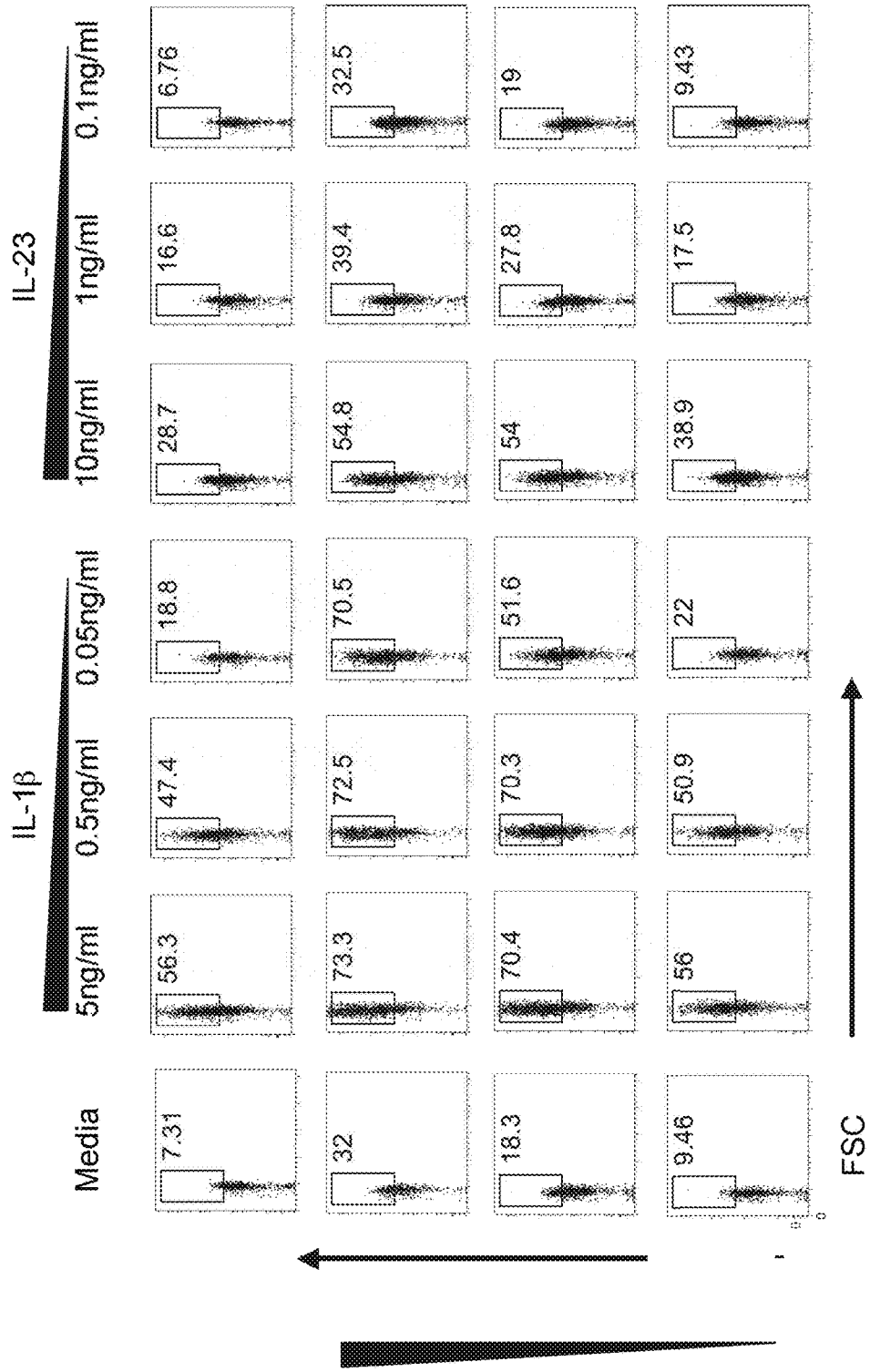

FIG. 13. TL1A enhances IL-23 and IL-1β induction of IL-22 by intestinal ILC3s. Sorted intestinal ILCs from mice were stimulated with media alone, IL-1β, or IL-23 with or without TL1A at the indicated concentrations for 18 h. Brefeldin was added to the cultures 4 hours prior to intracellular cytokine staining Data are representative of 3 independent experiments.

FIG. 14. FIG. 14 Lists IBD Patient Characteristics.

DETAILED DESCRIPTION OF THE INVENTION

In this disclosure, we show that in vivo depletion of $CX_3CR1^+$ mononuclear phagocytes (MNPs) resulted in more severe colitis and death following infection with *C. rodentium*. This phenotype was rescued by exogenous IL-22, which was endogenously produced by ILC3 in close spatial proximity to $CX_3CR1^+$ MNPs that were dependent on MyD88 signaling. $CX_3CR1^+$ MNPs from both mouse and human tissue produced more IL-23 and IL-1β than conventional $CD103^+$ dendritic cells (cDCs) and were more efficient than cDCs in supporting IL-22 induction in ILC3 in vitro and in vivo. Further, colonic ILC3 from patients with mild to moderate ulcerative colitis or Crohn's disease had increased IL-22 production. IBD-associated SNP gene set analysis revealed enrichment for genes selectively expressed in human intestinal MNPs. The product of one of these, TL1A, potently enhanced IL-23- and IL-1β-induced production of IL-22 and GM-CSF by ILC3. Collectively, these results reveal a critical role for $CX_3CR1^+$ mononuclear phagocytes in integrating microbial signals to regulate colonic ILC3 function in IBD.

Additionally, data provided in this disclosure support a role for microbial signals, acting by way of mononuclear phagocytes, in regulating the effector functions of ILC3. In particular, we showed that MyD88-dependent signaling was required in CD11c-expressing cells to enable colitis-induced production of IL-22 by ILC3, and that ILC3 production of IL-22 correlated with exposure to the fecal stream in patients with IBD. The induction of IL-22 was required for protection of the epithelial barrier from colitis-inducing bacteria. The results indicate that microbiota that can induce production of IL-22 and other effector cytokines in ILC3 can confer protection from pathogenic processes in inflammatory bowel diseases.

These results are presented and described herein and in Longman et al. (2014, J Exp Med 211:1571-1583), the entire content of which is incorporated herein by reference.

By way of background, IBD has been defined as a dysregulated cellular immune response to environmental triggers in genetically predisposed individuals. Although the initial discovery linking single nucleotide polymorphisms in the IL23R locus with susceptibility to IBD (Duerr et al., 2006) was consistent with a role for IL-23-responsive T cells, more recent evidence supports the importance of IL-23-responsive innate lymphoid cells (ILC) in maintaining epithelial homeostasis (Sonnenberg and Artis, 2012). These RORγt-dependent ILCs (now named group 3 ILCs, or ILC3 (Spits et al., 2013)) were initially characterized in mouse models of colitis as predominant producers of IL-22 (Satoh-Takayama et al., 2008), an IL-1β family member which signals via STAT3 to regulate mucosal healing, a critical clinical endpoint in IBD (Hanash et al., 2012; Pickert et al., 2009). In light of their robust production of IL-22 and close proximity to the intestinal epithelial layer (Cella et al., 2009), ILC3 have been proposed to play an important role in mucosal healing and maintenance of barrier integrity, and understanding how they are induced to produce IL-22 has great potential for therapeutic benefit.

Mononuclear phagocytes (MNPs) are sentinels of the intestinal lamina propria, capable of responding to microbial products, and play a crucial role in orchestrating intestinal lymphocyte homeostasis. MNPs can be subdivided based on their expression of CD103 or $CX_3CR1$, and each group has been ascribed critical functions in maintaining intestinal homeostasis (Bogunovic et al., 2009; Merad et al., 2013). $CD103^+$ cells, which can be further subdivided based on the expression of CD11b, differentiate from a common DC precursor and are thought to be the conventional, migratory myeloid DCs (Varol et al., 2010). $CD103^+$ $CD11b^-$ DCs require Irf8, Id2, and Batf3 for their development and are thought to play a critical role in cross-priming virus- and tumor-specific CTLs (Hildner et al., 2008; Merad et al., 2013). Loss of these cells, however, does not alter intestinal T cell homeostasis or lead to spontaneous inflammation (Edelson et al., 2010). $CD103^+$ $CD11b^+$ DCs, in contrast, require Notch2 signaling, produce IL-23 in response to flagellin-induced TLR5 activation, resulting in IL-22 production by ILC3, and have additionally been proposed to support Th17 polarization (Kinnebrew et al., 2012; Lewis et al., 2011). These cells can produce retinoic acid, which promotes the expression of the gut-homing receptor CCR9 and synergizes with TGFβ to induce regulatory T cells (Sun et al., 2007). One recent study suggests that Notch2-dependent $CD103^+$ $CD11b^+$ DCs regulate protection from *C. rodentium*-induced colitis (Satpathy et al., 2013). However, specific depletion of $CD103^+$ $CD11b^+$ intestinal DCs revealed that these cells are not the MNP subset required for protection against *C. rodentium* or IL-22 production (Welty et al., 2013).

In contrast to $CD103^+$ cDCs, $CX_3CR1^+$ MNPs differentiate from monocyte precursors (Varol et al., 2010). Although these cells were previously thought to be tissue-resident and to promote local $T_{reg}$ differentiation (Hadis et al., 2011), recent data from our group showed that they can upregulate CCR7 and migrate to secondary lymphoid organs, suggesting a broader role in orchestrating immunity (Diehl et al., 2013). Notably, we observed that interaction with microbiota limits the migration of these cells to mesenteric lymph nodes (MLN) (Diehl et al., 2013), and an increase in $CX_3CR1^+$ cells has been described in the lamina propria during mouse (Zigmond et al., 2012) and human colitis (Kamada et al., 2008). A recent study reported that fractalkine receptor ($CX_3CR1$) expression supports innate cell-dependent clearance of *C. rodentium* infection (Manta et al., 2013), but a functional role for $CX_3CR1^+$ MNPs in regulating colitis-associated ILC3 remains unclear. In order to evaluate this question, we employed novel mouse models to enable selective depletion of $CX_3CR1^+$ MNPs in vivo. Our results reveal a critical role for $CX_3CR1^+$ MNPs from both mouse and human tissue in supporting IL-22 induction in ILC3 in vitro and in vivo. Moreover, we identify the ability of TL1A produced by MNPs to potently enhance IL-23- and IL-1β-induced production of IL-22 and GM-CSF by ILC3.

In accordance with results presented herein, in one aspect, the present disclosure provides a method for stimulating GI mucosal healing. The method comprises administering to an individual, a composition comprising agents that induce ILC3 production of IL-22. The present disclosure also provides compositions comprising such agents. In one embodiment, this disclosure provides a method for reducing GI mucosal inflammation in an individual comprising the step of administering to the individual a composition comprising agents that induce ILC3 production of IL-22.

In one embodiment, the agent is TL1A (TNF-like ligand 1A, also known as TNFSF15). TL1A is a TNF superfamily member. It binds to the death-domain receptor DR3 and provides costimulatory signals to activated lymphocytes. Human and mouse TL1A—both purified from biological materials or produced recombinantly, can be made and are also commercially available (such as from Enzo Life Science; R&D Systems; and Human Genome Sciences, Inc.). Exemplary nucleic acid sequences encoding human and mouse TL1A are designated herein SEQ ID NOs: 1 and 2 and SEQ ID NO: 4, respectively. Exemplary amino acid sequences of human and mouse TL1A are designated herein SEQ ID NOs: 3 and 5, respectively. See, for example, FIG. 9A-E.

In another embodiment, the agent is a molecule that activates the receptor for TL1A (i.e., activates DR3)—such as, for example, an agonist to the D3 receptor. An agonist to DR3 receptor refers to a naturally occurring or synthetic compound capable of enhancing or potentiating DR3 mediated biological activities, such as cellular proliferation and/or differentiation. An example of a DR3 receptor agonist is an antibody. Such antibodies can be generated by techniques known in the art and are also commercially available (such as from Biolegend and Human Genome Sciences, Inc.). See also Papadakis et al. (2004, J Immunol 172:7002); Prehn et al. (2004, Clin Immunol 112:66); Migone et al. (2002, Immunity 16:479); and Wen et al. (2003 J Biol Chem 278:39251), for example, which describe recombinant TL1A (amino acids 72-251) and agonistic anti-DR3 monoclonal antibodies (clone F05, IgG1) and sources thereof; each of which references is incorporated herein in its entirety by reference. In one embodiment, the agent is a fragment of such an antibody that comprises a receptor binding domain of the antibody.

In another embodiment, the agent for inducing ILC3 to provide IL-22 stimulates $CX_3CR1^+$ MNPs. In one embodiment, the agent is a composition comprising one or more types of microbes found in fecal microbiota. In one embodiment, the fecal microbiota is human fecal microbiota.

In one embodiment, the agent induces ILC3 to produce GM-CSF. Therefore, the compositions and methods of the present disclosure may be used to induce oral tolerance as it is known that production of GM-CSF induces oral tolerance.

In one embodiment, the disclosure provides a method for enhancing the function of CX3CR1+ MNPs. The method comprises administering to an individual in need thereof a composition comprising human fecal material or an extract thereof (e.g., a fecal filtrate) comprising human gut microbiota. The term gut microbiota as used herein refers to the microbe population living in the human gut. The term "extract of the gut microbiota" as used herein means a composition comprising at least one phyla of bacteria, at least one class of bacteria, at least one order of bacteria, at least family of bacteria, or at least one species of bacteria obtained from the gut microbiota.

Compositions useful in the method of the present disclosure may be produced by processing fecal material comprising fecal microbes. The term "fecal microbes" refers to microorganisms that are present in the gut, intestine, or colon of humans.

In one embodiment the present disclosure provides a composition that comprises human gut microbiota bacteria that belong to at least 1, at least 2, at least 3, at least 4, at least 5, at least 6, at least 7, at least 8, at least 9, at least 10 phyla, or from 1-10 phyla. In one embodiment, the composition comprises human gut microbiota bacteria that belong to at least 1, at least 2, at least 3, at least 4, at least 5, at least 6, at least 7, at least 8, at least 9, at least 10 classes, or from 1-10 classes. In one embodiment, the present composition comprises human gut microbiota bacteria that belong to at least 1, at least 2, at least 3, at least 4, at least 5, at least 6, at least 7, at least 8, at least 9, at least 10 orders, or from 1-10 orders. In one embodiment, the present composition comprises human gut microbiota bacteria that belong to at least 1, at least 2, at least 3, at least 4, at least 5, at least 6, at least 7, at least 8, at least 9, at least 10 families, or from 1-10 families. In one embodiment, the present composition comprises human gut microbiota bacteria that belong to at least 1, at least 2, at least 3, at least 4, at least 5, at least 6, at least 7, at least 8, at least 9, at least 10 genuses, or from 1-10 or 10-20 genuses. In one embodiment, the present composition comprises human gut microbiota bacteria that belong to at least 1, at least 2, at least 3, at least 4, at least 5, at least 6, at least 7, at least 8, at least 9, at least 10 species, 1-10 or 1-20 species, at least 50 or at least 100 species of bacteria.

The various fractions of the gut microbiota may be prepared by isolation of individual types (phyla, classes, orders, families, genuses, and/or species) of bacteria from human fecal material and then generating mixtures of different and/or desired types. In one embodiment, the fecal material may fractionated by chemical means or limiting dilution to obtain compositions comprising microbes having desired properties. In one embodiment, the fecal material may be obtained from an individual who has IBD. In another embodiment, the fecal material may be from an individual who does not have IBD. The fecal material may first be tested on mice as described herein to determine if the fecal material induced increased production of IL-22 and if so, the material may be processed to isolate, and if desired, combined one or more types of microbes or bacteria.

Fecal transplant or fecal microbiota transplantation (FMT) has been used successfully for the treatment of *Clostridium difficile* infections (CDI), including therapy resistant forms thereof. As described in Borody et al. (Curr Gastroenterol Rep. 15: 337, 2013; the entire content of which is incorporated herein by reference) and understood in the art, FMT material is typically derived from healthy donors who have no risk factors for transmissible diseases and have not been exposed to agents, such as, for example, antibiotics, that could alter the composition of their gut microbiota. FMT donor selection criteria and screening tests are outlined in detail in published international guidelines established by the FMT Working Group (Bakken et al. Clin Gastroenterol Hepatol. 9:1044-9, 2011). Details pertaining to the harvesting and processing of FMT material are known in the art and are reviewed in Borody et al. (supra). Briefly, many protocols call for use of fresh feces, which requires collection and processing on the same day scheduled for the FMT. Other protocols have been developed that use highly filtered human microbiota mixed with a cryoprotectant, which can be frozen for storage at −80° C. until required for use (Hamilton et al. *Am J Gastroenterol.* 107(5):761-7, 2012). This approach benefits from convenience with regard to scheduling, and generates a processed fecal material (fecal filtrate) having reduced volume and fecal aroma. Equivalent clinical efficacy has been noted when either purified processed fecal material or fresh, partly filtered feces were used in CDI. FMT material may be administered via naso-duodenal, transcolonoscopic, or enema based routes. Although protocols described in, for example, Borody et al. typically call for isolation and purification of FMT material from healthy donors, these protocols are equally well applied to FMT material isolated and purified from donors with diagnosed with various conditions. Results presented herein demonstrate that FMT material isolated and purified from patients afflicted with, for example, IBD possess properties which confer clinical benefit with regard to promoting mucosal healing.

In addition to bacteria, the compositions useful for the present method may also comprise other microbes present in fecal material such as protozoa, fungi and viruses. In one embodiment, the compositions useful for the present method are free of pathogenic bacteria and/or pathogenic microbes.

The present compositions may comprise one or more pharmaceutically acceptable carriers. Such carriers are well known in the art and include fillers, binders, wetting agents, surfactants, lubricants, and the like. Typically, the carriers are inert. The formulations for administrations may be in the liquid form (suspensions, dispersions, solutions etc.), solid form (tablets, powder, capsules, etc.), or may be in the form of pastes, ointments, gels and the like.

In one embodiment, the formulations comprising TL1A or DR3 agonists are administered orally or rectally, or via intravenous, mucosal, intramuscular, transdermal or any other route that enables the active ingredients to reach the gut mucosa. In one embodiment, the formulations containing one or more types of fecal microbes may be delivered orally or rectally.

In a particular embodiment, the present compositions are formulated for specific delivery to the small intestine or the large intestine. In a circumstance wherein the composition is administered to a subject with, for example, Crohn's Disease, an inflammatory bowel disease that predominantly affects the small intestine and to a lesser degree, the large intestine, a composition described herein is formulated for release in the small intestine. Such formulations are known in the art and deliver the formulaic payload in a pH dependent manner. For specific delivery to the small intestine, the formulation releases therapeutic agents at about pH 6, a pH characteristic of the small intestine. In a circumstance wherein the composition is administered to a subject with, for example, ulcerative colitis, an inflammatory bowel disease that predominantly affects the large intestine and colon, a composition described herein is formulated for release in the large intestine. For specific delivery to the large intestine, the formulation releases therapeutic agents at about pH 7, a pH characteristic of the large intestine.

Targeting the small intestine for specific delivery of the therapeutic agents described herein, such as, for example, TL1A or a mimic thereof or a DR3 agonist, ensures that these therapeutic agents are delivered specifically to the desired target cells in the small intestine that are responsive to such therapeutic agents and induce mucosal healing as a result of contact with such agents. Results presented herein identify ILC3s as the target cell population resident in the aforementioned organs (small and large intestine and colon) that respond to the therapeutic agents described herein (e.g., TL1A) to promote mucosal healing and maintain barrier integrity. As is understood in the art, ILC3s are innate cells that develop independently of the thymus and do not express T cell receptors (TCRs). ILCs are distinct from other lymphocytes, such as, for example, Th17 cells, which are also present in target organs, but are adaptive immune cells that require the thymus for maturation and express TCRs. It is also noteworthy that naive T cells are not present in target organs.

As detailed in results presented herein, localized release of TL1A by $CX_3CR1^+$ MNPs in mouse and human tissue (e.g., the small intestine) potently enhances IL-23- and IL-1β-induced production of IL-22 and GM-CSF by ILC3. Secretion of IL-22 and GM-CSF by ILC3, in turn, promotes barrier homeostasis, mucosal healing, and oral tolerance. Accordingly, targeting the therapeutic agents described herein specifically to ILC3s in target organs can be used to advantage to treat subjects afflicted with diseases or conditions characterized by impairment or loss of barrier integrity in the target organs. By way of example, delivery of TL1A to ILC3s in the small intestine of a subject with Crohn's Disease confers therapeutic benefit to such a subject by promoting mucosal healing and at least partial restoration of epithelial barrier integrity.

Further to the above, it is also noteworthy that prior to the discoveries based on the results presented herein, the scientific community viewed TL1A as a promoter or inducer of the development of chronic mucosal inflammation that acts by enhancing Th1 and Th17 activation. See, for example, Takedatsu et al. (2008, Gastroenterology 135:552), Pappu et al. (2008, J Exp Med 205:1049), Kamada et al. (2010, Inflamm Bowel Dis 16:568), WO2008/106451, WO2009/064854, and WO2012/064682; the entire content of each of which is incorporated herein by reference. The prevailing attitude in the scientific community is also underscored by U.S. Pat. No. 8,766,034 (the entire content of which is incorporated herein by reference), which discloses that blocking TL1A-DR3 signaling is a promising therapeutic strategy in a variety of T cell-dependent autoimmune diseases including forms of IBD (e.g., Crohn's disease and ulcerative colitis) and related fibrotic conditions (e.g., liver periportal fibrosis, bile duct fibrosis, primary biliary cirrhosis, liver periportal inflammation, and bile duct inflammation). In sum, these studies suggest and demonstrate that inhibitors or antagonists of TL1A or DR3 would be well suited for therapeutic intervention in the context of IBD. In contrast, the present findings suggest that TL1A and activation of DR3 on ILC3s by TL1A promotes mucosal healing by inducing ILC3 expression of IL-22 and GM-CSF and thus, are proposed as agents for treating IBD.

The formulations may be administered to an individual in need of treatment. Determination of the dosage and administration regimen is well within the purview of clinicians or others skilled in the art.

In accordance with results presented herein, the therapeutic agents described herein (e.g., TL1A) are administered in the context of a delayed-release (DR), sustained release or compression coated pharmaceutical composition comprising an enteric or compression coating and a pharmaceutically acceptable carrier and excipient, wherein the enteric or compression coating delays or substantially eliminates the release and/or absorption of the therapeutic agent in the upper gastrointestinal (GI) tract. In a particular embodiment thereof, the pharmaceutical composition delays release of the therapeutic agent such that a substantial amount of the therapeutic agent load is released and/or absorbed in the small intestine and/or in the ileum and/or colon. Such enteric or compression coatings are known in the art and delay the release of therapeutic agents by about. e.g., 2-3 hours, 3-4 hours, or 4-6 hours. In a particular embodiment, the enteric or compression coating becomes soluble above or around about pH 6.0, pH 6.2, pH 6.3, pH 6.4, pH 6.5, pH 6.6, pH 6.7, pH 6.8, pH 6.9, or pH 7.0. In a particular embodiment, the composition is adapted to release at least about 80% by weight of the therapeutic agent load in the ileum and/or colon. In a more particular embodiment, upon ingestion of the pharmaceutical composition by a subject at least a portion (about 80%) of the therapeutic agent is absorbed in the ileum and/or colon of the subject.

In a further embodiment, a pharmaceutical composition for oral administration is envisioned, wherein the composition comprises: a) a core comprising a therapeutic agent and b) a pH-sensitive layer, wherein the pH-sensitive layer erodes to expose the core at least or about 2-3 hours, 3-4 hours, or 4-6 hours after ingestion of the composition by a subject, and wherein the pH-sensitive layer completely disintegrates at a pH characteristic of the small intestine, ileum and/or colon. In a particular embodiment thereof, the pH is about pH 6.0, pH 6.2, pH 6.3, pH 6.4, pH 6.5, pH 6.6, pH 6.7, pH 6.8, pH 6.9, or pH 7.0.

In yet another embodiment, a controlled release pharmaceutical composition for oral administration of a therapeutic agent is envisioned, the composition comprising a) a therapeutically effective amount of a therapeutic agent and b) a drug release controlling component capable of providing release of the therapeutic agent primarily in the small intestine, ileum, and/or colon, wherein after ingestion by a patient the therapeutic agent is released primarily in the small intestine, ileum, and/or colon. In a particular embodiment, at least about 80% of the therapeutic agent is released primarily in the small intestine, ileum, and/or colon. In a more particular embodiment, the drug release controlling component is selected from the group consisting of an enteric component and a time delay component. In a still more particular embodiment, the drug release controlling component is an enteric coating, wherein the enteric coating does not substantially dissolve in aqueous solution at a pH of above about pH 6.0, pH 6.2, pH 6.3, pH 6.4, pH 6.5, pH 6.6, pH 6.7, pH 6.8, pH 6.9, or pH 7.0 for at least about 30 minutes, 1 hour, or 2 hours. In yet another embodiment, the composition releases greater than about 80% of its therapeutic agent content in the small intestine. Exemplary enteric coatings and drug release controlling components envisioned for use in compositions described herein are selected from: cellulose acetate phthalate (CAP), hydroxypropyl methylcellulose phthalate (HPMCP), polyvinyl acetate phthalate (PVAP), hydroxypropyl methylcellulose acetate succinate (HPMCAS), cellulose acetate trimellitate, hydroxypropyl methylcellulose succinate, cellulose acetate succinate, cellulose acetate hexahydrophthalate, cellulose propionate phthalate, copolymer of methylmethacrylic acid and methyl methacrylate, copolymer of methyl acrylate, methylmethacrylate and methacrylic acid, copolymer of methylvinyl ether and maleic anhydride (Ganfrez ES series), ethyl methylacrylate-methylmethacrylate-chiorotrimethyl-ammonium ethyl acrylate copolymer, natural resins such as zein, shellac and copal collophorium, carboxymethyl ethylcellulose, Spheromer III, Spheromer IV, co-polymerized methacrylic acid/methacrylic acid methyl esters selected from: EUDRAGIT L12.5, L100, EUDRAGIT® S12.5, S100, EUDRAGIT® L30D55, EUDRAGIT® FS3OD, EUDRAGIT® L1OO-55, EUDRAGIT® S1OO (Rohm Pharma), KOLLICOAT® MAE3OD and 3ODP (BASF), ESTACRYL® 30D (Eastman Chemical), AQUATERIC® and AQUACOAT® CPD3O (FMC)), Acryl-EZE™ White, or equivalents thereof.

Pharmaceutical formulations that confer controlled or sustained release of therapeutic agents are known in the art and are described in, for example, U.S. Patent Application Publication No. 2012/0034303, the entire content of which is described herein by reference. Other materials as well as processing techniques and the like are set forth in Part 8 of *Remington's Pharmaceutical Sciences,* 17th edition, 1985, Mack Publishing Company, Easton, Pa., which is incorporated herein by reference in its entirety.

For the administration of the present compositions, the microbiota of the recipient may be cleared prior to administration of the exogenous microbiota composition or the recipient's microbiota may be left intact prior to administration of the exogenous microbiota composition.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

In conjunction with the above methods, the invention provides isolated antibodies which are agonistic anti-DR3 antibodies.

The antibodies for use in accordance with the present methods may be monoclonal or polyclonal as appropriate. Antibody fragments also envisioned for use include, for example, Fab, Fab', F(ab')$_2$ or Fv fragments. The antibody may be a single chain antibody. Other suitable modifications and/or agents will be apparent to those skilled in the art. Chimeric and humanized antibodies are also within the scope of the invention. It is expected that chimeric and humanized antibodies would be less immunogenic in a human subject than the corresponding non-chimeric antibody. A variety of approaches for making chimeric antibodies, comprising for example a non-human variable region and a human constant region, have been described. See, for example, Morrison et al., Proc. Natl. Acad. Sci. U.S.A. 81,6851 (1985); Takeda, et al., Nature 314,452 (1985), Cabilly et al., U.S. Pat. No. 4,816,567; Boss et al., U.S. Pat. No. 4,816,397; Tanaguchi et al., European Patent Publication EP 171496; European Patent Publication 0173494, United Kingdom Patent GB 2177096B. Additionally, a chimeric antibody can be further "humanized" such that parts of the variable regions, especially the conserved framework regions of the antigen-binding domain, are of human origin and only the hypervariable regions are of non-human origin. Such altered immunoglobulin molecules may be made by any of several techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and are preferably made according to the teachings of PCT Publication WO92/06193 or EP 0239400. Humanized antibodies can be commercially produced by, for example, Scotgen Limited, 2 Holly Road, Twickenham, Middlesex, Great Britain. The entire content of each of which references is incorporated herein by reference.

In certain embodiments, anti-idiotypic antibodies are also provided. Anti-idiotypic antibodies recognize antigenic determinants associated with the antigen-binding site of another antibody. Anti-idiotypic antibodies can be prepared against a second antibody by immunizing an animal of the same species, and preferably of the same strain, as the animal used to produce the second antibody. See, e.g., U.S. Pat. No. 4,699,880. In one embodiment, antibodies are raised against DR3 or a portion thereof, and these antibodies are used in turn to produce an anti-idiotypic antibody.

The present invention provides antibodies for both intracellular and extracellular targeting. Intracellular targeting can be accomplished through the use of intracellularly expressed antibodies referred to as intrabodies.

To screen for additional antibodies which bind to a particular epitope on the antigen of interest (e.g., DR3), a routine cross-blocking assay such as that described in Antibodies, A Laboratory Manual, Cold Spring Harbor Laboratory, Ed Harlow and David Lane (1988), can be performed. Alternatively, epitope mapping, e.g. as described in Champe et al. (1995) J. Biol. Chem. 270:1388-1394, can be performed to determine whether the antibody binds an epitope of interest. The entire content of each of which references is incorporated herein by reference.

Additional antibodies useful in the present methods can be also generated and selected using phage display approach as described, e.g. in U.S. Patent Appl. Publ. No. 2008/0213268.

Antibodies of the invention can be further modified to generate antibody mutants with improved physical, chemical and or biological properties over the parent antibody. Where the assay used is a biological activity assay, the antibody mutant preferably has a biological activity in the assay of choice which is at least about 10 fold better, preferably at least about 20 fold better, more preferably at least about 50 fold better, and sometimes at least about 100 fold or 200 fold better, than the biological activity of the parent antibody in that assay.

To generate the antibody mutant, one or more amino acid alterations (e.g. substitutions) can be introduced in one or more of the hypervariable regions of the parent antibody. Alternatively, or in addition, one or more alterations (e.g., substitutions) of framework region residues may be introduced in the parent antibody where these result in an improvement in the binding affinity of the antibody mutant for the antigen from the second mammalian species. Examples of framework region residues to modify include those which non-covalently bind antigen directly (Amit et al. (1986) Science 233:747-753); interact with/effect the conformation of a CDR (Chothia et al. (1987) J. Mol. Biol. 196:901-917); and/or participate in the $V_L$-$V_H$ interface (EP 239400B1). In certain embodiments, modification of one or more of such framework region residues results in an enhancement of the binding affinity of the antibody for the antigen from the second mammalian species. For example, from about one to about five framework residues may be altered in this embodiment of the invention. Sometimes, this may be sufficient to yield an antibody mutant suitable for use in preclinical trials, even where none of the hypervariable region residues have been altered. Normally, however, the antibody mutant will comprise additional hypervariable region alteration(s). The hypervariable region residues which are altered may be changed randomly, especially where the starting binding affinity of the parent antibody is such that such randomly produced antibody mutants can be readily screened.

One useful procedure for generating such antibody mutants is called "alanine scanning mutagenesis" (Cunningham and Wells (1989) Science 244:1081-1085). Here, one or more of the hypervariable region residue(s) are replaced by alanine or polyalanine residue(s) to affect the interaction of the amino acids with the antigen from the second mammalian species. Those hypervariable region residue(s) demonstrating functional sensitivity to the substitutions then are refined by introducing further or other mutations at or for the sites of substitution. The ala-mutants produced this way are screened for their biological activity as described herein.

Antibodies of the invention can be prepared by standard means.

For preparation of immunizing antigen, and polyclonal and monoclonal antibody production see, e.g., Kohler et al., Nature 256:495-497 (1975) and Eur. J. Immunol. 6:511-519 (1976); Milstein et al., Nature 266:550-552 (1977); Koprowski et al., U.S. Pat. No. 4,172,124; Harlow and Lane, "Antibodies: A Laboratory Manual," (Cold Spring Harbor Laboratory: Cold Spring Harbor, N.Y., 1988); and "Current Protocols In Molecular Biology," (Ausubel et al., Eds.; John Wiley & Sons: New York, N.Y., 1991); Kozbar et al., Immunology Today 4:72 (1983)), Cole et al., "Monoclonal Antibodies and Cancer Therapy" (Alan R. Liss, Inc. pp. 77-96 (1985)). Cells which produce antibodies with the desired specificity can be selected by a suitable assay (e.g., ELISA).

The antibodies of the invention can be also produced recombinantly, using well-known techniques. See, e.g., Cabilly et al., U.S. Pat. No. 4,816,567; Winter, U.S. Pat. No. 5,225,539. A nucleic acid encoding a desired antigen can be isolated or synthesized using conventional procedures and inserted into a replicable vector for further cloning or for expression.

When using recombinant techniques, the antibody can be produced intracellularly, in the periplasmic space, or directly secreted into the medium and further isolated and purified using known techniques such as, for example, hydroxylapatite chromatography, gel electrophoresis, dialysis, and affinity chromatography. Protein A affinity chromatography can be used to purify antibodies that are based on human γ1, γ2, or γ4 heavy chains (Lindmark et al. (1983) J. Immunol. Meth. 62:1-13). Protein G affinity chromatography can be used for mouse isotypes and for human γ3 (Guss et al. (1986) EMBO J. 5:15671575).

The various portions of chimeric, humanized, primatized (CDR-grafted) antibodies, or CDR-grafted single chain antibodies, comprising portions derived from different species, can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger et al., WO 86/01533; Neuberger et al., European Patent No. 0,194,276 B1; Winter, U.S. Pat. No. 5,225,539; and Winter, European Patent No. 0,239,400 B1. See also, Newman et al., *BioTechnology* 10:1455-1460 (1992), regarding primatized antibody and Ladner et al., U.S. Pat. No. 4,946,778 and Bird et al., Science 242:423-426 (1988)), regarding single chain antibodies. Nucleic acid (e.g., DNA) sequences coding for humanized variable regions can be constructed using PCR mutagenesis methods to alter DNA sequences encoding a human or humanized chain, such as a DNA template from a previously humanized variable region (see, e.g., Kamman et al., Nucl. Acids Res., 17:5404 (1989)); Sato et al., Cancer Research 53:851-856 (1993); Daugherty et al., Nucleic Acids Res. 19(9):2471-2476 (1991); and Lewis and Crowe, Gene 101:297-302 (1991)). Using these or other suitable methods, variants can also be readily produced. In one embodiment, cloned variable regions can be mutagenized, and sequences encoding variants with the desired specificity can be selected (e.g., from a phage library; see, e.g., Krebber et al., U.S. Pat. No. 5,514,548; and Hoogenboom et al., WO 93/06213). The entire content of each of which references is incorporated herein by reference.

In addition, functional fragments of antibodies, including fragments of chimeric, humanized, primatized, or single chain antibodies can also be produced. Functional fragments of the subject antibodies retain at least one binding function and/or modulation function of the full-length antibody from which they are derived. As mentioned herein above, useful antibody fragments include, but are not limited to, Fv, Fab, Fab' and F(ab')$_2$ fragments. Such fragments can be produced by enzymatic cleavage or by recombinant techniques. For instance, papain or pepsin cleavage can generate Fab or F(ab')$_2$ fragments, respectively. Antibodies can also be produced in a variety of truncated forms using antibody genes in which one or more stop codons has been introduced upstream of the natural stop site. For example, a chimeric gene encoding a F(ab')$_2$ heavy chain portion can be designed to include DNA sequences encoding the CH1 domain and hinge region of the heavy chain.

Other suitable methods of producing or isolating antibodies of the requisite specificity can be used, including, for example, methods which select recombinant antibody from a library, or which rely upon immunization of transgenic animals (e.g., mice) capable of producing a full repertoire of human antibodies. See, e.g., Jakobovits et al., *Proc. Natl. Acad. Sci. USA* 90:2551-2555 (1993); Jakobovits et al., *Nature* 362:255-258 (1993); Lonberg et al., U.S. Pat. No. 5,545,806; Surani et al., U.S. Pat. No. 5,545,807; Cabilly et al., U.S. Pat. No. 4,816,567; Cabilly et al., European Patent No. 0,125,023 B1; Queen et al., European Patent No. 0,451,216 B1; Boss et al., U.S. Pat. No. 4,816,397; Boss et al., European Patent No. 0,120,694 E1; Neuberger et al., WO 86/01533; Neuberger et al., European Patent No. 0,194,276 B1; Winter, U.S. Pat. No. 5,225,539; Winter, European Patent No. 0,239,400 B1; and Padlan et al., European Patent Application No. 0,519,596 A1. See, also, Ladner et al., U.S. Pat. No. 4,946,778; Huston, U.S. Pat. No. 5,476,786; and Bird et al., *Science* 242: 423-426 (1988).

In certain embodiments, the antibodies or antigen binding fragments of the antibodies can be labeled or unlabeled and used for diagnostic purposes. Typically, diagnostic assays entail detecting the formation of a complex resulting from the binding of an antibody to its target. The antibodies can be directly labeled with, for example, a radionuclide, a fluorophore, an enzyme, an enzyme substrate, an enzyme cofactor, an enzyme inhibitor, and a ligand (e.g., biotin or a hapten). Numerous appropriate immunoassays are known to the skilled artisan (see, e.g., U.S. Pat. Nos. 3,817,827; 3,850,752; 3,901,654; and 4,098,876).

Pharmaceutical compositions comprising the antibodies of the invention can be prepared by mixing the antibody having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG).

The pharmaceutical compositions comprising the antibodies of the invention may also contain one or more additional active compounds as necessary for the particular indication being treated, preferably those with complementary activities that do not adversely affect each other. Various active agents can be present in combination in amounts that are effective for the purpose intended.

The active ingredients may be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Sustained-release preparations may be also prepared. Suitable examples of sustained-release preparations include semipermeable matrices of solid hydrophobic polymers containing the antibody, which matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(–)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

For the treatment of a disease (e.g., IBD), the appropriate dosage of antibody of the invention will depend on the type of disease to be treated, the severity and course of the disease, whether the antibody is administered for preventive or therapeutic purposes, previous therapy, the patient's clinical history and response to the antibody, and the discretion of the attending physician. The antibody can be administered to the patient at one time or over a series of treatments. The progress of the therapy of the invention can be easily monitored by conventional techniques and assays.

The administration of antibodies of the invention can be performed by any suitable route, including systemic administration and in a particular embodiment, are administered directly to the site of the disease (e.g., to the small and/or large intestine).

As used herein, the term "antibody" encompasses immunoglobulins of different classes (i.e., IgA, IgG, IgM, IgD, and IgE) and subclasses (such as IgG1, IgG2 etc.) and includes, without limitation, chimeric antibodies, single-domain antibodies (sdAb, Nanobody), single chain antibodies, humanized antibodies, antibody fragments (e.g., Fab, F(ab')$_2$, Fv, scFv fragments), single domain antibodies, single variable domain antibodies, immunoglobulin single variable domain (e.g., comprising merely one variable domain $V_H$ or $V_L$ or larger polypeptides that comprise one or more monomers of an antibody single variable domain polypeptide sequence), monoclonal antibodies and polyclonal antibodies.

Techniques for the production of antibodies are well known in the art and described, e.g. in Harlow and Lane "Antibodies, A Laboratory Manual", Cold Spring Harbor Laboratory Press, 1988 and Harlow and Lane "Using Antibodies: A Laboratory Manual" Cold Spring Harbor Laboratory Press, 1999. The entire content of each of which references is incorporated herein by reference.

The antibodies of the invention can also be either full length antibodies or single-domain antibodies. In one specific embodiment, the antibody is a single-domain antibody contains an antibody fragment consisting of a single monomeric variable antibody domain, and lacking the light chain and CH1 domain of the heavy chain. For instance, the single domain antibodies contain VHH fragments which are engineered from heavy chain antibodies in camelids, e.g., dromedaries, camels, llamas and alpacas.

In one specific embodiment, the invention provides VHH single domain anti-DR3 antibodies. The small size (about 15 kD) of these antibodies allows them to fit into epitopes that are normally not accessible to traditional antibodies and also enables such antibodies to penetrate tissues faster, even readily crossing the blood-brain barrier (BBB). Moreover, the camelid (e.g., llama) VHH single domain antibodies are extremely stable and are resistant to both high acidity and temperature, even being able to fold back into a functional protein after denaturation.

Therefore, if appearing herein, the following terms shall have the definitions set out below.

The subject or patient is preferably an animal, including but not limited to animals such as mice, rats, cows, pigs, horses, chickens, cats, dogs, etc., and is preferably a mammal, more preferably a primate, and most preferably a human.

The term "preventing" or "prevention" refers to a reduction in risk of acquiring or developing a disease or disorder (i.e., causing at least one of the clinical symptoms of the disease not to develop in a subject that may be exposed to a disease-causing agent, or predisposed to the disease in advance of disease onset).

The term "prophylaxis" is related to "prevention" and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

The term "treating" or "treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term fecal transplant refers to fecal bacteria purified and isolated from an individual (e.g., a healthy individual or an individual with IBD such, e.g. Donor 2 described herein) and thereby processed by the hand of man, which is transplanted into a recipient. In a particular embodiment, the fecal transplant is manmade processed fecal material (fecal filtrate) having reduced volume and/or fecal aroma relative to unprocessed fecal material. In a more particular embodiment, the fecal transplant is a fecal bacterial sample. The term fecal transplant may also be used to refer to the process of transplantation of fecal bacteria isolated from a donor individual into a recipient. It is also referred to as fecal microbiota transplantation (FMT), stool transplant or bacteriotherapy.

As used herein, the term fecal bacterial sample refers to an essentially pure or purified bacterial population (e.g., a paste thereof), which is purified from feces and thus, is essentially free of fibrous fecal material that is normally associated with feces in a natural state prior to manipulation by the hand of man.

As used herein, the term healthy donor refers to individuals without history of any chronic medical condition.

As used herein, the term pure or purified bacterial species refers to a monoculture of a single bacterial species that consists essentially of or consists of only bacterial cells of the indicated species. In other words, a pure or purified bacterial species is essentially devoid of bacterial cells of other different bacterial species.

As used herein, the term "immune response" signifies any reaction produced by an antigen, such as a protein antigen, in a host having a functioning immune system. Immune responses may be either humoral, involving production of immunoglobulins or antibodies, or cellular, involving various types of B and T lymphocytes, dendritic cells, macrophages, antigen presenting cells and the like, or both. Immune responses may also involve the production or elaboration of various effector molecules such as cytokines, lymphokines and the like. Immune responses may be measured both in in vitro and in various cellular or animal systems.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest. As described herein, an immunological response also encompasses responses of innate immune cells such as, for example, ILC3s.

The phrase "pharmaceutically acceptable" refers to molecular entities and compositions that are physiologically tolerable and do not typically produce an allergic or similar untoward reaction, such as gastric upset, dizziness and the like, when administered to a human. The phrase "physiologically compatible" refers to molecular entities and compositions that do not alter to a significant degree biological processes.

The phrase "therapeutically effective amount" is used herein to mean an amount sufficient to preferably reduce by at least about 30 percent, more preferably by at least 50 percent, most preferably by at least 90 percent, a clinically significant change in a pathological feature of a disease or condition. In an embodiment thereof, a therapeutically effective amount of a bacterial population, including an essentially pure or purified population of a particular bacterial species or a combination of at least two essentially pure or purified populations of bacterial species, is $10^6$ to $10^{12}$ colony forming units (cfu). Such a therapeutically effective amount may be administered or used at a concentration of $10^6$ to $10^{12}$ cfu/ml and at a dose of 1 ml/100 g body weight for a small animal, such as a mouse or rat. In a further embodiment thereof, $10^8$ cfu/ml is administered or used at a dose of 1 ml/100 g body weight for a small animal. Such dosing parameters can be scaled up for larger animals, including humans, using standard means known in the art.

Compositions containing molecules or compounds described herein can be administered for therapeutic purposes. In therapeutic applications, compositions are administered to a subject afflicted with IBD (e.g., Crohn's disease or ulcerative colitis) in an amount sufficient to at least partially arrest the symptoms of the disease and its complications. In a particular embodiment, such an amount is sufficient to promote mucosal healing in the small and/or large intestine of such subjects. An amount adequate to accomplish this is defined as a "therapeutically effective amount or dose." Amounts effective for this use will depend on the severity of the disease and the weight and general state of the patient.

Also encompassed herein are therapeutic compositions useful for practicing the therapeutic methods described herein. A subject therapeutic composition may include, in admixture, a sterile manmade pharmaceutically acceptable or physiologically compatible excipient (carrier) and one or more of an agent as an active ingredient (e.g., recombinant TL1A or a recombinant agonistic DR3 antibody or a purified bacterial species or at least one purified bacterial species), which promotes mucosal healing by directly or indirectly inducing ILC3s to secrete IL-22 and GM-CSF, as described herein. Compositions wherein the active ingredient is a purified bacterial species (monoculture) or at least one purified bacterial species comprise, in addition to the active ingredient, a sterile manmade pharmaceutically acceptable or physiologically compatible excipient or carrier. In accordance with same, the purity of the composition with regard to the bacterial content is maintained and preserved.

The preparation of therapeutic compositions which contain polypeptides, analogs or active fragments as active ingredients is well understood in the art. Typically, such compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic polypeptide-, analog- or active fragment-containing compositions are conventionally administered intravenously, as by injection of a unit dose, for example. In a particular embodiment, however, therapeutic polypeptide-, analog- or active fragment-containing compositions are administered orally for specific release of the therapeutic agents in the small and/or large intestine or administered anally for direct delivery to the small and/or large intestine. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or cell modulation desired. Precise amounts of active ingredient required to be administered depend on the judgment of the practitioner and are peculiar to each individual. However, suitable dosages may range from about 0.1 to 20, preferably about 0.5 to about 10, and more preferably one to several milligrams of active ingredient per kilogram body weight of individual per day and depend on the route of administration. Suitable regimes for initial administration and booster shots are also variable, but are typified by an initial administration followed by repeated doses at one or more hour intervals by a subsequent injection or other administration. Alternatively, continuous intravenous infusion sufficient to maintain concentrations of ten nanomolar to ten micromolar in the blood are contemplated.

A general method for site-specific incorporation of unnatural amino acids into proteins is described in Christopher J. Noren, Spencer J. Anthony-Cahill, Michael C. Griffith, Peter G. Schultz, *Science,* 244:182-188 (April 1989). This method may be used to create analogs with unnatural amino acids.

As used herein, the term "complementary" refers to two DNA strands that exhibit substantial normal base pairing characteristics. Complementary DNA may, however, contain one or more mismatches.

The term "hybridization" refers to the hydrogen bonding that occurs between two complementary DNA strands.

"Nucleic acid" or a "nucleic acid molecule" as used herein refers to any DNA or RNA molecule, either single or double stranded and, if single stranded, the molecule of its complementary sequence in either linear or circular form. In discussing nucleic acid molecules, a sequence or structure of a particular nucleic acid molecule may be described herein according to the normal convention of providing the sequence in the 5' to 3' direction. With reference to nucleic acids of the invention, the term "isolated nucleic acid" is sometimes used. This term, when applied to DNA, refers to a DNA molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or host organism. In a particular embodiment, the isolated nucleic acid sequence is a cDNA.

When applied to RNA, the term "isolated nucleic acid" refers primarily to an RNA molecule encoded by an isolated DNA molecule as defined above. Alternatively, the term may refer to an RNA molecule that has been sufficiently separated from other nucleic acids with which it is generally associated in its natural state (i.e., in cells or tissues). An isolated nucleic acid (either DNA or RNA) may further represent a molecule produced directly by biological or synthetic means and separated from other components present during its production.

The phrase "consisting essentially of" when referring to a particular nucleotide or amino acid means a sequence having the properties of a given SEQ ID NO: For example, when used in reference to an amino acid sequence, the phrase includes the sequence per se and molecular modifications that would not affect the basic and novel characteristics of the sequence. When referring to a composition comprising a bacterial species, for example, the composition may consist essentially of the bacterial species, thereby indicating the population of the bacterial species in the composition is present in the absence of other bacterial species or exists as a purified or pure population (monoculture) of the bacterial species in question. When referring to a composition consisting essentially of or consisting of more than one purified population of a bacterial species, the mixture of bacterial species monocultures that were combined in the composition exists in the absence of other bacterial species. By way of example, a composition that consists essentially of bacterial species A, B, and C does not include any bacterial cells of other (non-A, -B, or -C) bacterial species.

A "replicon" is any genetic element, for example, a plasmid, cosmid, bacmid, phage or virus that is capable of replication largely under its own control. A replicon may be either RNA or DNA and may be single or double stranded.

A "vector" is a replicon, such as a plasmid, cosmid, bacmid, phage or virus, to which another genetic sequence or element (either DNA or RNA) may be attached so as to bring about the replication of the attached sequence or element.

An "expression vector" or "expression operon" refers to a nucleic acid segment that may possess transcriptional and translational control sequences, such as promoters, enhancers, translational start signals (e.g., ATG or AUG codons), polyadenylation signals, terminators, and the like, which facilitate the expression of a polypeptide coding sequence in a host cell or organism.

As used herein, the term "operably linked" refers to a regulatory sequence capable of mediating the expression of a coding sequence, which is placed in a DNA molecule (e.g., an expression vector) in an appropriate position relative to the coding sequence so as to effect expression of the coding sequence. This same definition is sometimes applied to the arrangement of coding sequences and transcription control elements (e.g. promoters, enhancers, and termination elements) in an expression vector. This definition is also sometimes applied to the arrangement of nucleic acid sequences of a first and a second nucleic acid molecule wherein a hybrid nucleic acid molecule is generated.

The term "oligonucleotide," as used herein refers to a primer and a probe as described herein and is defined as a nucleic acid molecule comprised of two or more ribo- or deoxyribonucleotides, preferably more than three. The exact size of the oligonucleotide will depend on various factors and on the particular application and use of the oligonucleotide.

By "solid phase support or carrier" is intended any support capable of binding an oligonucleotide, polypeptide, antigen, or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present methods and/or compositions. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art are aware of many other suitable carriers for binding oligonucleotide, polypeptide, antibody, or antigen, and are able to ascertain the same by use of routine experimentation. In an embodiment of the present methods, therapeutic agents described herein are administered to a subject in need thereof as conjugates. Therapeutic agents may, for example, be conjugated or attached to beads to generate conjugates that are better suited to specific delivery in the small and/or large intestine and/or achieve better presentation of a therapeutic agent, for example, TL1A to ILC3s. With regard to presentation, multivalent presentation such as that achieved by conjugation to beads is known to induce amplified cell responses to conjugated agents.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contain the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The following examples are provided to further illustrate the disclosure and are not intended to be restrictive in any way.

Example 1

Materials and Methods

Antibodies and Flow Cytometry.

Staining of human cells was performed with c-Kit-e450 (104D2), CD56-PECy5.5 (CMSSB), HLA-DR-PE (LN3), CD11c-FITC (3.9), CD3-e780 (UCHT1), CD19-PerCP5.5 (HIB19), CD103 PECy7 (B-Ly7), CD14 PE (61D3), CD86-PE (IT2.2), CD123 PE (6H6), CD11b PE (CBRM1/5) and RORγt (AFKJS-9) from eBiosciences; CD161-FITC, CD83-PE, CD11c PE (555392), CD127 FITC (M21), CCR6-biotin (11A9) are from BD Biosciences; BDCA-1-APC is from Milteny Biotec; CD45-APC (4505) and CD64 (6404) are from Caltag; NKp44-APC (p44-8.1) is from R&D Systems; and BDCA-3 APC (M80) is from Biolegend. Intracellular human cytokine staining was performed with IL-22 PE (IC7821P; R&D), IL-17A-FITC (eBio64CAP17; eBioscience), or IFNγ (45.B3; eBioscience). Staining of mouse cells was performed with CD90.2-e450 (53-2.1), CD3e (145-2C11), NKp46-e710 (29A1.4), RORγt-PE (B2D), CD11c-PECy7 (N418), MHCII A700 (M5/114.15.2), CD103 APC (2E7), CD14 PerCP5.5 (Sa2-8), CD11b e780 (M1/70), Ly6C PerCP5.5 (AL-21) and F4/80 PE (BM8) were from eBiosciences. DR3-PE (4C12) was from Biolegend. Intracellular mouse cytokine staining was performed with IL-22 APC (IL22JOP), IFNγ PECy7 (XMG1.2), IL17A FITC (eBio17B7), all from eBiosciences. Intracellular cytokine staining was performed according to the manufacturer's protocol (Cytofix/Cytoperm buffer set from BD). Intranuclear staining for RORγt was performed according to manufacturer's protocol (Intracellular Fixation and Permeabilization Kit from eBiosciences). Flow cytometry and analysis were performed with a LSR II (BD Biosciences) and FlowJo software (Tree Star). Dead cells were excluded using the Live/Dead fixable aqua dead cell stain kit (Invitrogen).

Mice.

C57BL/6, Myd88$^{flox}$ (JAX #008888), CD11c-cre (JAX #008068), and Il1r$^{-/-}$ (JAX #003245) mice were purchased from Jackson Laboratories. Myd88-deficient mice, were according to Adachi et al. (1998, Immunity, 9:143-150), and Il23p19$^{-/-}$ mice were according to Cua et al. (2003, Nature, 421:744-748). RORc(γt)$^{GFP/+}$ were according to Eberl et al. (2004, Nat Immunol, 5:64-73), Cx3cr1$^{GFP/+}$ were according to Jung et al. (2000, Mol. Cell Biol., 20:4106-4114), and inducible CX$_3$CR1-DTR mice were according to Diehl et al. (2013, Nature, 494:116-120). The latter mice were subsequently bred to a germline-expressing cre mouse to excise the transcriptional stop sequence and produce the Cx$_3$cr1$^{DTR/+}$ mice. All mice were kept in specific pathogen-free (SPF) conditions at the animal facility of the Skirball Institute. Mouse experiments were performed with at least 3 mice per group and multiple experiments were combined to assess statistically significant differences as noted. Littermates of the same genotype were randomly assigned to experimental groups. Animals were used between 8-16 weeks of age. Males and females were used in approximately equal ratios. All animal experiments were performed in accordance with approved protocols for the NYU Institutional Animal Care and Usage Committee.

Preparation of LPMCs.

Endoscopic biopsies were obtained under IRB-approved protocols at Weill Cornell Medical College (1103011578) and Columbia University Medical Center (AAAE5448) including patients >18 years of age and able to give informed consent. IBD sample was defined based on endoscopic inflammation with history of Crohns' disease or ulcerative colitis. Endoscopic score (Mild, Moderate, or Severe) was based on Mayo Endoscopic subscore or SES-CD (1, 2, 3, respectively) at the site of biopsy (Pineton de Chambrun et al. (2010, Nat Rev Gastroenterol Hepatol 7:15-29). All endoscopic biopsies were taken from the sigmoid or descending colon in order to reduce sampling variation. Study sample sizes for human biopsies were based on preliminary data and powered to achieve statistically significant differences in the production of IL-22 or IL-17. Surgical resections were obtained under an IRB-approved protocol at New York University Langone Medical Center. Mouse and human intestines were washed in PBS, 1 mM DTT, twice with 30 mM EDTA, and then digested in collagenase 8 (Sigma) and DNase-containing media with 10% fetal bovine serum. Digested material was passed through a cell strainer and separated on a discontinuous 40%/80% Percoll gradient. LPMCs were cultured ex vivo in the presence of GolgiPlug (BD) for 4 hours or stimulated with phorbol myristate acetate (PMA; 20 ng/mL) and ionomycin (1 μg/mL) or IL-23 (40 ng/mL; eBioscience) in the presence of GolgiPlug (BD) for 4 hours before staining.

Intestinal ILC Cultures.

Surgical resections were obtained from the NYU Biorepository (Rachel Brody). Lineage negative, c-Kit$^+$ CD45$^{int}$ ILCs were sorted and cultured in tissue culture media (RPMI 1640 (Invitrogen) supplemented with 10% (vol/vol) heat-inactivated FBS (Hyclone), 50 U penicillin-streptomycin (Invitrogen), 2 mM glutamine, and 50 μM β-mercaptoethanol), supplemented with IL-7 (50 ng/mL; Peprotech) and IL-2 (1,000 U/mL; peprotech) for 8-10 days prior to stimulation. Lineage negative, CD90.2$^+$, RORγt-GFP mouse ILC3 were sorted from LPMCs and resuspended in RPMI-based tissue culture media for stimulation directly ex vivo. Human and mouse ILCs were stimulated with human or mouse IL-23 (eBiosciences, 40 ng/mL), IL-1β (eBiosciences, 10 ng/mL), or TL1A (R and D systems, 200 ng/mL) as indicated, respectively. After 18 hours, supernatants were harvested for IL-22 ELISA (eBiosciences) and Golgi Plug (BD biosciences) was added to cells for 4 hours for subsequent intracellular cytokine staining.

Co-Culture Assay.

ILCs and APC populations were sorted on a FACS Aria and co-cultured with 5×10$^3$ and 2.5×10$^3$ cells, respectively, in 96-well round bottom plates in tissue culture media. TLR stimulation was performed with 1 μg/mL LPS (E. coli, Sigma), 1 μM CpG 1668 (Mouse), 1 μM CpG 2216 (Human) or 1 μg/mL flagellin (Salmonella Typhi, InvivoGen). Cultures were incubated for 18 hours. Supernatants were harvested for ELISA and remaining cells were incubated with Golgi Plug (BD Biosciences) for 4 hours and subsequently analyzed by flow cytometry.

siRNA Transfection.

Sorted intestinal ILCs were cultured overnight in IL-7 (20 ng/mL) and SCF (20 ng/mL). After 24 hours, 4×10$^5$ ILCs were transfected using AMAXA T cell nucleofection protocol. 300 pmol of Tnfrsf25 siRNA pool or scramble control (Dharmacon) was used per transfection. Cells were rested overnight and harvested at 24 hours for experimental use. Knockdown efficiency was assessed at 24 hours by DR3 surface staining.

Colitis Models.

*Citrobacter rodentium* DBS100 (ATCC 51459; American Type Culture Collection) was harvested at log phase growth and $10^{10}$ cfu were delivered by gavage in PBS. 200 ng of diphtheria toxin was administered i.p. as indicated for depletion. Plasmid DNA expressing IL-22 or control plasmid were delivered i.v. at 5 μg DNA/mouse diluted in TransIT-EE Hydrodynamic Delivery Solution (Mirus) at 0.1 ml/g body weight. Immune cell functional analysis and histology were performed at day 8 following exposure. Spleens were harvested on day 21, homogenized, and plated at serial dilutions to determine cfu/spleen.

RNA-Seq Processing and Gene Set Enrichment Analysis.

Sequence reads were mapped to the human genome (version hg19) by Tophat (version 2.0.6), using Bowtie2 (version 2.0.2) and Samtools (version 0.1.18). Reads are deposited at Bioproject PRJNA219394. Reads mapped per transcript served as input to DESeq (version 1.12.0), an R package that calculates differential gene expression. To improve detection of APC lineage-dependent gene-expression changes and overcome donor-dependent variability, we used the following strategy: independently for each donor, differential gene expression, comparing $CD103^+$ to $CD14^+$ human myeloid cells, was estimated using the negative binomial distribution ("nbinomTest"), and then results from biological replicates were combined using Fisher's method. Several gene-set-enrichment techniques (e.g., hypergeometric test, area under precision-recall curve) were used to test whether specific gene sets were significantly differentially regulated between the two lineages. The GWAS gene sets are derived from disease-associated SNPs from the NHGRI GWAS Catalog. False-discovery rates (FDRs) were calculated using the Benjamini-Hochburg procedure. The enrichment analyses were implemented in Matlab R2013a (8.1.0.604).

qPCR.

RNA from primary intestinal APCs stimulated as indicated was prepared with Trizol (Invitrogen). RNA was reverse transcribed into cDNA (SuperScript III; Invitrogen) and QPCR was performed with a Roche Lightcycler with SYBR Green Supermix (Bio-Rad), 20 pmol forward and reverse primers, and 0.1 μg of cDNA from. 5'-TGTTC-CCCATATCCAGTGTGG-3' (SEQ ID NO: 6) and 5'-CTG-GAGGCTGCGAAGGATTT-3' (SEQ ID NO: 7) for p19, 5'-ATGCTTCGGGCCATAACAGA-3' (SEQ ID NO: 8) and 5'-TGAAGGCCATCCCTAGGTCA-3' (SEQ ID NO: 9) for TL1A, and 5'-ACCACAGTCCATGCCATCAC-3' (SEQ ID NO: 10) and 5'-TCCACCACCCTGTTGCTGTA-3' (SEQ ID NO: 11) for GAPDH. The thermocycling program was 40 cycles at 95° C. for 15 s, 60° C. for 30 s, and 72° C. for 30 s, with an initial cycle of 95° C. for 2 min. Relative levels of target gene were determined by using the delta $C_t$ value compared to delta $C_t$ (GAPDH).

Immunofluorescence. Intestinal tissue was Swiss-rolled before fixing for 4 hours in 4% paraformaldehyde. Tissue was incubated overnight in 30% sucrose before freezing in OCT. Tissue was cut into 5 uM sections. Tissue was blocked in PBS-XG (0.1% Triton X-100, 10% goat serum) before incubating overnight in primary antibody in PBS-XG. Tissue was washed and then incubated with secondary antibody for 1 h before DAPI staining Primary antibodies are from Ebioscience: Anti-Human/Mouse RORγt (clone AFKJS-9) and Anti-Mouse CD3e (clone 145-2C11). Secondary antibodies are from Jackson ImmunoResearch (Cy3-AffiniPure Goat Anti-Rat IgG and Goat Anti-Armenian Hamster). Tissue was imaged using an LSM 710 confocal (Carl Zeiss) and images were processed using Image J.

Results $CX_3CR1^+$ Cells Protect Against *C. rodentium*-Induced Colitis

To investigate the role of the expanded population of $CX_3CR1^+$ cells in the intestinal lamina propria during colitis, we generated a mouse with the diphtheria toxin receptor (DTR) cDNA inserted into the Cx3cr1 locus. Analysis of colonic lamina propria mononuclear cells (LPMCs) following infection of DT-treated mice revealed a reduction in the percentage of $CD11c^+$ $MHCII^+$ LPMCs (FIG. 1A), which reflected a preferential loss of the $CX_3CR1^+$ $CD11b^+$ $CD14^+$ fraction of MNPs (FIG. 1B) as well as $CX_3CR1^+$ monocytes in Cx3cr1$^{DTR/+}$ mice compared to control mice. $CD103^+$ $CD11b^+$ cDCs were not depleted (FIG. 1C). In order to induce colitis, mice were infected with *C. rodentium*, a mouse model for infectious colitis. DT-treated infected Cx3cr1$^{DTR/+}$ mice, but not uninfected or control infected mice, lost more weight (FIG. 1D), displayed more severe intestinal pathology (FIG. 1E), and ultimately succumbed to infection (FIG. 1F). Infected Cx3cr1$^{DTR/+}$ mice also had increased bacterial burden in the spleen, consistent with the loss of barrier integrity (FIG. 1G).

To examine potential involvement of signaling pathways for receptors of pathogen- or microbe-associated molecular patterns (PAMPs or MAMPs) in mediating this phenotype, mice with a conditional deletion of MyD88 in CD11c-expressing MNPs (CR11c-Cre/Myd88$^{fl/fl}$) were infected with *C. rodentium*. Infection of CD11c-Cre/Myd88$^{fl/fl}$ mice, but not littermate controls, was lethal by 15 days post-infection (FIG. 2A), implicating PAMP/MAMP signaling as having a critical role in barrier protection mediated by CD11c-expressing MNPs. The *C. rodentium* colitis model depends on IL-22 for protection. Thus, in order to test if exogenous IL-22 could rescue the susceptibility phenotype described above, CD11c-Cre/Myd88$^{fl/fl}$ (FIG. 2A) and DT-treated $CX_3CR1$-DTR (FIG. 2B) mice were hydrodynamically injected with a plasmid encoding IL-22. The exogenous IL-22 rescued both lines of mice from colitis-induced death.

Colonic $CX_3CR1^+$ MNPs Regulate ILC3 Production of IL-22

High dose infection with *C. rodentium* is controlled by ILC3, which represent the large majority of LPMCs producing IL-22. At day 7 post-infection, both the percentage and absolute number of IL-22$^+$ colonic, lineage negative, $CD90^{hi}$, RORγt$^+$ ILCs (FIG. 10 for gating strategy) from mice depleted for $CX_3CR1^+$ cells were reduced in comparison to ILCs from mice with intact $CX_3CR1^+$ cells (FIG. 2C, D, E). Depletion of $CX_3CR1^+$ cells did not affect the absolute number of ILC3 (FIG. 2F). While T cells can also contribute to IL-22 production in low dose *C. rodentium* infection, no statistically significant difference in the total IL-22$^+$ (or IL-17$^+$) T cells was noted in mice depleted for $CX_3CR1^+$ cells (FIG. 2G). To assess the ability of colonic $CX_3CR1^+$ MNPs to interact with ILC3 within the colonic tissue, Cx3cr1$^{GFP/+}$ mice were used to visualize $CX_3CR1^+$ MNPs in situ. Consistent with the ability of these cells to regulate ILC3 function, confocal microscopy revealed the spatial proximity of RORγt$^+$ ILC3 cells with $CX_3CR1^+$ MNPs in the colonic lamina propria (FIG. 2H).

To evaluate the ability of intestinal $CX_3CR1^+$ cells and cDCs to support ILC3 activation, $CX_3CR1^+$ (GFP$^+$) cells and CD103+ CD11b+ DCs were sorted from the lamina propria of Cx3cr1$^{GFP/+}$ mice (FIG. 3A) and co-cultured with intestinal ILCs. TLR-stimulated CX$_3$CR1+ cells were markedly more efficient than CD103+ CD11b+ DCs in supporting IL-22 production (FIG. 3B, C). CX$_3$CR1+ cells in the LP include Ly6C$^{hi}$ monocytes and Ly6C$^{lo}$ MHCII$^{hi}$ MNPs (FIG. 3D and. To evaluate the role of these distinct CX$_3$CR1+ populations in supporting ILC3 function, we sorted CX$_3$CR1+ monocytes and CX$_3$CR1+ MNPs and co-cultured them with ILCs in the presence of TLR stimuli. TLR-stimulated MNPs were much more potent inducers of IL-22 than monocytes (FIG. 3E, F). In an effort to confirm the functional potential of MNPs compared to monocytes in vivo, we selectively ablated CD11c-expressing CX$_3$CR1+ MNPs. CD11c-cre mice were bred to mice engineered to express DTR only upon cre-mediated deletion of a LoxP-Stop cassette inserted into the Cx3cr1 locus. Injection of DT resulted in a selective loss of Ly6C$^{lo}$ MHCII$^{hi}$ MNPs, which express both intermediate and high levels of CX$_3$CR1-GFP, and spared the Ly6C$^{hi}$ monocytes, which express intermediate levels of CX$_3$CR1 (FIG. 4A). Similar to results with CX$_3$CR1$^{DTR/+}$ mice, in which both monocytes and MNPs were ablated, depletion of CX$_3$CR1+ CD11c+ cells led to reduction in colitis-induced ILC3 production of IL-22 (FIG. 4B).

Since both IL-23 and IL-1β regulate ILC3, we wished to determine the contribution of these cytokines to the observed regulation of IL-22 production by MNPs. LPS and CpG stimulation induced markedly increased IL-23 and IL-1β production by CX$_3$CR1+ MNPs compared to CD103+ CD11b+ DCs in vitro (FIG. 4C, D). In order to evaluate the role for MNP-derived IL-23 and IL-1β, co-cultures were performed with intestinal CD11c+ cells derived from WT or Il23p19$^{-/-}$ mice and ILCs from WT or Il1r$^{-/-}$ mice. IL-23-deficient MNPs and IL1R-deficient ILCs yielded significantly reduced production of IL-22 (FIG. 4E), consistent with the importance of MNP-derived IL-1β and IL-23 in supporting IL-22 production. These data reveal a mechanistic role for IL-23 and IL-1β produced by colonic MNPs in supporting colitis-associated ILC3 secretion of IL-22.

Human Intestinal ILC3 Production of IL-22 is Regulated by Microbial Stimulation of MNPs.

To evaluate the regulation of intestinal ILC3 in humans with IBD, we prepared LPMCs from descending colon biopsies of patients with endoscopically mild to moderate Crohns' disease (CD, N=8) or ulcerative colitis (UC, N=6) (FIG. 10) as well as age-matched non-IBD control patients undergoing routine screening colonoscopy (N=8). Analysis of intracellular cytokine production revealed significantly increased IL-22 production in the CD3$^-$ fraction of colonic LPMCs from sites of colonic inflammation in both CD and UC compared to the non-IBD controls (FIG. 5A, FIG. 11). In contrast, IL-22 production by T cells was not significantly different between the groups. Further characterization of the non-T cells producing IL-22 revealed that a large fraction of these cells expressed c-Kit and CD56, markers of ILCs (FIG. 5B). Consistent with their being ILC3, these cells were lineage negative (Lin$^-$) (FIG. 12A), expressed RORγt (FIG. 5C), were CD45$^{int}$ CD127+ (FIG. 5D), expressed CD161, NKp44, and CCR6 (FIG. 5E), which are phenotypic surface markers of ILC3, and produced IL-22 in response to IL-23 stimulation (FIG. 5F). As Myd88-deficiency abrogated ILC3 production of IL-22, we hypothesized that signals from the microbiota could induce ILC3 to produce IL-22. To investigate this in human tissue, we evaluated three patients who had a surgical diversion of the "fecal stream" (i.e. a diverting ostomy) as part of their therapy for IBD. Endoscopic biopsies were taken from a site proximal to the diversion (afferent limb), where the mucosa was exposed to intestinal microbiota in the fecal stream, and from mucosa distal to the diversion (efferent limb), that was unexposed to the fecal stream. ILCs were present at both mucosal locations, but not in PBMCs from the same donor (FIG. 12B). In all three donors, ILCs from tissue exposed to bacteria in the fecal stream produced substantially more IL-22 compared to ILCs from unexposed tissue (post-diversion) (FIG. 5G).

Parallel subpopulations of CD11c+ MNPs present in the mouse intestine similarly exist in the human intestine (FIG. 6A). To evaluate whether these distinct subpopulations of MNPs from human intestinal tissue functioned similarly, we examined the phenotypic properties of CD103+ DCs and CD14+ MNPs (which express CX$_3$CR1) within the CD11c+ MHCII+ fraction of LPMCs (FIG. 6B). In contrast to CD103+ DCs, CD14+ MNPs expressed CD64 as well as higher levels of CD86. Consistent with the phenotypic characterization of these subsets, transcriptional analysis of these populations by RNA-seq revealed higher levels of CLEC9A, XCR1, and CD207 expression in the CD103+ cells, while MERTK, STAB1, and CX3CR1 were higher in the CD14+ cells (FIG. 6C). We tested the potential of these subsets to induce IL-22 production by co-culturing TLR-stimulated CD14+ MNPs and CD103+ DCs from human intestinal resections with intestinal ILCs. Intracellular cytokine staining at 18 hours revealed that the CD14+ MNP were more effective than the CD103+ DCs at stimulating IL-22 production by ILCs (FIG. 6D). Neither cell population induced significant IL-17 or IFN production by ILCs (FIG. 6D, 6E).

Consistent with the importance of IL-23 and IL-1β in the mouse co-culture experiments, a higher level of IL23A expression was observed by RNA-seq in CD14+ MNPs compared to CD103+ DCs (FIG. 6C). Stimulation of these human MNP subsets with LPS or flagellin revealed increased IL-23p19 mRNA and IL-1β protein produced by the CD14+ cells compared to the CD103+ cells (FIG. 6F). In accord with this finding, in co-cultures of human intestinal ILC3 and CD14+ MNPs, IL-23 and IL-1β antibody blockade blunted IL-22 production (FIG. 6G). These data reveal a mechanistic role for the expanded population of CD14+ MNPs in supporting colitis-associated IL-22 production by ILC3, through their secretion of IL-23 and IL-1β.

CX$_3$CR1+ MNP-Derived TL1A Synergizes with IL-23 and IL-1β to Induce IL-22.

We hypothesized that MNP-derived factors in addition to IL-23 and IL-1β would contribute to the regulation of ILC3 function. The RNA-seq data from CD14+ human MNPs revealed a significant enrichment for genes associated with IBD in GWAS studies, suggesting that IBD-associated pathways are important in these cells (FIG. 7A, FIG. 11). Notably, we identified TNF-like ligand 1A (TL1A, also designated TNFSF15) as a significant contributor to the IBD GWAS-derived gene set enrichment. Evaluation of Tnfsf15 transcript in sorted mouse colonic APC subsets by qPCR confirmed higher expression in CX$_3$CR1+ MNPs (FIG. 7B). Ex vivo stimulation with mouse or human recombinant TL1A significantly enhanced the ability of IL-23 and IL-1β to induce IL-22 by both mouse (FIG. 7C, FIG. 13) and human (FIG. 7D) intestinal ILC3, respectively. TL1A and IL-1β additionally cooperated in inducing GM-CSF production by mouse ILC3 (FIG. 7E). In order to assess the specificity of TL1A for DR3/TNFRSF25 on ILCs and its functional role in enhancing CX$_3$CR1+ support of ILC3 activation, DR3 expression was specifically knocked down using siRNA nucleofection of sorted mouse intestinal ILC3.

Efficiency of knock-down was confirmed by surface staining for DR3, comparing with a scrambled control siRNA (FIG. 7F). Compared to the scramble control, cells targeted with siRNA for Tnfrsf25 had significantly reduced enhancement of IL-22 production upon treatment with recombinant TL1A (FIG. 7G, 7H). The targeted ILCs also produced reduced amounts of IL-22 upon co-culture with LPS-stimulated $CX_3CR1^+$ MNPs. These data reveal a potent ability of TL1A to enhance IL-22 production via DR3/TNFRSF25 on ILC3 in both mouse and human.

Discussion

Mononuclear phagocytes are spatially and functionally poised to integrate microbial signals from the luminal microbiota (Niess et al., 2005; Varol et al., 2010). Although MNPs were previously thought to remain in the tissue, we recently showed that $CX_3CR1^+$ MNPs can migrate to draining lymph nodes and initiate immune responses under conditions of dysbiosis (Diehl et al., 2013). In the context of inflammation, however, these $CX_3CR1^+$ MNPs expand within the lamina propria during chemical (Zigmond et al., 2012) or infectious colitis and in IBD patients (Kamada et al., 2008), and their function has remained obscure. Conventional DCs (cDCs), rather than the MNPs, have been postulated to regulate intestinal Th17 cell differentiation in response to microbiota (Denning et al., 2011; Goto et al., 2014; Lewis et al., 2011; Persson et al., 2013; Schlitzer et al., 2013), but there has been conflicting evidence as to which myeloid cell populations regulate IL-22 production by ILC3 cells (Kinnebrew et al., 2012; Manta et al., 2013; Satpathy et al., 2013).

Our data reveal that colonic $CX_3CR1^+$ MNPs regulate ILC3 production of IL-22 and likely play a critical role in promoting mucosal healing during colitis. The requirement for $CX_3CR1^+$ MNPs in regulating colitis-induced ILC3 shown here appears to contrast with recent work suggesting that Notch2-dependent $CD103^+$ $CD11b^+$ cDCs are required for the control of C. rodentium-induced colitis (Satpathy et al., 2013). These disparate results may reflect a coordinated contribution of multiple myeloid subsets in the immune response to C. rodentium (Schreiber et al., 2013) and our data do not exclude a contribution of other myeloid subsets. Alternatively, Notch2 may affect cellular subpopulations in addition to $CD103^+$ $CD11b^+$ cDCs. This latter hypothesis is supported by the report that an alternate selective depletion strategy for $CD103^+$ $CD11b^+$ cDCs, by expression of diphtheria toxin under the human Langerin promoter (Welty et al., 2013), did not result in increased susceptibility to C. rodentium. Some of the conflicting data may additionally reflect differential roles of inflammatory monocytes and MNPs in colitis. Inflammatory monocytes may exacerbate pathology, as antibody-mediated depletion of $Ly6C^{hi}$ monocytes during DSS treatment improved pathology in DSS colitis (Zigmond et al., 2012). Selective depletion of such monocytes may hence explain the intermediate results seen in the CCR2-deficient mice exposed to C. rodentium (Satpathy et al., 2013). In addition to supporting ILC3, MNPs may also directly promote epithelial barrier repair (Wynn et al., 2013). While our data suggest a critical role for $CX_3CR1^+$ MNPs in regulating production of IL-22 by ILC3 during acute colitis, it will be important to examine the role for these myeloid subsets during chronic colitis and their impact on another major clinical endpoint in IBD—tumorigenesis (Huber et al., 2012; Kirchberger et al., 2013).

Our results also highlight a beneficial role for microbial signals in promoting intestinal homeostasis and driving ILC3 production of IL-22 through TLR/MyD88-dependent induction of IL-23 and IL-1β. At the steady state, commensal-dependent signaling may negatively regulate ILC production of IL-22 via intestinal epithelial cell production of IL-25 (Sawa et al., 2011), but we and others (Satoh-Takayama et al., 2008) find that microbes support colitis-associated ILC production of IL-22, which promotes mucosal healing. Although intravenous delivery of flagellin can induce $CD103^+$ $CD11b^+$ cDC to produce IL-23 that regulates ILC3 in the small intestine (Kinnebrew et al., 2012), we and others (Kamada et al., 2008) found that in vivo colonic inflammation and other bacterial-derived signals induced more robust production of IL-23 and IL-1β by MNPs, suggesting that the type of stimulation and/or colonic inflammation may confer specificity. Similar to our results in mice, we found marked reductions in IL-22 production by intestinal ILC3 from human tissue distal to a surgical diversion of the fecal stream. These findings may offer clinically relevant mechanistic insight into diverted IBD patients with persistent inflammatory disease or even non-IBD patients with de novo mucosal inflammation following diversion (e.g. diversion colitis (Harig et al., 1989)). While some evidence supports a role for luminal replacement of short chain fatty acids in diversion colitis (Harig et al., 1989; Vernia et al., 1995), further work is required to determine if particular metabolites or intestinal microbes may regulate ILC3 function to promote healing.

In light of their robust production of IL-22 and close proximity to the intestinal epithelial layer (Cella et al., 2009), ILC3 have been proposed to play an important role in mucosal healing and maintenance of barrier integrity, but their characterization in IBD patients has been limited. ILCs producing IL-17 or IFNγ (classified as ILC1) have also been described in mouse models of colitis (Buonocore et al., 2010; Klose et al., 2013) and human IBD (Bernink et al., 2013; Geremia et al., 2011), supporting a potentially important role for ILCs in IBD pathogenesis. Here, we observed a specific increase in IL-22 production by ILCs from colonic biopsies of patients with mild to moderate CD and UC. Despite characteristically distinct phenotypes, both CD and UC share genetic susceptibility risk alleles within the IL-23 pathway (Duerr et al., 2006), which may underlie a common role for ILCs during colonic inflammation in both diseases. In contrast to previous reports, we did not observe any significant IL-17 production by $CD3^-$ cells from patients with CD (Geremia et al., 2011) or a reduction in ILC3 in CD patients (Bernink et al., 2013). This difference may reflect clinical differences in the patient cohorts and samples—colonoscopic biopsies in our cohort were taken from ambulatory patients with mild to moderate colonic CD and UC, in contrast to surgical resection of ileal tissue from medically refractory patients in the other studies. As such, mild to moderate colitis may be the ideal human model to evaluate ILC3-producing IL-22 promoting mucosal healing. The association of clinical phenotype with ILC phenotype and the potential plasticity of these ILCs in colitis remain to be evaluated.

Consistent with our results in mouse models, $CX_3CR1^+$ MNPs from human intestinal tissue were more potent than $CD103^+$ DCs in supporting human intestinal ILC3 production of IL-22. In addition to the increased production of IL-23 and IL-1β by the $CX_3CR1^+$ subset described by us and others (Kamada et al., 2008), RNA seq analysis of these subsets revealed enrichment for transcripts from genes having IBD-associated SNPs, notably TL1A/TNFSF15. Polymorphisms in TNFSF15, the gene that encodes TL1A, are strongly associated with IBD, and expression of both TL1A and its receptors DR3 and DcDR3 is elevated in IBD patients (Kugathasan et al., 2008). TL1A has been shown to enhance Th17 differentiation and effector function (Kamada et al., 2010; Pappu et al., 2008); promote $T_{reg}$ expansion and ameliorate allergic asthma (Schreiber et al., 2010); and promote IL-13 production by ILC2s (Meylan et al., 2013). Interestingly, microbial stimulation and Fcγ-receptor engagement induces TL1A/TNFSF15 in monocytes and monocyte-derived mononuclear phagocytes (Shih et al., 2009). The data shown here reveal a potent ability of TL1A to enhance ILC3 production of IL-22 and suggest that the increased expression of TL1A by colonic $CX_3CR1^+$ MNPs enables their selective ability to potently support ILC3. Furthermore, the ability of TL1A to induce GM-CSF production by ILC3 is consistent with recent data suggesting that, even at steady state, CSF1R-expressing MNPs support ILC3 production of GM-CSF that, in turn, regulates oral tolerance (Mortha et al., 2014). Collectively, these data support a broader role for colonic $CX_3CR1^+$ MNPs in regulating mucosal homeostasis.

Mucosal ILC3 play a crucial role in barrier homeostasis, mucosal healing, and oral tolerance. $CX_3CR1^+$ MNPs are aptly poised to integrate microbial signals to regulate ILC3 and may serve as important targets for therapeutic manipulation. Further understanding of the contributions of discrete commensal bacterial species and of the mechanistic interactions between $CX_3CR1^+$ MNPs and ILC3 may provide novel strategies to promote intestinal healing. In light of the specific and potent regulation of ILC3 by colonic $CX_3CR1^+$ MNPs during colitis, diagnostics that correlate susceptible genotypes (Hueber et al., 2012) with clinical disease immunophenotype will provide insight into therapeutic strategies to manipulate colonic MNPs in the clinical management of IBD.

Example 2

To determine if there are human commensal bacteria that can induce cytokine production by ILC3, we transferred into germ-free mice, by oral gavage, fecal microbiota from patients with IBD (FIG. 8). After two weeks, we examined IL-22 expression in ILC3 in the lamina propria of the recipient mice. The results indicate that the complex microbiota from some patients (donor 2 in the figure) support IL-22 production by colonic ILC3. These data reveal the potential for using constituents of the human microbiota to induce ILC3 production of effector cytokines that can protect the epithelial barrier in patients with various inflammatory bowel diseases.

By way of summary and as demonstrated herein, ILC3 from the lamina propria of patients with IBD produce higher levels of IL-22 compared to ILC3 from patients without colitis. See also Longman et al. (2014, J Exp Med. 211: 1571). Using biopsy specimens from patients with a surgical diversion of the intestine, we further showed that ILC3 purified from mucosa not exposed to the fecal stream produced significantly less IL-22 upon ex vivo stimulation (Longman et al., supra). These data collectively support the ability of human microbiota to stimulate ILC3 production of IL-22.

Our proposal offers the unique opportunity to deliver TL1A or DR3 agonists to trigger ILC3 activation and promote mucosal healing. As we have shown, $CX_3CR1^+$ MNPs interact with ILC3 directly in the tissue (Longman et al. 2014, J Exp Med. 211:1571). This process is independent of CCR7 suggesting that migration to the secondary lymph organs is not required (Satpathy et al. 2013, Nature Immunol 14:937). Thus, luminal delivery of TL1A or DR3 agonists specifically targets innate immune cells in the tissue and not target naive T cells (Jones et al. 2011, The FASEB J 25:409), which are found in the secondary lymph organs.

While the disclosure is illustrated through specific examples, these examples are not intended to be restrictive and routine modifications to the various embodiment may be made by those skilled in the art.

REFERENCES

Adachi, O., T. Kawai, K. Takeda, M. Matsumoto, H. Tsutsui, M. Sakagami, K. Nakanishi, and S. Akira 1998. Targeted disruption of the MyD88 gene results in loss of IL-1- and IL-18-mediated function. *Immunity* 9:143-150.

Basu, R., D. B. O'Quinn, D. J. Silberger, T. R. Schoeb, L. Fouser, W. Ouyang, R. D. Hatton, and C. T. Weaver. 2012. Th22 cells are an important source of IL-22 for host protection against enteropathogenic bacteria. *Immunity* 37:1061-1075.

Bernink, J. H., C. P. Peters, M. Munneke, A. A. to Velde, S. L. Meijer, K. Weijer, H. S. Hreggvidsdottir, S. E. Heinsbroek, N. Legrand, C. J. Buskens, W. A. Bemelman, J. M. Mjosberg, and H. Spits. 2013. Human type 1 innate lymphoid cells accumulate in inflamed mucosal tissues. *Nat Immunol* 14:221-229.

Bogunovic, M., F. Ginhoux, J. Helft, L. Shang, D. Hashimoto, M. Greter, K. Liu, C. Jakubzick, M. A. Ingersoll, M. Leboeuf, E. R. Stanley, M. Nussenzweig, S. A. Lira, G. J. Randolph, and M. Merad. 2009. Origin of the lamina propria dendritic cell network. *Immunity* 31:513-525.

Buonocore, S., P. P. Ahern, H. H. Uhlig, Ivanov, II, D. R. Littman, K. J. Maloy, and F. Powrie. 2010. Innate lymphoid cells drive interleukin-23-dependent innate intestinal pathology. *Nature* 464:1371-1375.

Caton, M. L., M. R. Smith-Raska, and B. Reizis. 2007. Notch-RBP-J signaling controls the homeostasis of CD8− dendritic cells in the spleen. *J Exp Med* 204:1653-1664.

Cella, M., A. Fuchs, W. Vermi, F. Facchetti, K. Otero, J. K. Lennerz, J. M. Doherty, J. C. Mills, and M. Colonna. 2009. A human natural killer cell subset provides an innate source of IL-22 for mucosal immunity. *Nature* 457:722-725.

Cua, D. J., J. Sherlock, Y. Chen, C. A. Murphy, B. Joyce, B. Seymour, L. Lucian, W. To, S. Kwan, T. Churakova, S. Zurawski, M. Wiekowski, S. A. Lira, D. Gorman, R. A. Kastelein, and J. D. Sedgwick. 2003. Interleukin-23 rather than interleukin-12 is the critical cytokine for autoimmune inflammation of the brain. *Nature* 421:744-748.

Denning, T. L., B. A. Norris, O. Medina-Contreras, S. Manicassamy, D. Geem, R. Madan, C. L. Karp, and B. Pulendran. 2011. Functional specializations of intestinal dendritic cell and macrophage subsets that control Th17 and regulatory T cell responses are dependent on the T cell/APC ratio, source of mouse strain, and regional localization. *J Immunol* 187:733-747.

Diehl, G. E., R. S. Longman, J. X. Zhang, B. Breart, C. Galan, A. Cuesta, S. R. Schwab, and D. R. Littman. 2013. Microbiota restricts trafficking of bacteria to mesenteric lymph nodes by CX(3)CR1(hi) cells. *Nature* 494:116-120.

Duerr, R. H., K. D. Taylor, S. R. Brant, J. D. Rioux, M. S. Silverberg, M. J. Daly, A. H. Steinhart, C. Abraham, M. Regueiro, A. Griffiths, T. Dassopoulos, A. Bitton, H. Yang, S. Targan, L. W. Datta, E. O. Kistner, L. P. Schumm, A. T. Lee, P. K. Gregersen, M. M. Barmada, J. I. Rotter, D. L. Nicolae, and J. H. Cho. 2006. A genome-wide association study identifies IL23R as an inflammatory bowel disease gene. *Science* 314:1461-1463.

Eberl, G., S. Marmon, M. J. Sunshine, P. D. Rennert, Y. Choi, and D. R. Littman. 2004. An essential function for the nuclear receptor RORgamma(t) in the generation of fetal lymphoid tissue inducer cells. *Nat Immunol* 5:64-73.

Edelson, B. T., W. Kc, R. Juang, M. Kohyama, L. A. Benoit, P. A. Klekotka, C. Moon, J. C. Albring, W. Ise, D. G. Michael, D. Bhattacharya, T. S. Stappenbeck, M. J. Holtzman, S. S. Sung, T. L. Murphy, K. Hildner, and K. M. Murphy. 2010. Peripheral CD103+ dendritic cells form a unified subset developmentally related to CD8alpha+ conventional dendritic cells. *J Exp Med* 207:823-836.

Geremia, A., C. V. Arancibia-Carcamo, M. P. Fleming, N. Rust, B. Singh, N. J. Mortensen, S. P. Travis, and F. Powrie. 2011. IL-23-responsive innate lymphoid cells are increased in inflammatory bowel disease. *J Exp Med* 208:1127-1133.

Goto, Y., C. Panea, G. Nakato, A. Cebula, C. Lee, M. G. Diez, T. M. Laufer, L. Ignatowicz, and Ivanov, II. 2014. Segmented filamentous bacteria antigens presented by intestinal dendritic cells drive mucosal th17 cell differentiation. *Immunity* 40:594-607.

Hadis, U., B. Wahl, O. Schulz, M. Hardtke-Wolenski, A. Schippers, N. Wagner, W. Muller, T. Sparwasser, R. Forster, and O. Pabst. 2011. Intestinal tolerance requires gut homing and expansion of FoxP3+ regulatory T cells in the lamina propria. *Immunity* 34:237-246.

Hanash, A. M., J. A. Dudakov, G. Hua, M. H. O'Connor, L. F. Young, N. V. Singer, M. L. West, R. R. Jenq, A. M. Holland, L. W. Kappel, A. Ghosh, J. J. Tsai, U. K. Rao, N. L. Yim, O. M. Smith, E. Velardi, E. B. Hawryluk, G. F. Murphy, C. Liu, L. A. Fouser, R. Kolesnick, B. R. Blazar, and M. R. van den Brink. 2012. Interleukin-22 protects intestinal stem cells from immune-mediated tissue damage and regulates sensitivity to graft versus host disease. *Immunity* 37:339-350.

Harig, J. M., K. H. Soergel, R. A. Komorowski, and C. M. Wood. 1989. Treatment of diversion colitis with short-chain-fatty acid irrigation. *N Engl J Med* 320:23-28.

Hildner, K., B. T. Edelson, W. E. Purtha, M. Diamond, H. Matsushita, M. Kohyama, B. Calderon, B. U. Schraml, E. R. Unanue, M. S. Diamond, R. D. Schreiber, T. L. Murphy, and K. M. Murphy. 2008. Batf3 deficiency reveals a critical role for CD8alpha+ dendritic cells in cytotoxic T cell immunity. *Science* 322:1097-1100.

Huber, S., N. Gagliani, L. A. Zenewicz, F. J. Huber, L. Bosurgi, B. Hu, M. Hedl, W. Zhang, W. O'Connor, Jr., A. J. Murphy, D. M. Valenzuela, G. D. Yancopoulos, C. J. Booth, J. H. Cho, W. Ouyang, C. Abraham, and R. A. Flavell. 2012. IL-22BP is regulated by the inflammasome and modulates tumorigenesis in the intestine. *Nature* 491:259-263.

Hueber, W., B. E. Sands, S. Lewitzky, M. Vandemeulebroecke, W. Reinisch, P. D. Higgins, J. Wehkamp, B. G. Feagan, M. D. Yao, M. Karczewski, J. Karczewski, N. Pezous, S. Bek, G. Bruin, B. Mellgard, C. Berger, M. Londei, A. P. Bertolino, G. Tougas, and S. P. Travis. 2012. Secukinumab, a human anti-IL-17A monoclonal antibody, for moderate to severe Crohn's disease: unexpected results of a randomised, double-blind placebo-controlled trial. *Gut* 61:1693-1700.

Jung, S., J. Aliberti, P. Graemmel, M. J. Sunshine, G. W. Kreutzberg, A. Sher, and D. R. Littman. 2000. Analysis of fractalkine receptor CX(3)CR1 function by targeted deletion and green fluorescent protein reporter gene insertion. *Mol Cell Biol* 20:4106-4114.

Kamada, N., T. Hisamatsu, H. Honda, T. Kobayashi, H. Chinen, T. Takayama, M. T. Kitazume, S. Okamoto, K. Koganei, A. Sugita, T. Kanai, and T. Hibi. 2010. TL1A produced by lamina propria macrophages induces Th1 and Th17 immune responses in cooperation with IL-23 in patients with Crohn's disease. *Inflamm Bowel Dis* 16:568-575.

Kamada, N., T. Hisamatsu, S. Okamoto, H. Chinen, T. Kobayashi, T. Sato, A. Sakuraba, M. T. Kitazume, A. Sugita, K. Koganei, K. S. Akagawa, and T. Hibi. 2008. Unique CD14 intestinal macrophages contribute to the pathogenesis of Crohn disease via IL-23/IFN-gamma axis. *J Clin Invest* 118:2269-2280.

Kinnebrew, M. A., C. G. Buffie, G. E. Diehl, L. A. Zenewicz, I. Leiner, T. M. Hohl, R. A. Flavell, D. R. Littman, and E. G. Pamer. 2012. Interleukin 23 production by intestinal CD103(+)CD11b(+) dendritic cells in response to bacterial flagellin enhances mucosal innate immune defense. *Immunity* 36:276-287.

Kirchberger, S., D. J. Royston, O. Boulard, E. Thornton, F. Franchini, R. L. Szabady, O. Harrison, and F. Powrie. 2013. Innate lymphoid cells sustain colon cancer through production of interleukin-22 in a mouse model. *J Exp Med* 210:917-931.

Klose, C. S., E. A. Kiss, V. Schwierzeck, K. Ebert, T. Hoyler, Y. d'Hargues, N. Goppert, A. L. Croxford, A. Waisman, Y. Tanriver, and A. Diefenbach. 2013. A T-bet gradient controls the fate and function of CCR6-RORgammat+ innate lymphoid cells. *Nature* 494:261-265.

Kugathasan, S., R. N. Baldassano, J. P. Bradfield, P. M. Sleiman, M. Imielinski, S. L. Guthery, S. Cucchiara, C. E. Kim, E. C. Frackelton, K. Annaiah, J. T. Glessner, E. Santa, T. Willson, A. W. Eckert, E. Bonkowski, J. L. Shaner, R. M. Smith, F. G. Otieno, N. Peterson, D. J. Abrams, R. M. Chiavacci, R. Grundmeier, P. Mamula, G. Tomer, D. A. Piccoli, D. S. Monos, V. Annese, L. A. Denson, S. F. Grant, and H. Hakonarson. 2008. Loci on 20q13 and 21q22 are associated with pediatric-onset inflammatory bowel disease. *Nat Genet* 40:1211-1215.

Lewis, K. L., M. L. Caton, M. Bogunovic, M. Greter, L. T. Grajkowska, D. Ng, A. Klinakis, I. F. Charo, S. Jung, J. L. Gommerman, Ivanov, II, K. Liu, M. Merad, and B. Reizis. 2011. Notch2 receptor signaling controls functional differentiation of dendritic cells in the spleen and intestine. *Immunity* 35:780-791.

Manta, C., E. Heupel, K. Radulovic, V. Rossini, N. Garbi, C. U. Riedel, and J. H. Niess. 2013. CX(3)CR1(+) macrophages support IL-22 production by innate lymphoid cells during infection with *Citrobacter rodentium*. *Mucosal Immunol* 6:177-188.

Merad, M., P. Sathe, J. Helft, J. Miller, and A. Mortha. 2013. The dendritic cell lineage: ontogeny and function of dendritic cells and their subsets in the steady state and the inflamed setting. *Annu Rev Immunol* 31:563-604.

Meylan, F., E. T. Hawley, L. Barron, J. L. Barlow, P. Penmetcha, M. Pelletier, G. Sciume, A. C. Richard, E. T. Hayes, J. Gomez-Rodriguez, X. Chen, W. E. Paul, T. A.

Wynn, A. N. McKenzie, and R. M. Siegel. 2013. The TNF-family cytokine TL1A promotes allergic immunopathology through group 2 innate lymphoid cells. *Mucosal Immunol*

Mortha, A., A. Chudnovskiy, D. Hashimoto, M. Bogunovic, S. P. Spencer, Y. Belkaid, and M. Merad. 2014. Microbiota-Dependent Crosstalk Between Macrophages and ILC3 Promotes Intestinal Homeostasis. *Science*

Niess, J. H., S. Brand, X. Gu, L. Landsman, S. Jung, B. A. McCormick, J. M. Vyas, M. Boes, H. L. Ploegh, J. G. Fox, D. R. Littman, and H. C. Reinecker. 2005. CX3CR1-mediated dendritic cell access to the intestinal lumen and bacterial clearance. *Science* 307:254-258.

Pappu, B. P., A. Borodovsky, T. S. Zheng, X. Yang, P. Wu, X. Dong, S. Weng, B. Browning, M. L. Scott, L. Ma, L. Su, Q. Tian, P. Schneider, R. A. Flavell, C. Dong, and L. C. Burkly. 2008. TL1A-DR3 interaction regulates Th17 cell function and Th17-mediated autoimmune disease. *J Exp Med* 205:1049-1062.

Persson, E. K., H. Uronen-Hansson, M. Semmrich, A. Rivollier, K. Hagerbrand, J. Marsal, S. Gudjonsson, U. Hakansson, B. Reizis, K. Kotarsky, and W. W. Agace. 2013. IRF4 transcription-factor-dependent CD103(+) CD11b(+) dendritic cells drive mucosal T helper 17 cell differentiation. *Immunity* 38:958-969.

Pickert, G., C. Neufert, M. Leppkes, Y. Zheng, N. Wittkopf, M. Warntjen, H. A. Lehr, S. Hirth, B. Weigmann, S. Wirtz, W. Ouyang, M. F. Neurath, and C. Becker. 2009. STAT3 links IL-22 signaling in intestinal epithelial cells to mucosal wound healing. *J Exp Med* 206:1465-1472. Pineton de Chambrun, G., L. Peyrin-Biroulet, M. Lemann, and J. F. Colombel. 2010. Clinical implications of mucosal healing for the management of IBD. *Nat Rev Gastroenterol Hepatol* 7:15-29.

Qiu, J., J. J. Heller, X. Guo, Z. M. Chen, K. Fish, Y. X. Fu, and L. Zhou. 2012. The aryl hydrocarbon receptor regulates gut immunity through modulation of innate lymphoid cells. *Immunity* 36:92-104.

Satoh-Takayama, N., C. A. Vosshenrich, S. Lesjean-Pottier, S. Sawa, M. Lochner, F. Rattis, J. J. Mention, K. Thiam, N. Cerf-Bensussan, O. Mandelboim, G. Eberl, and J. P. Di Santo. 2008. Microbial flora drives interleukin 22 production in intestinal NKp46+ cells that provide innate mucosal immune defense. *Immunity* 29:958-970.

Satpathy, A. T., C. G. Briseno, J. S. Lee, D. Ng, N. A. Manieri, W. Kc, X. Wu, S. R. Thomas, W. L. Lee, M. Turkoz, K. G. McDonald, M. M. Meredith, C. Song, C. J. Guidos, R. D. Newberry, W. Ouyang, T. L. Murphy, T. S. Stappenbeck, J. L. Gommerman, M. C. Nussenzweig, M. Colonna, R. Kopan, and K. M. Murphy. 2013. Notch2-dependent classical dendritic cells orchestrate intestinal immunity to attaching-and-effacing bacterial pathogens. *Nat Immunol* 14:937-948.

Sawa, S., M. Lochner, N. Satoh-Takayama, S. Dulauroy, M. Berard, M. Kleinschek, D. Cua, J. P. Di Santo, and G. Eberl. 2011. RORgammat+ innate lymphoid cells regulate intestinal homeostasis by integrating negative signals from the symbiotic microbiota. *Nat Immunol* 12:320-326.

Schlitzer, A., N. McGovern, P. Teo, T. Zelante, K. Atarashi, D. Low, A. W. Ho, P. See, A. Shin, P. S. Wasan, G. Hoeffel, B. Malleret, A. Heiseke, S. Chew, L. Jardine, H. A. Purvis, C. M. Hilkens, J. Tam, M. Poidinger, E. R. Stanley, A. B. Krug, L. Renia, B. Sivasankar, L. G. Ng, M. Collin, P. Ricciardi-Castagnoli, K. Honda, M. Haniffa, and F. Ginhoux. 2013. IRF4 transcription factor-dependent CD11b+ dendritic cells in human and mouse control mucosal IL-17 cytokine responses. *Immunity* 38:970-983.

Schreiber, H. A., J. Loschko, R. A. Karssemeijer, A. Escolano, M. M. Meredith, D. Mucida, P. Guermonprez, and M. C. Nussenzweig. 2013. Intestinal monocytes and macrophages are required for T cell polarization in response to *Citrobacter rodentium*. *J Exp Med* 210:2025-2039.

Schreiber, T. H., D. Wolf, M. S. Tsai, J. Chirinos, V. V. Deyev, L. Gonzalez, T. R. Malek, R. B. Levy, and E. R. Podack. 2010. Therapeutic Treg expansion in mice by TNFRSF25 prevents allergic lung inflammation. *J Clin Invest* 120:3629-3640.

Shih, D. Q., L. Y. Kwan, V. Chavez, O. Cohavy, R. Gonsky, E. Y. Chang, C. Chang, C. O. Elson, and S. R. Targan. 2009. Microbial induction of inflammatory bowel disease associated gene TL1A (TNFSF15) in antigen presenting cells. *Eur J Immunol* 39:3239-3250.

Sonnenberg, G. F., and D. Artis. 2012. Innate lymphoid cell interactions with microbiota: implications for intestinal health and disease. *Immunity* 37:601-610.

Sonnenberg, G. F., L. A. Monticelli, M. M. Elloso, L. A. Fouser, and D. Artis. 2011. CD4(+) lymphoid tissue-inducer cells promote innate immunity in the gut. *Immunity* 34:122-134.

Spits, H., D. Artis, M. Colonna, A. Diefenbach, J. P. Di Santo, G. Eberl, S. Koyasu, R. M. Locksley, A. N. McKenzie, R. E. Mebius, F. Powrie, and E. Vivier. 2013. Innate lymphoid cells—a proposal for uniform nomenclature. *Nat Rev Immunol* 13:145-149.

Sun, C. M., J. A. Hall, R. B. Blank, N. Bouladoux, M. Oukka, J. R. Mora, and Y. Belkaid. 2007. Small intestine lamina propria dendritic cells promote de novo generation of Foxp3 T reg cells via retinoic acid. *J Exp Med* 204:1775-1785.

Tamoutounour, S., S. Henri, H. Lelouard, B. de Bovis, C. de Haar, C. J. van der Woude, A. M. Woltman, Y. Reyal, D. Bonnet, D. Sichien, C. C. Bain, A. M. Mowat, C. Reis e Sousa, L. F. Poulin, B. Malissen, and M. Guilliams. 2012. CD64 distinguishes macrophages from dendritic cells in the gut and reveals the Th1-inducing role of mesenteric lymph node macrophages during colitis. *Eur J Immunol* 42:3150-3166.

Varol, C., E. Zigmond, and S. Jung. 2010. Securing the immune tightrope: mononuclear phagocytes in the intestinal lamina propria. *Nat Rev Immunol* 10:415-426.

Vernia, P., M. Cittadini, R. Caprilli, and A. Torsoli. 1995. Topical treatment of refractory distal ulcerative colitis with 5-ASA and sodium butyrate. *Dig Dis Sci* 40:305-307.

Welty, N. E., C. Staley, N. Ghilardi, M. J. Sadowsky, B. Z. Igyarto, and D. H. Kaplan. 2013. Intestinal lamina propria dendritic cells maintain T cell homeostasis but do not affect commensalism. *J Exp Med* 210:2011-2024.

Wynn, T. A., A. Chawla, and J. W. Pollard. 2013. Macrophage biology in development, homeostasis and disease. *Nature* 496:445-455.

Zheng, Y., P. A. Valdez, D. M. Danilenko, Y. Hu, S. M. Sa, Q. Gong, A. R. Abbas, Z. Modrusan, N. Ghilardi, F. J. de Sauvage, and W. Ouyang. 2008. Interleukin-22 mediates early host defense against attaching and effacing bacterial pathogens. *Nat Med* 14:282-289.

Zigmond, E., C. Varol, J. Farache, E. Elmaliah, A. T. Satpathy, G. Friedlander, M. Mack, N. Shpigel, I. G. Boneca, K. M. Murphy, G. Shakhar, Z. Halpern, and S. Jung. 2012. Ly6C hi monocytes in the inflamed colon give rise to proinflammatory effector cells and migratory antigen-presenting cells. *Immunity* 37:1076-1090.

What is claimed is:

1. A method for treating an inflammatory bowel disease (IBD) in a subject, the method comprising administering to the subject a therapeutically effective amount of tumor necrosis factor like ligand 1A (TL1A) or an agent that activates death-domain receptor 3 (DR3), wherein the agent that activates DR3 is an agonistic DR3 antibody, in a composition formulated for oral delivery and to release the TL1A or the agent that activates DR3 in the subject's large intestine, wherein the release of the TL1A or the agent that activates the DR3 in the subject's large intestine promotes mucosal healing in the subject's large intestine, thereby treating IBD in the subject.

2. The method of claim 1, wherein the IBD is Crohn's Disease (CD) or ulcerative colitis (UC).

3. The method of claim 1, wherein the composition is formulated to release the TL1A or the agent that activates DR3 at a pH characteristic of the large intestine.

4. The method of claim 3, wherein the pH is about pH 7.0.

5. The method of claim 1, wherein the subject is a human.

6. The method of claim 1, wherein the TL1A is recombinant TL1A.

7. A method for treating an inflammatory bowel disease (IBD) in a subject, the method comprising administering to the subject via rectal delivery a therapeutically effective amount of tumor necrosis factor like ligand 1A (TL1A) or an agent that activates death-domain receptor 3 (DR3), wherein the agent that activates DR3 is an agonistic DR3 antibody, or a composition thereof, wherein the TL1A or the agent that activates the DR3 or the composition thereof is administered rectally to promote mucosal healing in the subject's small or large intestine, thereby treating IBD in the subject.

8. The method of claim 7, wherein the IBD is Crohn's Disease (CD) or ulcerative colitis (UC).

9. The method of claim 7, wherein the composition is formulated for rectal delivery.

10. The method of claim 9, wherein the composition formulated for rectal delivery is formulated to release the TL1A or the agent that activates DR3 in the subject's small or large intestine.

11. The method of claim 10, wherein the composition is formulated to release the TL1A or the agent that activates DR3 at a pH characteristic of the small intestine.

12. The method of claim 11, wherein the pH is about pH 6.0.

13. The method of claim 10, wherein the composition is formulated to release the TL1A or the agent that activates DR3 at a pH characteristic of the large intestine.

14. The method of claim 13, wherein the pH is about pH 7.0.

15. The method of claim 7, wherein the subject is a human.

16. The method of claim 7, wherein the TL1A is recombinant TL1A.

17. A method for activating interleukin (IL)-22-producing group 3 innate lymphoid cells (ILC3s) in a subject afflicted with an inflammatory bowel disease (IBD), the method comprising administering to the subject via rectal delivery a therapeutically effective amount of tumor necrosis factor like ligand 1A (TL1A) or an agent that activates death-domain receptor 3 (DR3), wherein the agent that activates DR3 is an agonistic DR3 antibody, or a composition thereof, wherein the TL1A or the agent that activates the DR3 or the composition thereof is administered rectally to activate ILC3s proximal to the intestinal epithelial layer of the subject's large intestine to produce IL-22, thereby promoting mucosal healing in the subject's large intestine.

* * * * *

SEQUENCE LISTING

<160> NUMBER OF SEQ ID NOS: 11

<210> SEQ ID NO 1
<211> LENGTH: 6705
<212> TYPE: DNA
<213> ORGANISM: Homo sapiens

<400> SEQUENCE: 1

| | | | | | | |
|---|---|---|---|---|---|---|
| ggaaaaggga | aggaggagac | tgagtgatta | agtcacccac | tgtgagagct | ggtcttctat | 60 |
| ttaatggggg | ctctctctgc | ccaggagtca | gaggtgcctc | caggagcagc | aggagcatgg | 120 |
| ccgaggatct | gggactgagc | tttggggaaa | cagccagtgt | ggaaatgctg | ccagagcacg | 180 |
| gcagctgcag | gcccaaggcc | aggagcagca | gcgcacgctg | gctctcacc | tgctgcctgg | 240 |
| tgttgctccc | cttccttgca | ggactcacca | catacctgct | tgtcagccag | ctccgggccc | 300 |
| agggagaggc | ctgtgtgcag | ttccaggctc | taaaaggaca | ggagtttgca | ccttcacatc | 360 |
| agcaagttta | tgcacctctt | agagcagacg | gagataagcc | aagggcacac | ctgacagttg | 420 |
| tgagacaaac | tcccacacag | cactttaaaa | atcagttccc | agctctgcac | tgggaacatg | 480 |
| aactaggcct | ggccttcacc | aagaaccgaa | tgaactatac | caacaaattc | ctgctgatcc | 540 |
| cagagtcggg | agactacttc | atttactccc | aggtcacatt | ccgtgggatg | acctctgagt | 600 |
| gcagtgaaat | cagacaagca | ggccgaccaa | acaagccaga | ctccatcact | gtggtcatca | 660 |
| ccaaggtaac | agacagctac | cctgagccaa | cccagctcct | catggggacc | aagtctgtat | 720 |
| gcgaagtagg | tagcaactgg | ttccagccca | tctacctcgg | agccatgttc | tccttgcaag | 780 |
| aaggggacaa | gctaatggtg | aacgtcagtg | acatctcttt | ggtggattac | acaaaagaag | 840 |
| ataaaacctt | ctttggagcc | ttcttactat | aggaggagag | caaatatcat | tatatgaaag | 900 |
| tcctctgcca | ccgagttcct | aatttctctt | gttcaaatgt | aattataacc | aggggttttc | 960 |
| ttggggccgg | gagtagggg | cattccacag | ggacaacggt | ttagctatga | aatttggggc | 1020 |
| ccaaaatttc | acacttcatg | tgccttactg | atgagagtac | taactggaaa | aaggctgaag | 1080 |
| agagcaaata | tattattaag | atgggttgga | ggattggcga | gtttctaaat | attaagacac | 1140 |
| tgatcactaa | atgaatggat | gatctactcg | ggtcaggatt | gaaagagaaa | tatttcaaca | 1200 |
| ccttcctgct | atacaatggt | caccagtggt | ccagttattg | ttcaatttga | tcataaattt | 1260 |
| gcttcaattc | aggagctttg | aaggaagtcc | aaggaaagct | ctagaaaaca | gtataaactt | 1320 |
| tcagaggcaa | aatccttcac | caattttttcc | acatactttc | atgccttgcc | taaaaaaaat | 1380 |
| gaaaagagag | ttggtatgtc | tcatgaatgt | tcacacagaa | ggagttggtt | ttcatgtcat | 1440 |
| ctacagcata | tgagaaaagc | tacctttctt | ttgattatgt | acacagatat | ctaaataagg | 1500 |
| aagtatgagt | ttcacatgta | tatcaaaaat | acaacagttg | cttgtattca | gtagagtttt | 1560 |
| cttgcccacc | tattttgtgc | tgggttctac | cttaacccag | aagacactat | gaaaaacaag | 1620 |
| acagactcca | ctcaaaattt | atatgaacac | cactagatac | ttcctgatca | aacatcagtc | 1680 |
| aacatactct | aaagaataac | tccaagtctt | ggccaggcgc | agtggctcac | acctgtaatc | 1740 |
| ccaacacttt | gggaggccaa | ggtgggtgga | tcatctaagg | ccgggagttc | aagaccagcc | 1800 |
| tgaccaacgt | ggagaaaccc | catctctact | aaaaatacaa | aattagccgg | gcgtggtagc | 1860 |
| gcatggctgt | aatcctggct | actcaggagg | ccgaggcaga | agaattgctt | gaactgggga | 1920 |
| ggcagaggtt | gcggtgagcc | cagatcgcgc | cattgcactc | cagcctgggt | aacaagagca | 1980 |
| aaactctgtc | caaaaaaaaa | aaaataaaat | aataactcca | agcctttaaa | aaatatcatc | 2040 |
| tgaaactgtt | acatcagatt | tctggcactc | tactgactgt | ggaagatagc | cagctgactg | 2100 |

```
gaagatagcc agctgattag ttccctgaag aaacctgaag acagatacct ggttaactag    2160
atcaactaca ctgccaactt gtttgatgct gagagacaat ggacttattc catgggggaa    2220
gggaaaaaag aagtcaatca ccaaatctga agaagttaac ctagatcttt gaggtttgat    2280
ttgcaacttt atatgcagag tattatgtgg gtattttccc ttaaaatatt caaagggatt    2340
tacatatggg attagctaat gagcctagcc aagaccttcc ctggaggaca ggctggtcat    2400
tgcggaggtc ccttctgtgc ttcagtgggt tcatatcctc tagtccgtat gattttccta    2460
cgctaatatg tcaagggcag gagaggcagc tctgttctcc tagcctttgt tgacttgtct    2520
gcaaagcagg aatctgccca tttgtttcca aggagcaaat gagctcatga gaatgaaaga    2580
tgttaacttc atgcattctg tgccatctga gcatttcggt attatatgac tggtgaccct    2640
tggcccgtat tataaatgct tcctatcctg gagacctca tggatgagtc tgagaggaaa     2700
tttggcacca aaatcactct cactctggtt tccagtagac tatagaggca gagaggcatt    2760
tgagaggctc ctgagcaaag tgtccagtgt agcaggagca cttcattaat atttattgag    2820
ttataattaa ataaaaatta atttctgatt tctcagtttg gaggttaagg ctctaaatat    2880
attttctaac ctctgctagg ctaacttaag ccaggccttt tcttgccttt ccctttctca    2940
aaacagtcag cacagactca gtgggagcac agaggagtgt ggtcacctcc acctggctca    3000
ccagagtctt catagaggaa gtgaagcctg gaagaaactg ggcgggcccc agatgaccac    3060
agggaaaggg catctcagat ggaggaatta cccttgactt aaagcagaaa agaaagattt    3120
ctcagtaact ccaaaacttg cttgatagga gaatattccc tcaaccaatt cctaggacaa    3180
tatttattgg tagatcaaga atgtttcctc aataactcta gtctagctcc atgatcagaa    3240
ctaacaccca ttaaaaacat aaaatgttct ttctgaaccg gtcttcatgg tgcgtgagag    3300
caccaagcag ctttggtatg caggaggagt tttgcacaga agagtggcct gctcaaacct    3360
gcccactgtt ctgtaggtga tctggtggat ctggaaattt atcccaagac aggaatttcc    3420
taatattcga agacatttga ggctttggga aattctctgc tgtgcattta tttggctcct    3480
gtcataagct tgttttttaa agaatgtatc atagctcaag ttttactgc tgattttgtt      3540 aaattctgta tagtatattt tttacggaaa ggcacagtca gacattccta ataggctca      3600 tgtcagaact tctgttccca aggcattatc tccatagcaa aaattagtgc actgttttca    3660
aaagtgaggt gggaaaatgc ttttaagatc atgtgatgtt ccctaaaag gggttaatgg      3720 ggtgtattca gggtttggga gggaggaaga agcatgcttt agaaaacagt aaatttaggg    3780
agaaaatgct ttgttggtta aatgtcactc aaaaggctga attcaaatca attccacaaa    3840
catttactga gtacctactg cccctgggga cacagagata aattatttag tctcagacac    3900
actcattcta acttcccagc acctctactg tctgcagatt cttttaattta ttttggttgt    3960 attagctaat taattcgtaa actttaggca catggatcta ttctcattat gaaaatggat    4020
gccatttgat taaggctgat gactaacaaa atgatttgtg tttactcgaa gtgtttttt     4080 aaaaatagct actcaaggat agttttccat aaatcaagaa ggtaaaaaag ttcccatttt    4140
ttattgtaga atccattatt taaactacat gtagagacag gttattattt gctatattca    4200
agtttggtca tcaatacoot taaaaatatt agaattttat ggatgaccca gaaatgcttt    4260
gaaaatctgt gttcctcagc aaatacagag accatgatca aaatgcacag aatcactaac    4320
attttgatgc tagcatggtt tcagtctatt tggcagaaca gaattgatta tgctactaaa    4380 atttctttt cttttttttt tttttttttt ttgagacaga gtcttgcttt gtcacccagg      4440
```

-continued

```
ctgaagtgca gtggcaggat ctcagttcac tgcaacctct gcctcccagg ttcacgccat    4500
tctcctgctt cagcctcccg agtagctggg actacaggct cccaccacca tgcccggcta    4560 atttttttgca ttttttagtag agacggggtt tcaccgtgtt agccaggatg gtctcgatct    4620
cctgacctcg tgatccgccc gcctcagcct tccaaagtgc tgggattaca ggcgtgagcc    4680
actgtgcccg gactctgatt ttttttttac taaggtacag taagaaaagg gaaaagtgta    4740
cgttttcact tcctgaaata tgtcaggttg aatcaataat agagcacacc agaactcttg    4800
gctccatttc aacctaaact attcagttct catcacccca gaggaaattc cgcctctgtg    4860
ctggtcagta atccccctgg attataaaag tttaactaac tcactgtgca caaggcacgg    4920
ccattgccaa cattctcttg caaggtattt tcccaagccc ttacccaatt ctgtttccat    4980
gattgtgaca ttggggatta attctgcaag acagaactgt ttatattctg taccttaaaa    5040
acacatgcaa acatctcttg ccttaagatt tctggctttc ctatggccca gagtcctaga    5100
agtgttttga tatttgtagc agaattttca agtgtacatc cttatcctgg atattaacat    5160
ttttgcatca tattggcagc tggacctaca gagaatttag tagactgtta acctaataag    5220
ccttgaatcc ttttgcacca gtggtgagag aatgtggatc agagccatca cctccatgcc    5280
ccgtcaccct ctaacaacca catttacaac ttccccagct ctgagacaca cttgcctcca    5340 cccccttccat cacccccattt taagatgaaa ataccacacc agcctggaag gaagaagtta    5400
cttgcccagg gccacatagt gagttaaggg ctgatctaga gctaggaagc tgtcttcctg    5460
aaccataatc ctggactctt ctaacctctc tactcatcgc aaatagagtt catttagtg    5520 attttgaagga agatgggaca agtattttca aacacctgta ggacaacatg gaagtgggag    5580
gagacttcta ctgtagctcc ccagagaaga gagctagggc tacagagttg cagttacaag    5640
gttgccctct ctggcttgat ccccaaagga atttttctact ccaaaataga attttttctag    5700 gatgctattt ctcagtccct ggagatactc aaacaaaggg cttgtcacaa gggttttttgt    5760 agaagctatt cttcacagag gttgggggag agattaagcc aaaggatctc tgaggtctttt    5820 ttcaaatcta taattatgtg gccttttgtt cattgacttc catgtgttct agttgatcat    5880
tacaaacctg gcaggccttc tcaagggttc agtaattagc tgtcatttcc catttgtcca    5940
gagagtgtcc aacacaaaat acccctaaga tcttggccaa tagagaaatg tcatggaatt    6000
ttagaaatga cagtatctgc ggagtttatt ccaagttata tcatttcaaa gatgaagaaa    6060
cccaggctca gagggagcca tcacatccac accctgtcac ccttcgtggc cagtgccaga    6120
cagtagctag ttggatgcta aaagtagaat ttagatatct taacaataag cccagcagtc    6180
tttcaacttc attcgtaaat catttttgtt ttgagcatct gtcacgtggc agcacttgcc    6240
tggatactgg agagctgaga aggaatgcga caggcaagtc ctactctcac agtgtataca    6300
ttcaggagga acaagacaca cagtgccaag taaataaagt agctgaactt catcaaatga    6360
ttttattctt aaagtcatta aagcatgtaa tgttcccctt tttttgtttc aggggtgtac    6420
agattgaaga agtgtaggtg tttatgtggt tttagtgaca acccccatgt gctttcattg    6480
attttatgtt ttatgttaaa acatcaaccg caaggtaaaa tgcatattgt atgttgttgg    6540
atacgtactt aactgtgtatg catcccatgt ctttgggtac tagtgtatga attctaatct    6600
ctgtaaatga aatgttgtat gtgttaatat atttaataga tgtaacttaa taaactggca    6660
ttgaagactg aagaatttttc acactgtcaa aaaaaaaaaa aaaaa    6705
```

<210> SEQ ID NO 2
<211> LENGTH: 6412

<212> TYPE: DNA
<213> ORGANISM: Homo sapiens

<400> SEQUENCE: 2

| | | | | | |
|---|---|---|---|---|---|
| atgcaactca | caaagggccg | tcttcatttc | agtcacccett | tgtctcatac | aaagcacatt | 60 |
| tctccttttg | ttacagatgc | acctcttaga | gcagacggag | ataagccaag | ggcacacctg | 120 |
| acagttgtga | gacaaactcc | cacacagcac | tttaaaaatc | agttcccagc | tctgcactgg | 180 |
| gaacatgaac | taggcctggc | cttcaccaag | aaccgaatga | actataccaa | caaattcctg | 240 |
| ctgatcccag | agtcgggaga | ctacttcatt | tactcccagg | tcacattccg | tgggatgacc | 300 |
| tctgagtgca | gtgaaatcag | acaagcaggc | cgaccaaaca | agccagactc | catcactgtg | 360 |
| gtcatcacca | aggtaacaga | cagctaccct | gagccaaccc | agctcctcat | ggggaccaag | 420 |
| tctgtatgcg | aagtaggtag | caactggttc | cagcccatct | acctcggagc | catgttctcc | 480 |
| ttgcaagaag | gggacaagct | aatggtgaac | gtcagtgaca | tctctttggt | ggattacaca | 540 |
| aaagaagata | aaaccttctt | tggagccttc | ttactatagg | aggagagcaa | atatcattat | 600 |
| atgaaagtcc | tctgccaccg | agttcctaat | tttctttgtt | caaatgtaat | tataaccagg | 660 |
| ggttttcttg | gggccgggag | taggggcat | tccacaggga | caacggttta | gctatgaaat | 720 |
| ttggggccca | aaatttcaca | cttcatgtgc | cttactgatg | agagtactaa | ctggaaaaag | 780 |
| gctgaagaga | gcaaatatat | tattaagatg | ggttggagga | ttggcgagtt | tctaaatatt | 840 |
| aagacactga | tcactaaatg | aatggatgat | ctactcgggt | caggattgaa | agagaaatat | 900 |
| ttcaacaccct | tcctgctata | caatggtcac | cagtggtcca | gttattgttc | aatttgatca | 960 |
| taaatttgct | tcaattcagg | agctttgaag | gaagtccaag | gaaagctcta | gaaaacagta | 1020 |
| taaactttca | gaggcaaaat | ccttcaccaa | tttttccaca | tactttcatg | ccttgcctaa | 1080 |
| aaaaaatgaa | aagagagttg | gtatgtctca | tgaatgttca | cacagaagga | gttggttttc | 1140 |
| atgtcatcta | cagcatatga | gaaaagctac | ctttcttttg | attatgtaca | cagatatcta | 1200 |
| aataaggaag | tatgagtttc | acatgtatat | caaaaataca | acagttgctt | gtattcagta | 1260 |
| gagttttctt | gcccacctat | tttgtgctgg | gttctacctt | aacccagaag | acactatgaa | 1320 |
| aaacaagaca | gactccactc | aaaatttata | tgaacaccac | tagatacttc | ctgatcaaac | 1380 |
| atcagtcaac | atactctaaa | gaataactcc | aagtcttggc | caggcgcagt | ggctcacacc | 1440 |
| tgtaatccca | acactttggg | aggccaaggt | gggtggatca | tctaaggccg | ggagttcaag | 1500 |
| accagcctga | ccaacgtgga | gaaaccccat | ctctactaaa | aatacaaaat | tagccgggcg | 1560 |
| tggtagcgca | tggctgtaat | cctggctact | caggaggccg | aggcagaaga | attgcttgaa | 1620 |
| ctggggaggc | agaggttgcg | gtgagcccag | atcgcgccat | tgcactccag | cctgggtaac | 1680 |
| aagagcaaaa | ctctgtccaa | aaaaaaaaaa | ataaataat | aactccaagc | ctttaaaaaa | 1740 |
| tatcatctga | aactgttaca | tcagatttct | ggcactctac | tgactgtgga | agatagccag | 1800 |
| ctgactggaa | gatagccagc | tgattagttc | cctgaagaaa | cctgaagaca | gatacctggt | 1860 |
| taactagatc | aactacactg | ccaacttgtt | tgatgctgag | agacaatgga | cttattccat | 1920 |
| gggggaaggg | aaaaagaag | tcaatcacca | aatctgaaga | agttaaccta | gatctttgag | 1980 |
| gtttgatttg | caacttttata | tgcagagtat | tatgtgggta | ttttcccctta | aaatattcaa | 2040 |
| agggatttac | atatgggatt | agctaatgag | cctagccaag | accttccctg | gaggacaggc | 2100 |
| tggtcattgc | ggaggtccct | tctgtgcttc | agtgggttca | tatcctctag | tccgtatgat | 2160 |
| tttcctacgc | taatatgtca | agggcaggag | aggcagctct | gttctcctag | cctttgttga | 2220 |

```
cttgtctgca aagcaggaat ctgcccattt gtttccaagg agcaaatgag ctcatgagaa    2280
tgaaagatgt taacttcatg cattctgtgc catctgagca tttcggtatt atatgactgg    2340
tgacccttgg cccgtattat aaatgcttcc tatcctggga gacctcatgg atgagtctga    2400
gaggaaattt ggcaccaaaa tcactctcac tctggtttcc agtagactat agaggcagag    2460
aggcatttga gaggctcctg agcaaagtgt ccagtgtagc aggagcactt cattaatatt    2520
tattgagtta taattaaata aaaattaatt tctgatttct cagtttggag gttaaggctc    2580
taaatatatt ttctaacctc tgctaggcta acttaagcca ggcctttttc ttgccttccc    2640
tttctcaaaa cagtcagcac agactcagtg ggagcacaga ggagtgtggt cacctccacc    2700
tggctcacca gagtcttcat agaggaagtg aagcctggaa gaaactgggc gggccccaga    2760
tgaccacagg gaagggcat ctcagatgga ggaattaccc ttgacttaaa gcagaaaaga    2820
aagatttctc agtaactcca aaacttgctt gataggagaa tattccctca accaattcct    2880
aggacaatat ttattggtag atcaagaatg tttcctcaat aactctagtc tagctccatg    2940
atcagaacta acacccatta aaaacataaa atgttctttc tgaaccggtc ttcatggtgc    3000
gtgagagcac caagcagctt tggtatgcag gaggagtttt gcacagaaga gtggcctgct    3060
caaacctgcc cactgttctg taggtgatct ggtggatctg gaaatttatc ccaagacagg    3120
aatttcctaa tattcgaaga catttgaggc tttgggaaat tctctgctgt gcatttattt    3180
ggctcctgtc ataagcttgt ttttaaaga atgtatcata gctcaagttt ttactgctga    3240
ttttgttaaa ttctgtatag tatatttttt acggaaaggc acagtcagac attcctaata    3300
gggctcatgt cagaacttct gttcccaagg cattatctcc atagcaaaaa ttagtgcact    3360
gttttcaaaa gtgaggtggg aaaatgcttt taagatcatg tgatgttccc ctaaaagggg    3420
ttaatggggt gtattcaggg tttgggaggg aggaagaagc atgctttaga aaacagtaaa    3480
tttagggaga aaatgctttg ttggttaaat gtcactcaaa aggctgaatt caaatcaatt    3540
ccacaaacat ttactgagta cctactgccc ctggggacac agagataaat tatttagtct    3600
cagacacact cattctaact tcccagcacc tctactgtct gcagattctt taatttattt    3660
tggttgtatt agctaattaa ttcgtaaact ttaggcacat ggatctattc tcattatgaa    3720
aatggatgcc atttgattaa ggctgatgac taacaaaatg atttgtgttt actcgaagtg    3780
ttttttttaaa aatagctact caaggatagt tttccataaa tcaagaaggt aaaaaagttc    3840
ccatttttta ttgtagaatc cattatttaa actacatgta gagacaggtt attatttgct    3900
atattcaagt ttggtcatca ataccccttaa aaatattaga attttatgga tgacccagaa    3960
atgctttgaa aatctgtgtt cctcagcaaa tacagagacc atgatcaaaa tgcacagaat    4020
cactaacatt ttgatgctag catggtttca gtctatttgg cagaacagaa ttgattatgc    4080
tactaaaatt tcttttttctt ttttttttttt tttttttttg agacagagtc ttgctttgtc    4140
acccaggctg aagtgcagtg gcaggatctc agttcactgc aacctctgcc tcccaggttc    4200
acgccattct cctgcttcag cctcccgagt agctgggact acaggctccc accaccatgc    4260
ccggctaatt ttttgcattt ttagtagaga cggggtttca ccgtgttagc caggatggtc    4320
tcgatctcct gacctcgtga tccgcccgcc tcagccttcc aaagtgctgg gattacaggc    4380
gtgagccact gtgcccggac tctgattttt tttttactaa ggtacagtaa gaaaagggaa    4440
aagtgtacgt tttcacttcc tgaaatatgt caggttgaat caataataga gcacaccaga    4500
actcttggct ccatttcaac ctaaactatt cagttctcat caccccagag gaaattccgc    4560
ctctgtgctg gtcagtaatc cccctggatt ataaaagttt aactaactca ctgtgcacaa    4620
```

```
ggcacggcca ttgccaacat tctcttgcaa ggtattttcc caagcccctta cccaattctg    4680 tttccatgat tgtgacattg gggattaatt ctgcaagaca gaactgttta tattctgtac    4740
cttaaaaaca catgcaaaca tctcttgcct taagatttct ggctttccta tggcccagag    4800
tcctagaagt gttttgatat ttgtagcaga attttcaagt gtacatcctt atcctggata    4860
ttaacatttt tgcatcatat tggcagctgg acctacagag aatttagtag actgttaacc    4920
taataagcct tgaatccttt tgcaccagtg gtgagagaat gtggatcaga gccatcacct    4980
ccatgccccg tcaccctcta acaaccacat ttacaacttc cccagctctg agacacactt    5040
gcctccaccc cttccatcac cccatttttaa gatgaaaata ccacaccagc ctggaaggaa    5100
gaagttactt gcccagggcc acatagtgag ttaagggctg atctagagct aggaagctgt    5160
cttcctgaac cataatcctg gactcttcta acctctctac tcatcgcaaa tagagttcat    5220
tttagtgatt tgaaggaaga tgggacaagt attttcaaac acctgtagga caacatggaa    5280
gtgggaggag acttctactg tagctcccca gagaagagag ctagggctac agagttgcag    5340
ttacaaggtt gccctctctg gcttgatccc caaaggaatt ttctactcca aaatagaatt    5400
tttctaggat gctatttctc agtccctgga gatactcaaa caaagggctt gtcacaaggg    5460
tttttgtaga agctattctt cacagaggtt gggggagaga ttaagccaaa ggatctctga    5520 ggtcttttc aaatctataa ttatgtggcc ttttgttcat tgacttccat gtgttctagt    5580
tgatcattac aaacctggca ggccttctca agggttcagt aattagctgt catttcccat    5640
ttgtccagag agtgtccaac acaaaatacc cctaagatct tggccaatag agaaatgtca    5700
tggaatttta gaaatgacag tatctgcgga gtttattcca agttatatca tttcaaagat    5760
gaagaaaccc aggctcagag ggagccatca catccacacc ctgtcaccct tcgtggccag    5820
tgccagacag tagctagttg gatgctaaaa gtagaattta gatatcttaa caataagccc    5880
agcagtcttt caacttcatt cgtaaatcat ttttgttttg agcatctgtc acgtggcagc    5940
acttgcctgg atactggaga gctgagaagg aatgcgacag gcaagtccta ctctcacagt    6000
gtatacattc aggaggaaca agacacacag tgccaagtaa ataaagtagc tgaacttcat    6060
caaatgattt tattcttaaa gtcattaaag catgtaatgt tcccctttt ttgtttcagg    6120 ggtgtacaga ttgaagaagt gtaggtgttt atgtggtttt agtgacaaac cccatgtgct    6180
ttcattgatt ttatgtttta tgttaaaaca tcaaccgcaa ggtaaaatgc atattgtatg    6240
ttgttggata cgtacttaac tggtatgcat cccatgtctt tgggtactag tgtatgaatt    6300
ctaatctctg taaatgaaat gttgtatgtg ttaatatatt taatagatgt aacttaataa    6360
actggcattg aagactgaag aattttcaca ctgtcaaaaa aaaaaaaaaa aa              6412
```

<210> SEQ ID NO 3  
<211> LENGTH: 251  
<212> TYPE: PRT  
<213> ORGANISM: Homo sapiens

<400> SEQUENCE: 3

```
Met Ala Glu Asp Leu Gly Leu Ser Phe Gly Glu Thr Ala Ser Val Glu
 1               5                  10                  15

Met Leu Pro Glu His Gly Ser Cys Arg Pro Lys Ala Arg Ser Ser Ser
            20                  25                  30

Ala Arg Trp Ala Leu Thr Cys Cys Leu Val Leu Pro Phe Leu Ala
        35                  40                  45

Gly Leu Thr Thr Tyr Leu Leu Val Ser Gln Leu Arg Ala Gln Gly Glu
```

```
              50                  55                  60
Ala Cys Val Gln Phe Gln Ala Leu Lys Gly Gln Glu Phe Ala Pro Ser
 65                  70                  75                  80

His Gln Gln Val Tyr Ala Pro Leu Arg Ala Asp Gly Asp Lys Pro Arg
                 85                  90                  95

Ala His Leu Thr Val Val Arg Gln Thr Pro Thr Gln His Phe Lys Asn
            100                 105                 110

Gln Phe Pro Ala Leu His Trp Glu His Glu Leu Gly Leu Ala Phe Thr
        115                 120                 125

Lys Asn Arg Met Asn Tyr Thr Asn Lys Phe Leu Leu Ile Pro Glu Ser
    130                 135                 140

Gly Asp Tyr Phe Ile Tyr Ser Gln Val Thr Phe Arg Gly Met Thr Ser
145                 150                 155                 160

Glu Cys Ser Glu Ile Arg Gln Ala Gly Arg Pro Asn Lys Pro Asp Ser
                165                 170                 175

Ile Thr Val Val Ile Thr Lys Val Thr Asp Ser Tyr Pro Glu Pro Thr
            180                 185                 190

Gln Leu Leu Met Gly Thr Lys Ser Val Cys Glu Val Gly Ser Asn Trp
        195                 200                 205

Phe Gln Pro Ile Tyr Leu Gly Ala Met Phe Ser Leu Gln Glu Gly Asp
    210                 215                 220

Lys Leu Met Val Asn Val Ser Asp Ile Ser Leu Val Asp Tyr Thr Lys
225                 230                 235                 240

Glu Asp Lys Thr Phe Phe Gly Ala Phe Leu Leu
                245                 250

<210> SEQ ID NO 4
<211> LENGTH: 5828
<212> TYPE: DNA
<213> ORGANISM: Mus musculus

<400> SEQUENCE: 4
actcagtgtg acagctgctc tcttatttaa tggggggctc tctggtcaga agggatcaga      60
agtctctcca agacagcaga aggatggcag aggagctggg gttgggcttc ggagaaggag     120
tcccagtgga agtgctgccg aaggctgtag acacaggcc agaggccagg gccgggctag      180
ctgccaggag caaagcctgc ctggctctca cctgctgcct gttgtcattt cccatcctcg     240
caggacttag caccctccta atggctggcc agctccgggt ccccggaaaa gactgtatgc     300
ttcgggccat aacagaagag agatctgagc cttcaccaca gcaagtttac tcacctccca     360
gaggcaagcc gagagcacac ctgacaatta gaaacaaac cccagcacca catctgaaaa      420
atcagctctc tgctctacac tgggaacatg acctagggat ggccttcacc aagaacggga     480
tgaagtacat caacaaatcc ctggtgatcc agagtcagg agactatttc atctactccc      540
agatcacatt ccgagggacc acatctgtgt gtggtgacat cagtcggggg agacgaccaa     600
acaagccaga ctccatcacc atggttatca ccaaggtagc agacagctac cctgagcctg     660
cccgcctact aacagggtcc aagtctgtgt gtgaaataag caacaactgg ttccagtccc     720
tctaccttgg ggccacgttc tccttggaag aaggagacag actaatggta aacgtcagtg     780
acatctcctt ggtggattac acaaaagaag ataaaacttt ctttggagct ttcttgctat     840
aaggaggaga aaccatcat tccagggggc tccctgcct cctactttcc aatttccttt       900
tctcatatgg atctataaac aggggcttta gagggatcag ggaaggggac agtggtttag     960
ctatataatt taggaaccca atattgatcc gtatatgcct tatggactaa aatagtaaat    1020
```

```
ggaaaaccca gtacagctca tgtttgatag agacctgctg ggttttaaaa attgaaacac   1080
gcctcatcca atggcacaat ctactgattt caggacagaa cctttccaca gtgccctctg   1140
tccaagtcct ttctgaattc agcagttcag ttagagctga attcgacaat gaacttactc   1200
cagatcaaga gctaaagaca gaatccaaag aaagactgag aaaatgatgt tatttctcca   1260
agaggcaatg catttccaca ttcttttgtg cctaacctaa aaaataagaa agaagaaagg   1320
aaggaaggaa ggaaggaagg aaggaaggaa ggaaggaagg aaggaaggaa ggaaggaagg   1380
aaggaaggga caagaaaaga caagacaaga caagaaaaaa gaaaaaatgg tatttctcgt   1440
gaatattccc taaaaggaat tggttttctg ctgtgaagga gaaacctcac ctttcttctg   1500
attgcatcct ttagtatcca acatacaag tgggaattcc aaatgcacat ggaacataga   1560
acacttttat tattgtgaga acatgtttat tgagtaccta ctatgctctg ggcactcagc   1620
ccacaggacc atgaagagaa agtcaaattt tcttaaaaac taaatgaatc ctcaatacat   1680
acttcctgat caactaccac tcaaaatgta aacttccaa agtataactt caagtcagcc    1740
atctaggtgg tttcttgggt aaaggtgctt gtcattaagc ctgacacctg ggtttgacct   1800
cccagaaccc aaaagctgga aggagagaat tggttcccac aaattatcct caaaccccca   1860
tacaaatgat gtggcatgca cacatgtaac taaataaata agtgtaaaac aaaaacaaaa   1920
acaaaatttt aaagaaaaat ttcaagtcct gaaagacagc attcctgaga atgttgtctc   1980
catcgttgtc cagtataggc taaccagctg atagagacac tgaaggaatt taaagacaga   2040
catcaagtga aatggagcac tgtagaaaca cttgattcat gccaggagtc aatgtactat   2100
gaagaccaac aacaaagtgt cagtcatcaa atccagaggt gtttatctag atctgctttc   2160
aagtttggtt tgcagccttt atatagtctc tattacaaat gctcgtgtca tggtagatgc   2220
cacaaggagt cagagggtaa acttagcccc aaaccactgc tgagccatct tctaggaaac   2280
cttcgaagca gagctgggca gcgtgactcc cacacaatga ctgggaaagt agtagctgat   2340
caaaatttgt tgagtaataa tttgttagaa aattcatctc cactgcctac taaacctaag   2400
ttgtatacta tctagcttct gctaagccaa cttacattgg ccactttttc tgtcttcaac   2460
ttcttgaagt atcacaggtc tcagtgagaa cacagggaaa ggtgaggtcg ccttcccctg   2520
gttcttcata ggggaaacca cacctgaaag aagatgagca gcctgaggtg acctggagga   2580
agggctgtct cagaagaagg acttattttt tggcttaggt ctaaaacctt gagagtaatg   2640
ctcactggtc aattgaggat gctttatcaa tgactccagt ctgactccaa ggtcagaaag   2700
gagagtgaga tgctctctct gcctgcatat atcttcatgg aacatgagaa tattgagcaa   2760
catagactta taggaaaaca cttgcccaaa agtagccaga gtgacctggt catcccctct   2820
actaaaccca agctttgtgt caagggcctt caaagctgcc cagaagtgat ctggatggct   2880
tgggaattta tccaagacag gaatttcctg acagccaaag atgcttgagt ccttgtgcct   2940
gacatgcatt tattttgccc ctgttttattg aagactgtaa ctgttgattt gtgggtatac   3000
atacatacat acatacatac atacatacat acatacatat gctgtcatga aggcagcatc   3060
aaacattact aattggactc aaaccagcat ttctgtttcc aagatactaa gtattcccat   3120
gcaaacagga gcatgctatt tttctaaagc aaaatgaaaa aaatagtttt gaaagtatat   3180
atatgatgga gtcaagtgta atggcataca tctgtaaacc cagcacatgg gatgctgagc   3240
caggaggatt gccgtgagtt tgaggagaac agggggctaaa tagtaatttt caggaaagcc   3300
ttgcctatat aacaagacct tgtctcaaat gaaaaaaaaa aaaaaatag accccaggct   3360
```

```
ggtccttgga gataaggtaa tatattcatt gggtgagggg gtgtgtgttt tggaaaatag    3420
ttaatttagt gagaaatgct tttcggtcaa atgcatctca aaggctgctg aattcaaatc    3480
gggtctgtaa atgcttacct agtgcttgct tgccctgggg acagagacat aaattacttt    3540
agtctcagat ccactcgttc taacagattg catctccat cgtctgtgga gcttttaatc     3600
actctgtttg tattagctaa ttaattagct aacttgagac acactgatat tttcttatta    3660
taaacatggg tgccatttga taaaagacaa tcattaacaa aatggttcga atttccgctt    3720
aagtgatctt cttttttcct tttcatttt tttaactagc taatcaaagg tagtttccca     3780
aaaataaatg caaagggagt ataaagaaaa aattccctgt ggtgggagct agtattgaaa    3840
caacagtatc aaagaggctg ttacctactg gcctcaaatt ttggcaggaa cgcctttgaa    3900
aatgttagaa ctttacggac agcctagagg tgctttgaaa agtctctgtt gccaacaaaa    3960
gccattaatc agcatgcggc acaggttact caaattttga ccttgactgt tttttagatc    4020
tgttacacag aacacaactt ctgggctgta atctctgatg tggatttggt gatttactaa    4080
ggtaccgtgg gaaacaagga aagtgtactt gtaccacatc gtttctcagt gcatgtcaga    4140
gtctactcaa cagcagggca tgccagagcc ttggatacat tccgggacaa actatgtcac    4200
tcctaaggaa attccaagtg tgtgcctgtc aagcactctg gatcatagaa gcccacgagt    4260
tcactgtgca caaggcacag ccatggccag cactctcttg catggtattt ctcttaagct    4320
cttactcaat cacggtccca tgattgtgac attggggatt aattgcttga gcaggtttat    4380
ttacagtctg ttccttgcaa aatacatgca gatatgtctg cctcaaaat ccctgattg      4440 ttttagggct tagagaatac tggggatgtt tttgctgttt tcagatgtac tttatttaag    4500
cttgcagaat taccctgaat attaacagtg ttctaagata ttgcctgcta gcttctggct    4560
aatttactag tggtgacagt atcagatcag agtatctata tttatgtctt gctattatag    4620
ttaaaacttc ctgatctctg taacacactc accctacct catctatcta cccatcttgt      4680
ggatgtagct gtgagaagac tcacaagccc gagttgcagt tacttttctg aagcaacata    4740
gtatgttaat ggaatggcca gaactctact cttggcacat ggcactgaat ttgatgccac    4800
taaaagaaaa attgaaggca gaaatatttt ttactatgca tgggacaacg tagaagagca    4860
aggagactgc ttacacatgg tggtcacatc tctggcttca tccctaaacc aattttctga    4920
ccccaagtcg atttttttc atgtagttat tgttcatttt ctggaaagag tcaagcaaaa     4980
agagagtttt atagaaacca ttgcatcatg gaggtcaggg gagggattaa gccaaagaat    5040
tccttctcca aatctatagc catatggcca cccttttggtg tacttctatt tgatcatgac    5100
aaacctgaga gccctgccca gagttcagtg gatcctaatg aactccaaga gtaattcatt    5160
ccctcaccaa ctctaggggc ttggccagtg cagaaaatgt catgggattt taaagttaac    5220
atgagctgct atccaaactt atgtctcttt aagaatggag agacacaggc caggagaggt    5280
aacatatgaa gcctggtatt gggcagtagc ttgatggagt attgaggcta aaagtagact    5340
tcctgcccct gaccatacac aacacccttt cagtttgatc catggtggtc ttattctact    5400
ttattttgag cacctgtcac acctagttac tgtcatgcca agaaggtcca taacaggcaa    5460
atcctactct gctgtgtgca cacaagagga aggaggctca cagtagcaag taaacagata    5520
agcaaacgta cacgattttc gtcttaaagt cattaagaca cacgcgtacc cctcttttgt    5580
ttcagagggt atacaggctg aacagatgtc agtgttcacc tattcttatt gataagcccc    5640
atgtgctttc attggttgaa tgtttttatgt taaaacgtca tattgccatc gtaaaatgca    5700
tattgtatgt tgttgggtat ataattaact aatatgcatc gcatgtatga attctaatct    5760
```
ctgtaaatga aaacttatat atgttaacat atgtaatagt tataatttaa taaactgaca     5820
ctggagac                                                              5828

<210> SEQ ID NO 5
<211> LENGTH: 270
<212> TYPE: PRT
<213> ORGANISM: Mus musculus

<400> SEQUENCE: 5

Met Gly Gly Ser Leu Val Arg Arg Asp Gln Lys Ser Leu Gln Asp Ser
1               5                   10                  15

Arg Arg Met Ala Glu Glu Leu Gly Leu Gly Phe Gly Glu Gly Val Pro
            20                  25                  30

Val Glu Val Leu Pro Glu Gly Cys Arg His Arg Pro Glu Ala Arg Ala
        35                  40                  45

Gly Leu Ala Ala Arg Ser Lys Ala Cys Leu Ala Leu Thr Cys Cys Leu
    50                  55                  60

Leu Ser Phe Pro Ile Leu Ala Gly Leu Ser Thr Leu Leu Met Ala Gly
65                  70                  75                  80

Gln Leu Arg Val Pro Gly Lys Asp Cys Met Leu Arg Ala Ile Thr Glu
                85                  90                  95

Glu Arg Ser Glu Pro Ser Pro Gln Gln Val Tyr Ser Pro Pro Arg Gly
            100                 105                 110

Lys Pro Arg Ala His Leu Thr Ile Lys Lys Gln Thr Pro Ala Pro His
        115                 120                 125

Leu Lys Asn Gln Leu Ser Ala Leu His Trp Glu His Asp Leu Gly Met
    130                 135                 140

Ala Phe Thr Lys Asn Gly Met Lys Tyr Ile Asn Lys Ser Leu Val Ile
145                 150                 155                 160

Pro Glu Ser Gly Asp Tyr Phe Ile Tyr Ser Gln Ile Thr Phe Arg Gly
                165                 170                 175

Thr Thr Ser Val Cys Gly Asp Ile Ser Arg Gly Arg Arg Pro Asn Lys
            180                 185                 190

Pro Asp Ser Ile Thr Met Val Ile Thr Lys Val Ala Asp Ser Tyr Pro
        195                 200                 205

Glu Pro Ala Arg Leu Leu Thr Gly Ser Lys Ser Val Cys Glu Ile Ser
    210                 215                 220

Asn Asn Trp Phe Gln Ser Leu Tyr Leu Gly Ala Thr Phe Ser Leu Glu
225                 230                 235                 240

Glu Gly Asp Arg Leu Met Val Asn Val Ser Asp Ile Ser Leu Val Asp
                245                 250                 255

Tyr Thr Lys Glu Asp Lys Thr Phe Phe Gly Ala Phe Leu Leu
            260                 265                 270

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
tgttccccat atccagtgtg g                                                21

<210> SEQ ID NO 7
<211> LENGTH: 20

```
<212> TYPE: DNA
<213> ORGANISM: Artificial Sequence
<220> FEATURE:
<223> OTHER INFORMATION: Synthetic oligonucleotide

<400> SEQUENCE: 7
ctggaggctg cgaaggattt                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
atgcttcggg ccataacaga                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
tgaaggccat ccctaggtca                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10
accacagtcc atgccatcac                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11
tccaccaccc tgttgctgta                                               20
```